United States Patent
Falco et al.

(10) Patent No.: US 12,146,144 B2
(45) Date of Patent: Nov. 19, 2024

(54) METHODS AND COMPOSITIONS FOR GENERATING COMPLEX TRAIT LOCI

(71) Applicants: PIONEER HI-BRED INTERNATIONAL, INC., Johnston, IA (US); CORTEVA AGRISCIENCE LLC, Indianapolis, IN (US)

(72) Inventors: Saverio Carl Falco, Wilmington, DE (US); Michael Lassnser, Portland, OR (US); Zhongsen Li, Hockessin, DE (US); Christopher J. Scelonge, Ankeny, IA (US)

(73) Assignees: PIONEER HI-BRED INTERNATIONAL, INC., IA (US); CORTEVA AGRISCIENCE LLC, IN (US)

( * ) Notice: Subject to any disclaimer, the term of this patent is extended or adjusted under 35 U.S.C. 154(b) by 0 days.

(21) Appl. No.: 18/459,484

(22) Filed: Sep. 1, 2023

(65) Prior Publication Data
US 2024/0093214 A1 Mar. 21, 2024

Related U.S. Application Data

(63) Continuation of application No. 17/699,260, filed on Mar. 21, 2022, now Pat. No. 11,788,097, which is a continuation of application No. 16/551,195, filed on Aug. 26, 2019, now Pat. No. 11,312,969, which is a continuation of application No. 13/748,704, filed on Jan. 24, 2013, now Pat. No. 10,435,699.

(60) Provisional application No. 61/591,329, filed on Jan. 27, 2012.

(51) Int. Cl.
*C12N 15/82* (2006.01)
*C12N 9/22* (2006.01)
*C12N 9/16* (2006.01)

(52) U.S. Cl.
CPC .......... *C12N 15/8213* (2013.01); *C12N 9/22* (2013.01); *C12N 9/16* (2013.01)

(58) Field of Classification Search
None
See application file for complete search history.

(56) References Cited

U.S. PATENT DOCUMENTS

2009/0093059 A1* 4/2009 Baszczynski .......... C12N 15/90
435/468

OTHER PUBLICATIONS

Buckner et al 1990 (The Plant Cell 2: p. 867-876) (Year: 1990).*

* cited by examiner

*Primary Examiner* — Matthew R Keogh

(57) ABSTRACT

Compositions and methods are provided for stacking multiple independent transgenic loci into the genome of a plant. Compositions include plants, seeds or plant cells comprising at least one transgenic target site and at least one genomic locus of interest integrated at different genomic sites within a genomic window. Plant breeding techniques can be employed such that the transgenic target site and the genomic locus of interest can be bred together. In this way, multiple independent transgene integrations can be generated within a genomic window to create a complex trait locus. The complex trait locus is designed such that the transgenic target sites and/or genomic loci of interest can segregate independently of each other, thus providing the benefit of altering a complex trait locus by breeding-in and breeding-away specific elements. Various methods can also be employed to modify the target sites such that they contain a variety of polynucleotides of interest.

22 Claims, 15 Drawing Sheets
Specification includes a Sequence Listing.

FIG. 1A

Design of a Complex Trait locus comprising multiple SSI Target Sites for Trait Stacking by Crossing (A to D is a 10 cM genomic region; GI = gene of interest; TG = transgene)

Event 1 with FRT1/87 sites at B

A →B← C D

Insert GI1 using FLP/FRT

Event 2 with GI1 between FRT sites at B

A B C D

Genetic Cross (if 5 cM apart, 5% will have both)

Transgenic Event 3 (TG at C)

A B C D

GI1   TG1

 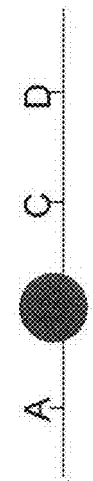
A B C D
Transgenic Event 4

Re-transformation

Event 4 = Complex trait locus with GI1 and TG1 stacked (Can repeat to introduce GI1 and GI3 etc. see next slide)

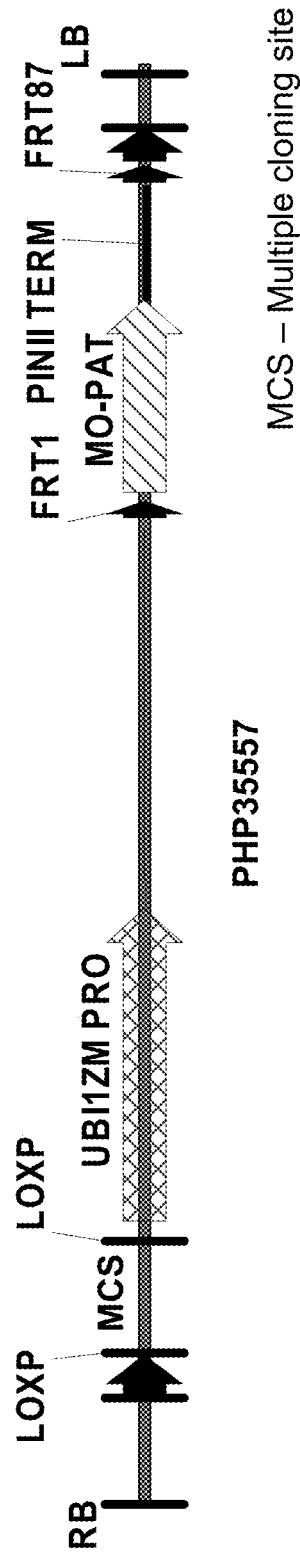
FIG. 2A  SSI Platform II Intermediates
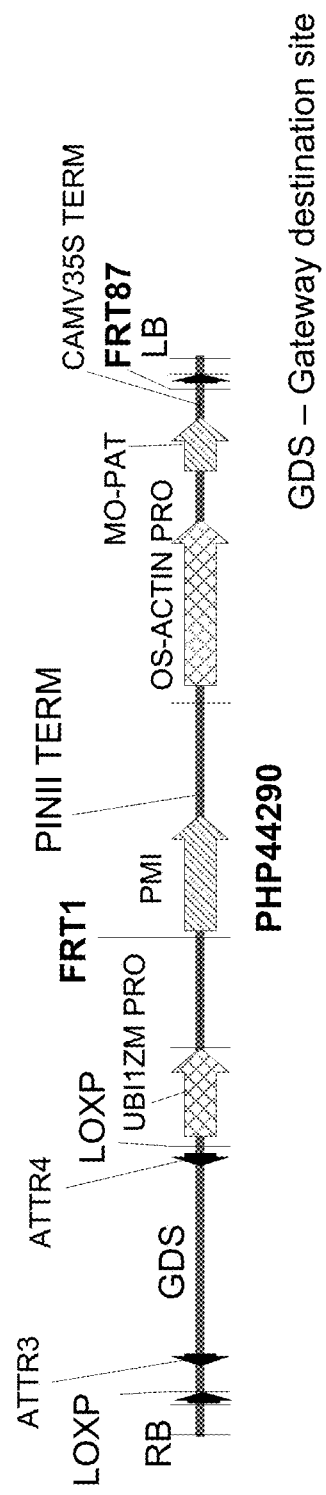
FIG. 2B  SSI Platform II Intermediates Plasmid PHP44556

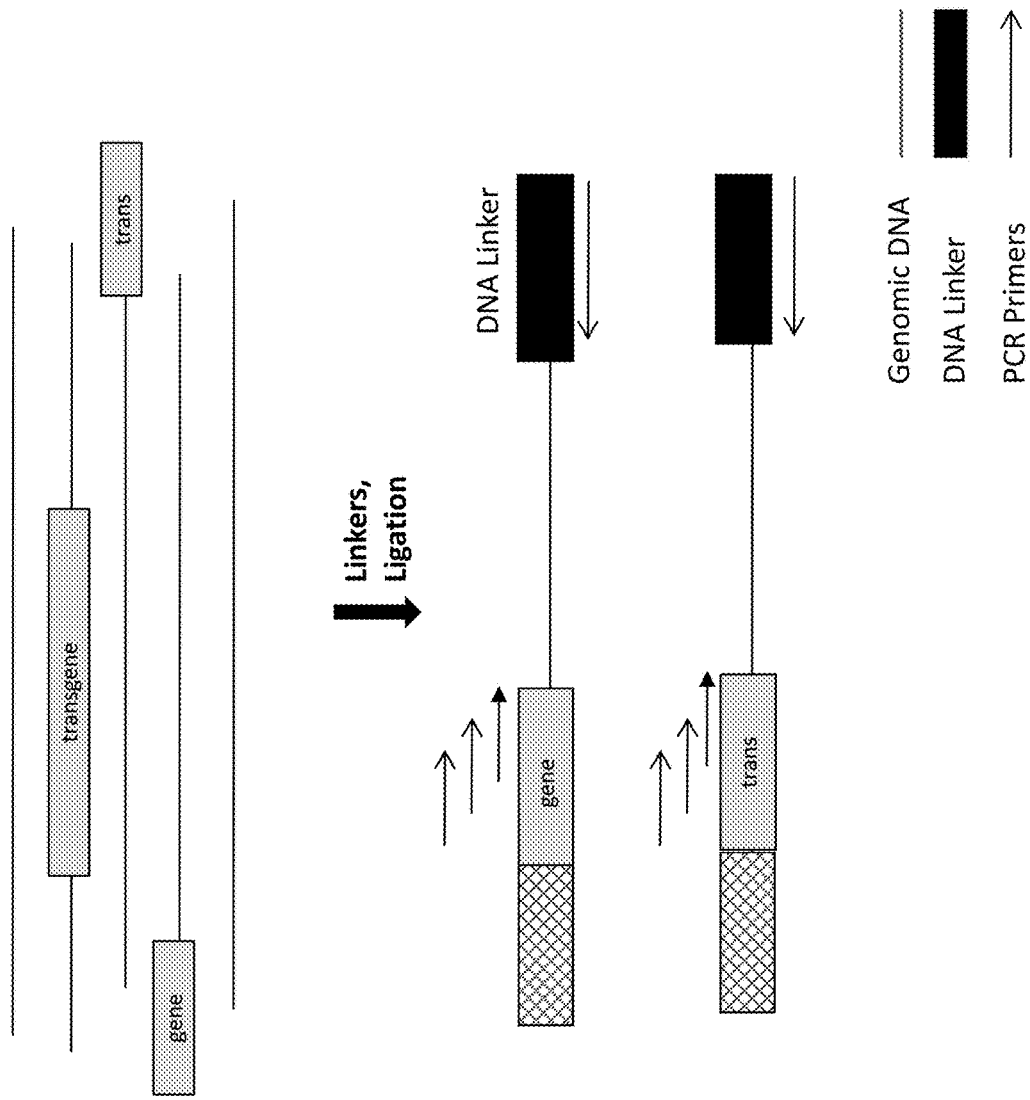
FIG. 4 LMnPCR for Insertion Site Flanking Sequence

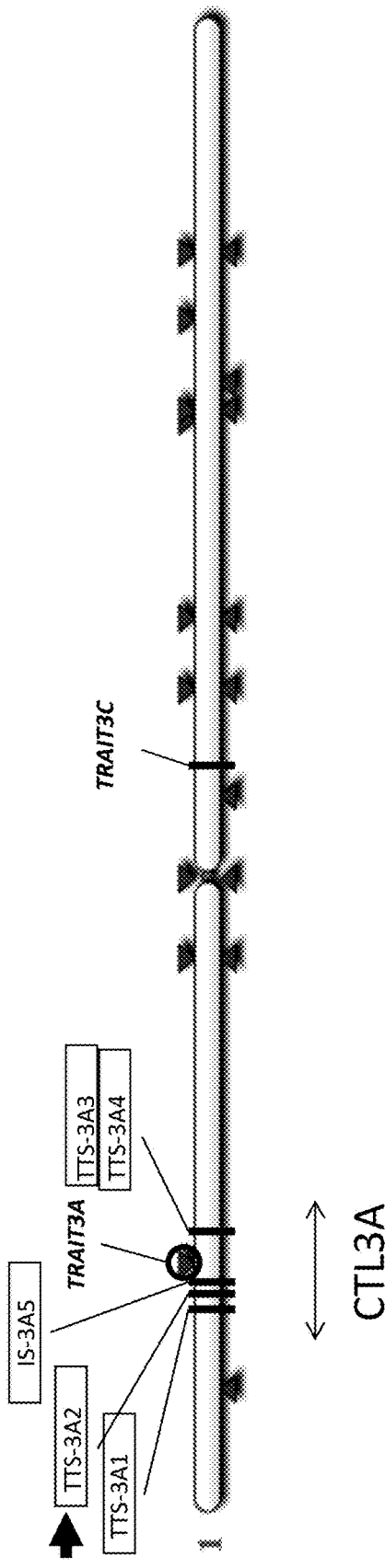
FIG. 5A TTS candidates for CTL3A on chromosome 1 near Trait3A
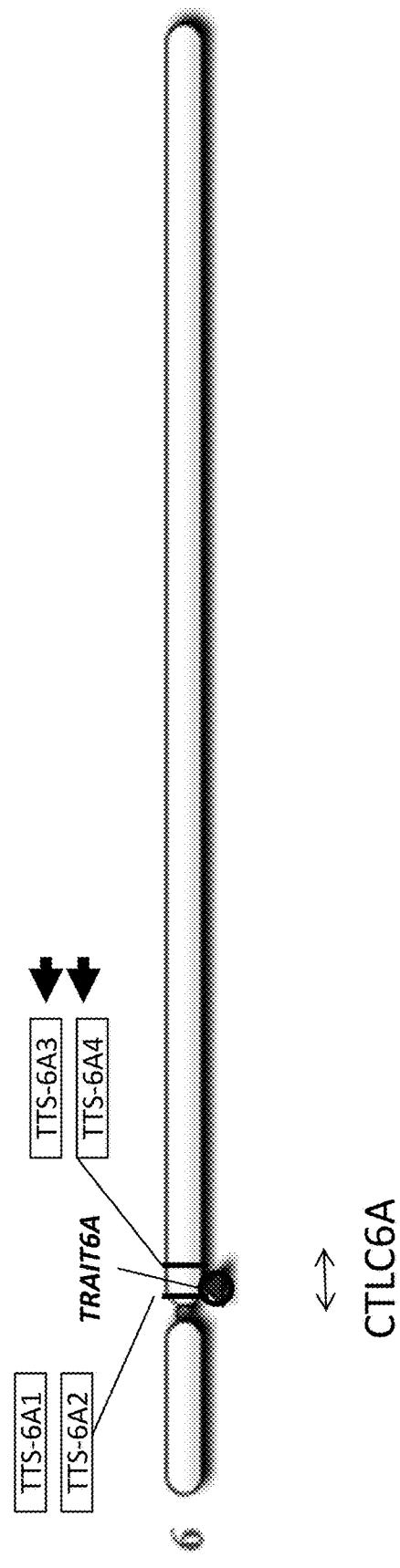
FIG. 5B TTS candidates for CTL6A on chromosome 6 near Trait6A

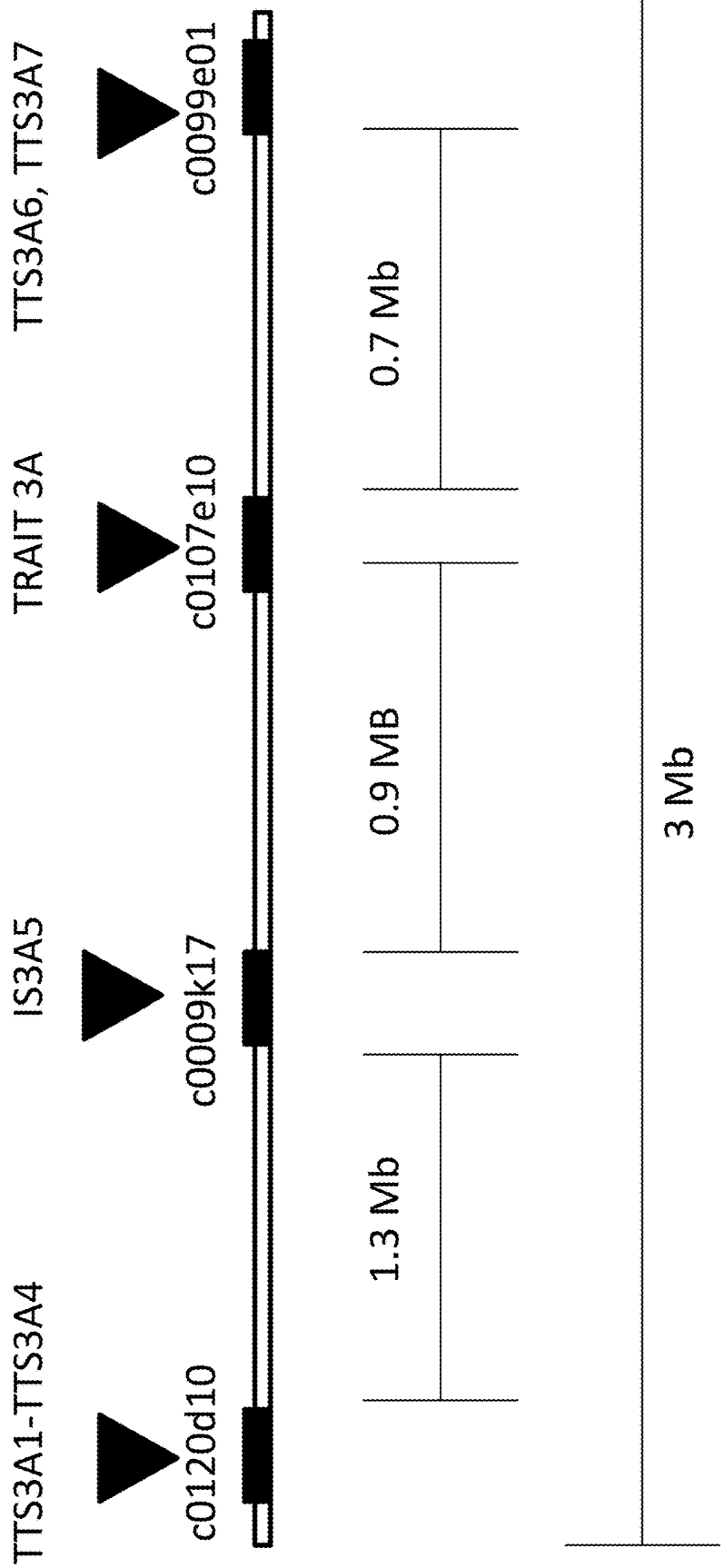
FIG. 6 Complex Trait Locus CTL-3A on Chromosome 1 of corn
*Physical map distances are estimates based on B73 public assembly and may differ slightly depending on genetic composition.

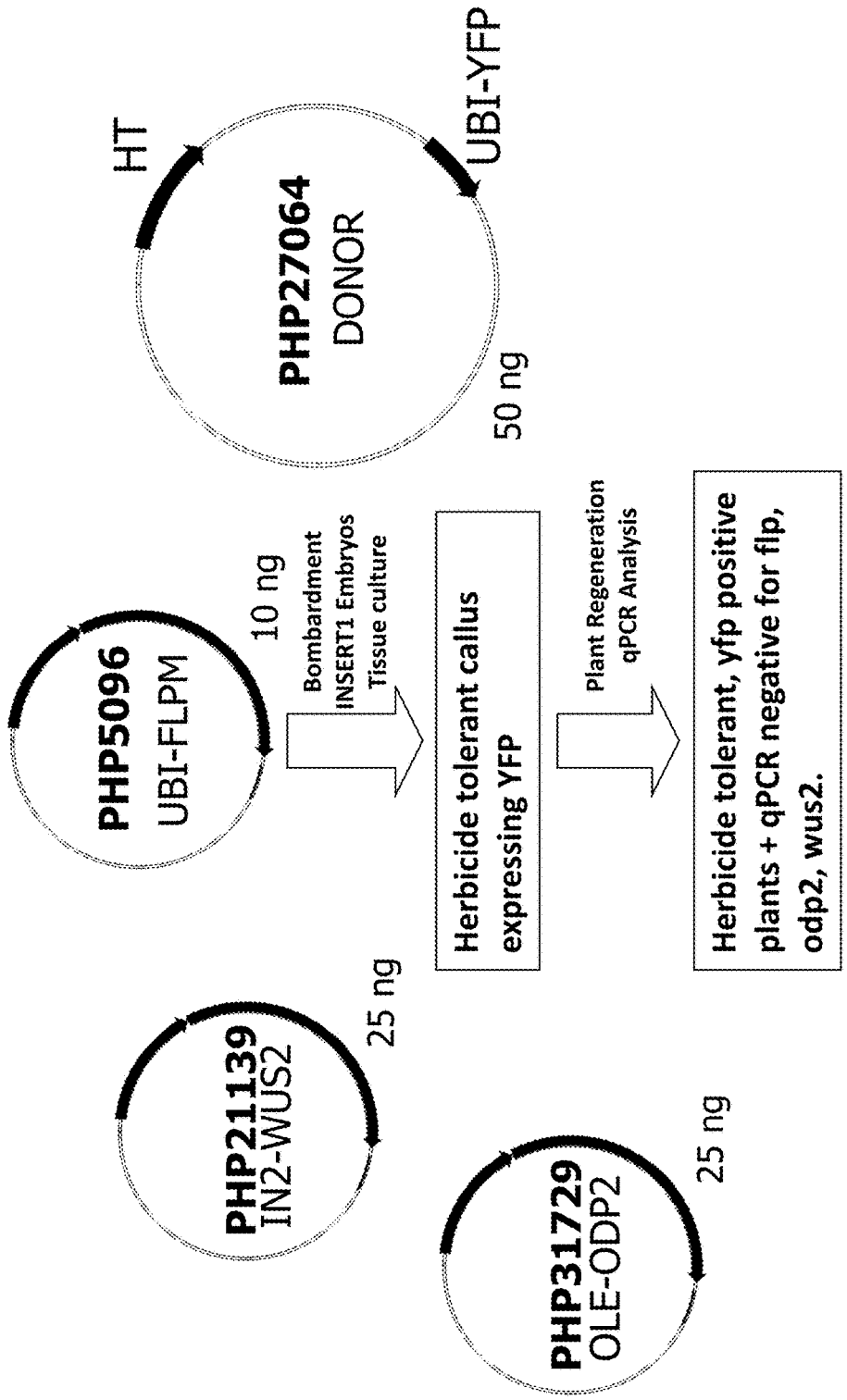
FIG. 7: Particle bombardment for Site Specific Integration

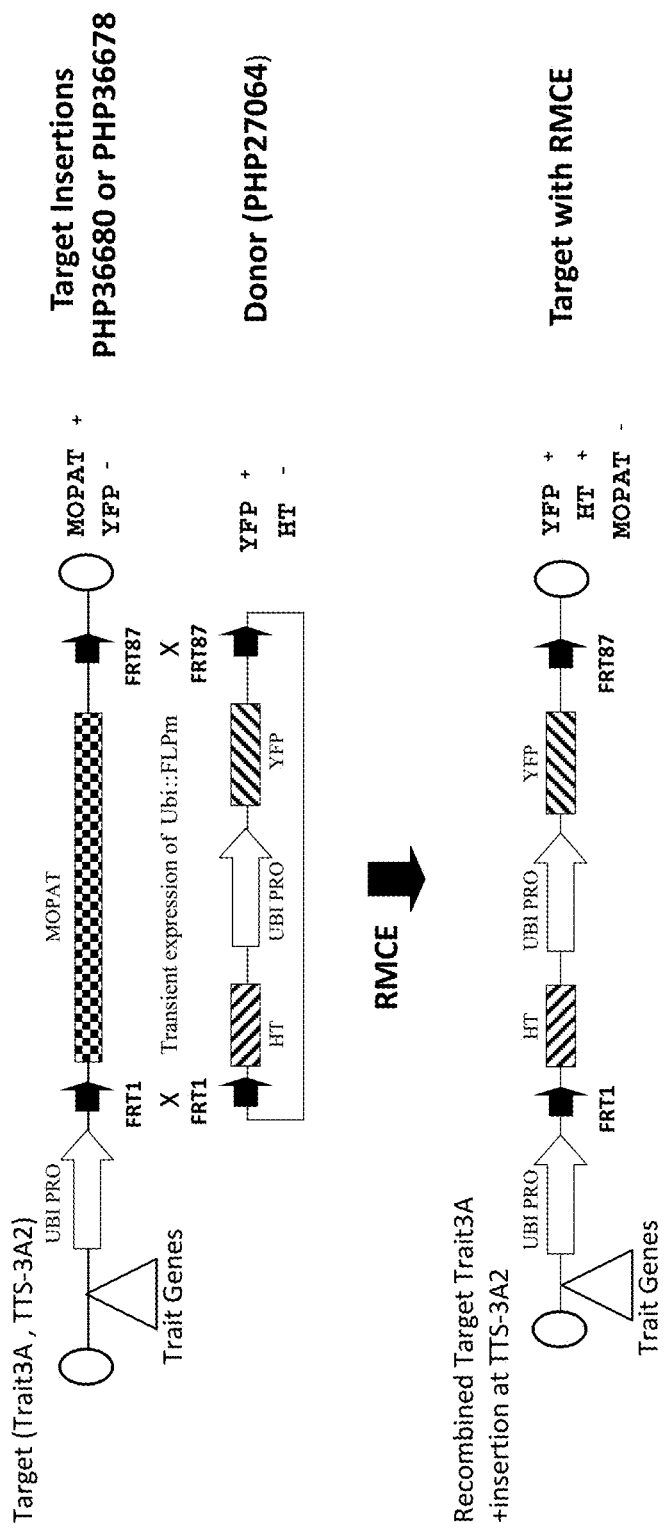
FIG. 8: Site Specific Integration

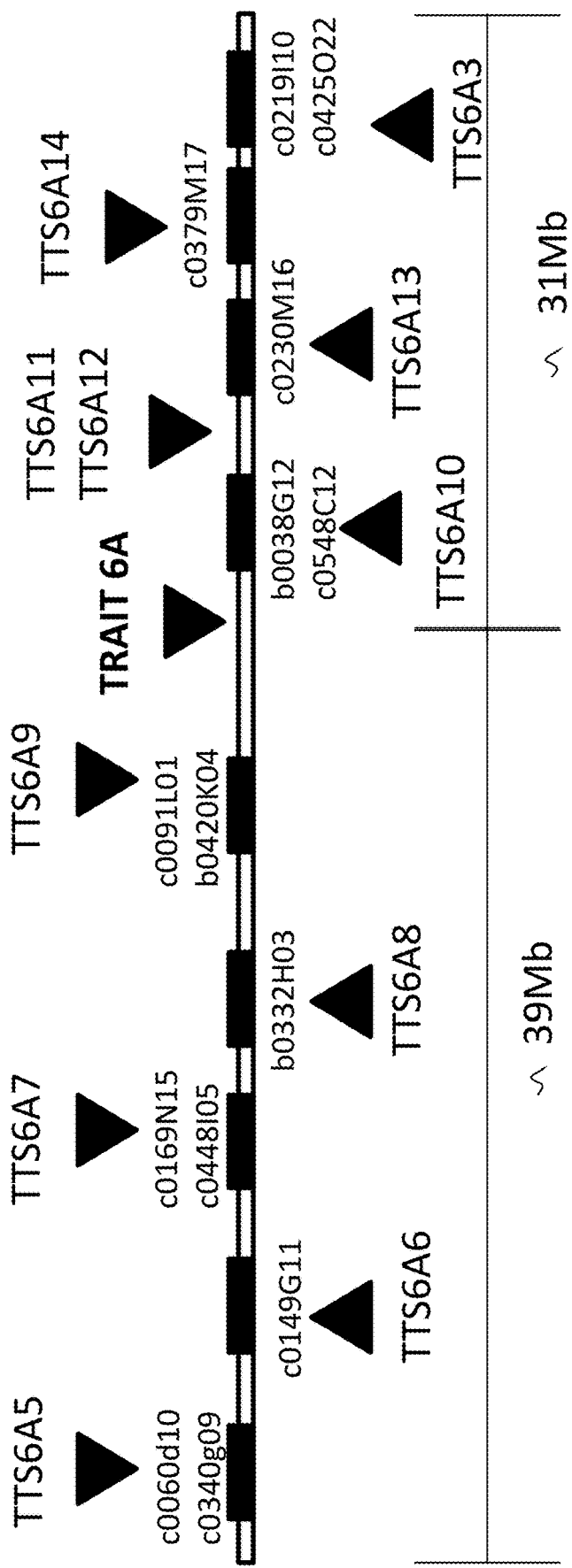
FIG. 9. Complex Trait Locus CTL-6A on Chromosome 6 of corn
*Physical map distances are estimates based on B73 public assembly and may differ slightly depending on genetic composition.

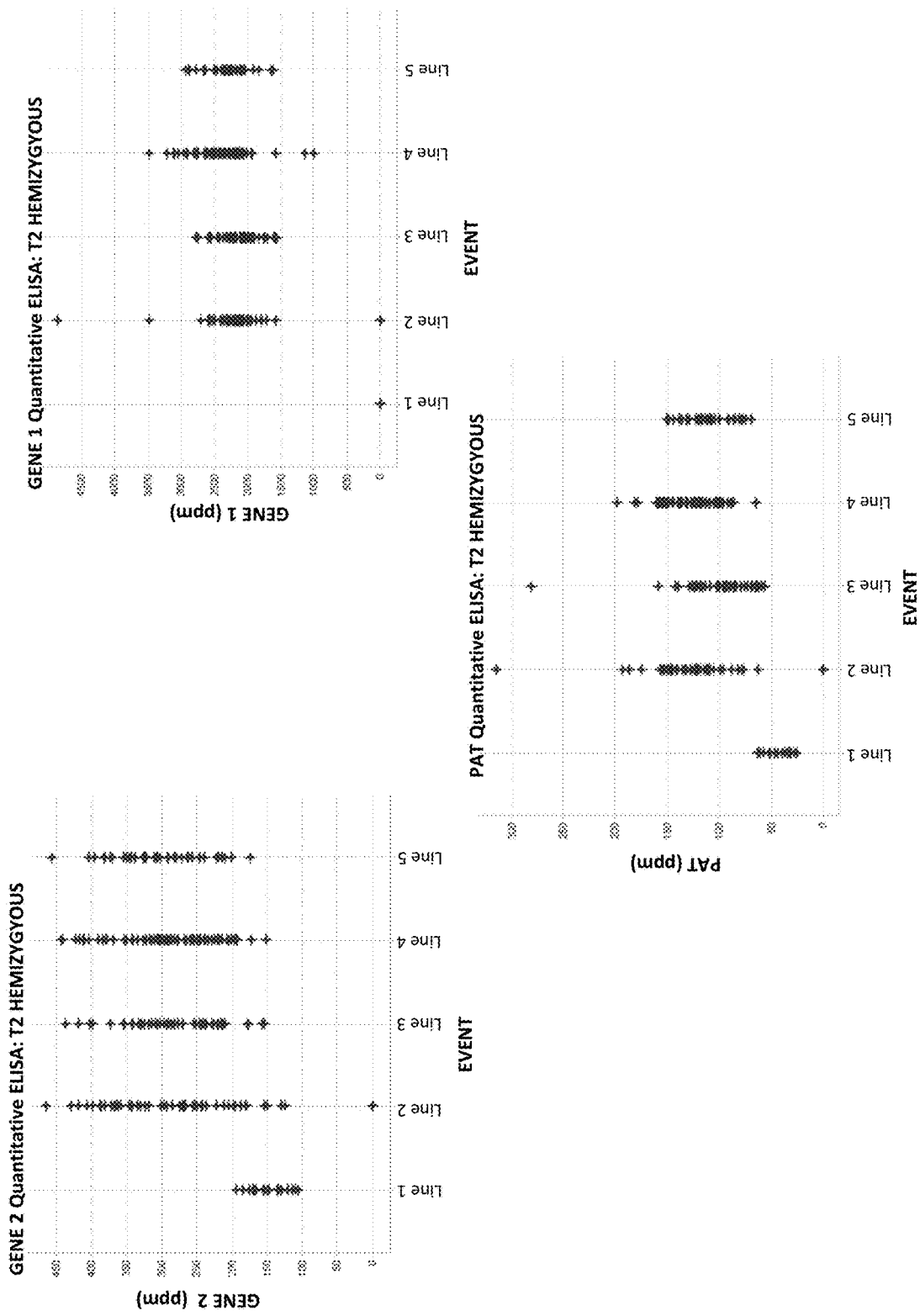
FIG. 10: Expression analysis of several insertions at one genomic position.

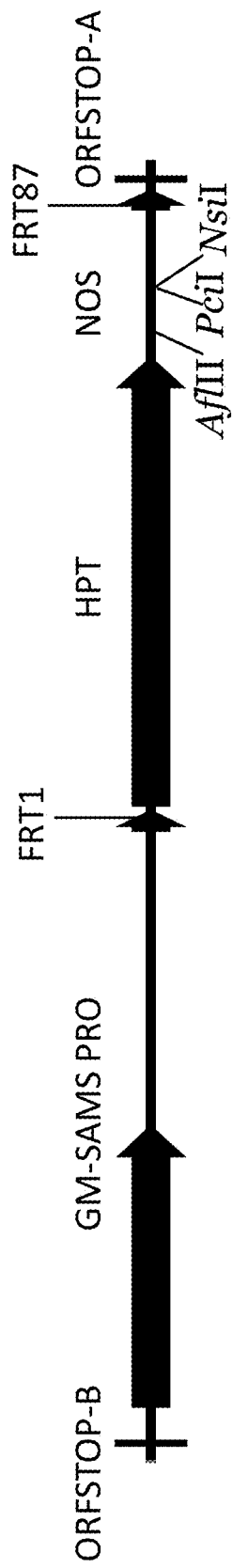
FIG. 11 QC599A, 2963 bp

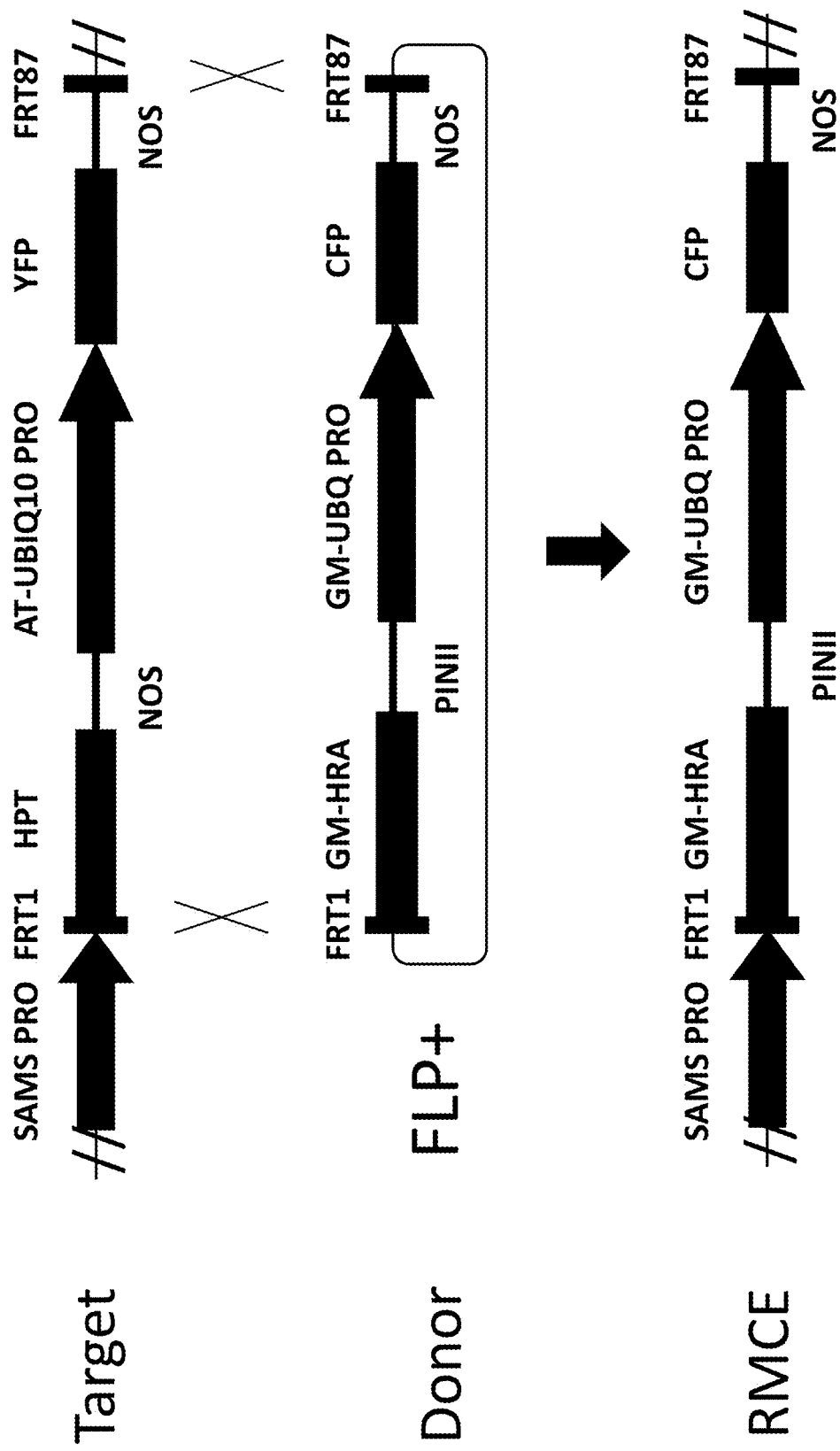
FIG. 12 FLP recombinase mediated cassette exchange in soybean

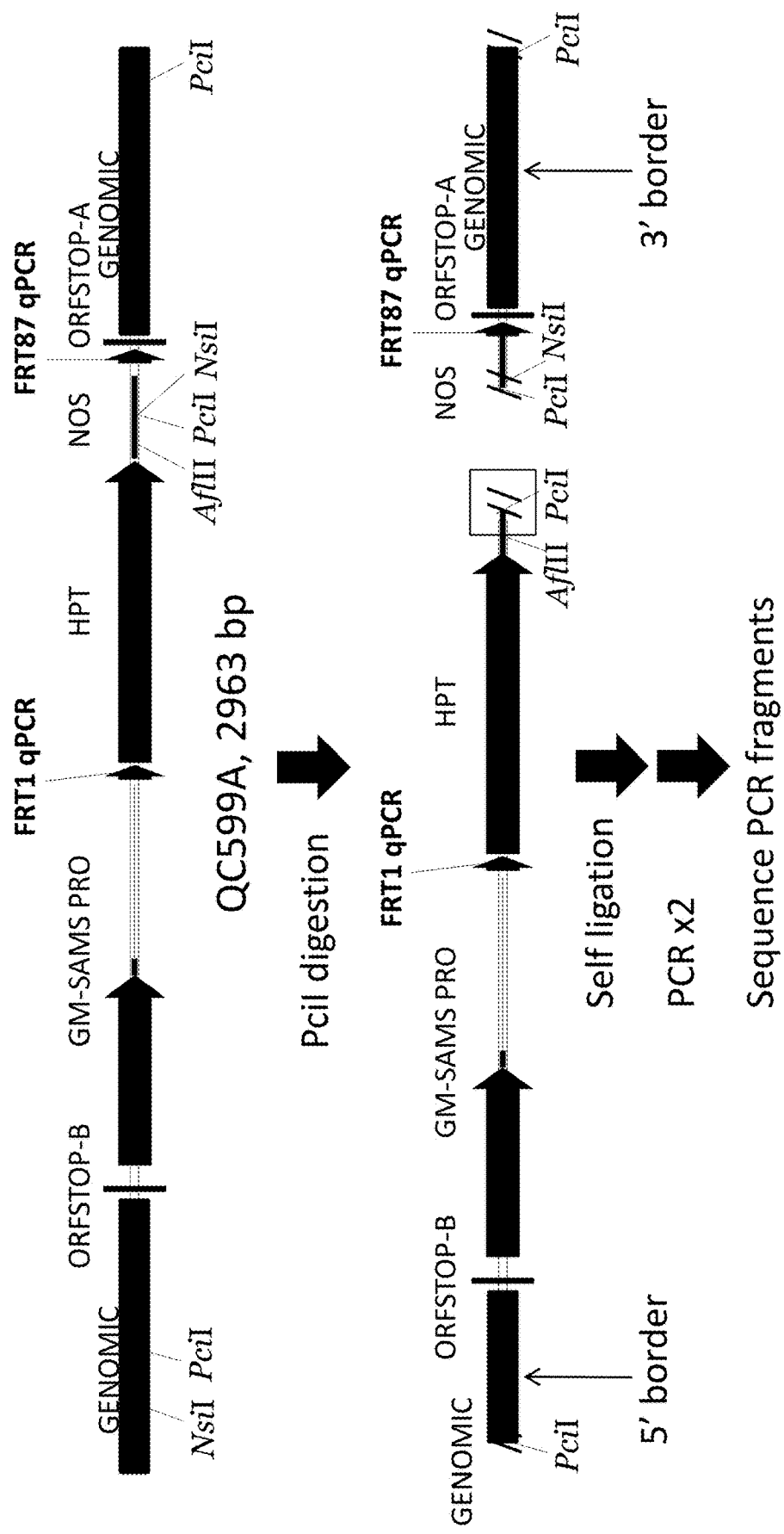
FIG. 13 Identification of SSI target lines

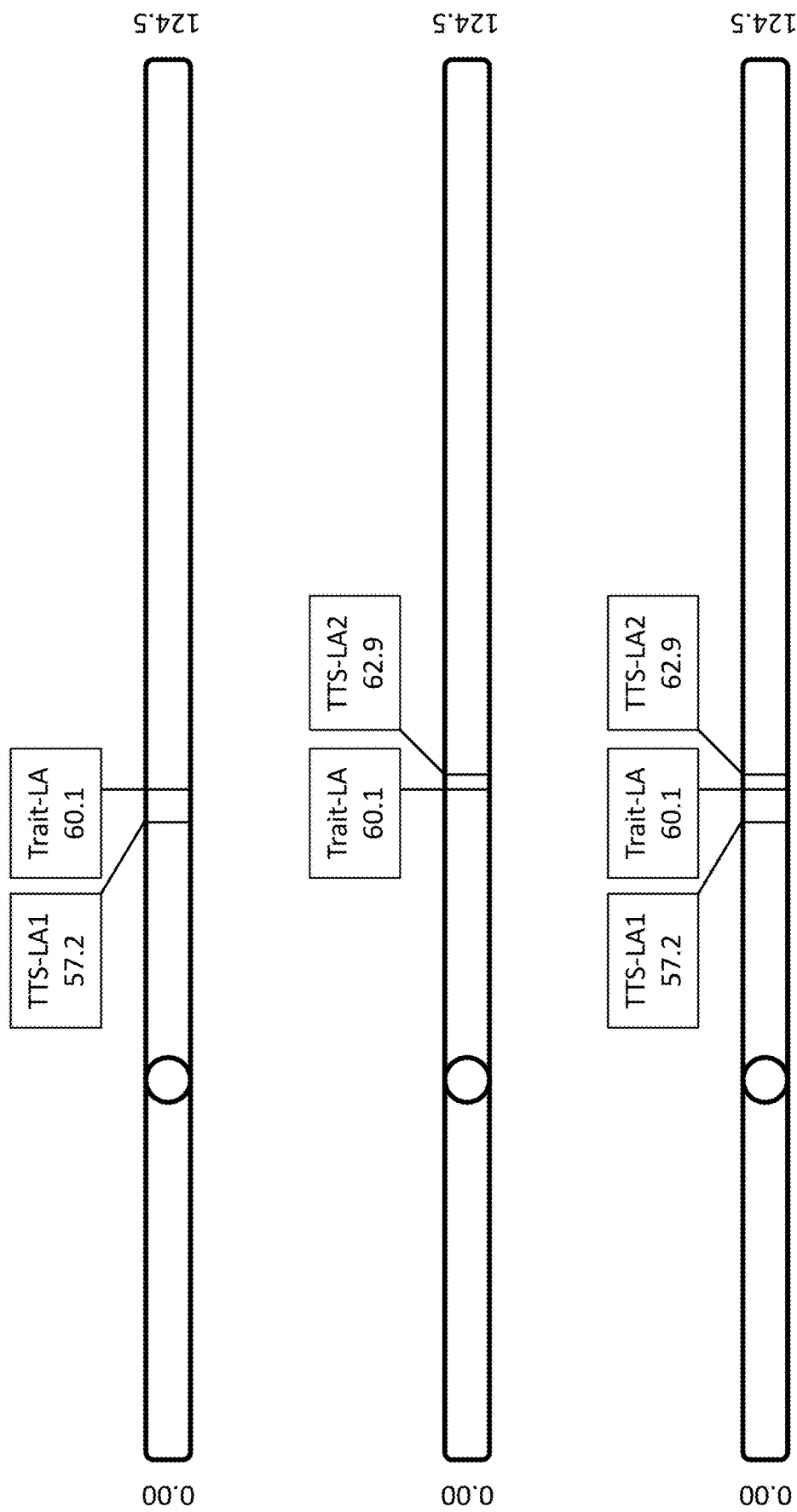
FIG. 14 Complex trait locus CTL-LA on chromosome 19 (L) in soybean

SEQUENCE LISTING

```
Sequence total quantity: 13
SEQ ID NO: 1            moltype = DNA   length = 30
FEATURE                 Location/Qualifiers
misc_feature            1..30
                        note = Minimal FRT1 Recombination Site
source                  1..30
                        mol_type = other DNA
                        organism = synthetic construct
SEQUENCE: 1
agttcctata ctttctagag aataggaact                                         30

SEQ ID NO: 2            moltype = DNA   length = 30
FEATURE                 Location/Qualifiers
misc_feature            1..30
                        note = Minimal FRT5 Recombination Site
source                  1..30
                        mol_type = other DNA
                        organism = synthetic construct
SEQUENCE: 2
agttcctata ctcttttgag aataggaact                                         30

SEQ ID NO: 3            moltype = DNA   length = 30
FEATURE                 Location/Qualifiers
misc_feature            1..30
                        note = Minimal FRT6 Recombination Site
source                  1..30
                        mol_type = other DNA
                        organism = synthetic construct
SEQUENCE: 3
agttcctata cttttgaag aataggaact                                          30

SEQ ID NO: 4            moltype = DNA   length = 30
FEATURE                 Location/Qualifiers
misc_feature            1..30
                        note = Minimal FRT7 Recombination Site
source                  1..30
                        mol_type = other DNA
                        organism = synthetic construct
SEQUENCE: 4
agttcctata cttattgaag aataggaact                                         30

SEQ ID NO: 5            moltype = DNA   length = 30
FEATURE                 Location/Qualifiers
misc_feature            1..30
                        note = Minimal FRT12 Recombination Site
source                  1..30
                        mol_type = other DNA
                        organism = synthetic construct
SEQUENCE: 5
agttcctata ctctatgtag aataggaact                                         30

SEQ ID NO: 6            moltype = DNA   length = 30
FEATURE                 Location/Qualifiers
misc_feature            1..30
                        note = Minimal FRT87 Recombination Site
source                  1..30
                        mol_type = other DNA
                        organism = synthetic construct
SEQUENCE: 6
agttcctata ctttctggag aataggaact                                         30

SEQ ID NO: 7            moltype = DNA   length = 1032
FEATURE                 Location/Qualifiers
misc_feature            1
                        note = Nucleotide sequence encoding Cre Recombinase
source                  1..1032
                        mol_type = genomic DNA
                        organism = Bacteriophage P1
SEQUENCE: 7
atgtccaatt tactgaccgt acaccaaaat ttgcctgcat taccggtcga tgcaacgagt    60
gatgaggttc gcaagaacct gatggacatg ttcagggatc gccaggcgtt ttctgagcat   120
acctggaaaa tgcttctgtc cgtttgccgg tcgtgggcgg catggtgcaa gttgaataac   180
cggaaatggt ttcccgcaga acctgaagat gttcgcgatt atcttctata tcttcaggcg   240
cgcggtctgg cagtaaaaac tatccagcaa catttgggcc agctaaacat gcttcatcgt   300
cggtccgggc tgccacgacc aagtgacagc aatgctgttt cactggttat gcggcggatc   360
cgaaaagaaa acgttgatgc cggtgaacgt gcaaaacagg ctctagcgtt cgaacgcact   420
gatttcgacc aggttcgttc actcatggaa aatagcgatc gctgccagga tatacgtaat   480
ctggcatttc tggggattgc ttataacacc ctgttacgta tagccgaaat tgccaggatc   540
```

```
agggttaaag atatctcacg tactgacggt gggagaatgt taatccatat tggcagaacg    600
aaaacgctgg ttagcaccgc aggtgtagag aaggcactta gcctgggggt aactaaactg    660
gtcgagcgat ggatttccgt ctctggtgta gctgatgatc cgaataacta cctgttttgc    720
cgggtcagaa aaaatggtgt tgccgcgcca tctgccacca gccagctatc aactcgcgcc    780
ctggaaggga tttttgaagc aactcatcga ttgatttacg cgctaagga tgactctggt    840
cagagatacc tggcctggtc tggacacagt gcccgtgtcg gagccgcgcg agatatggcc    900
cgcgctggag tttcaatacc ggagatcatg caagctggtg gctggaccaa tgtaaatatt    960
gtcatgaact atatccgtaa cctggatagt gaaacagggg caatggtgcg cctgctggaa    1020
gatggcgatt ag                                                        1032

SEQ ID NO: 8            moltype = DNA   length = 1260
FEATURE                 Location/Qualifiers
misc_feature            1
                        note = Nucleotide sequence encoding FLP recombinase
source                  1..1260
                        mol_type = genomic DNA
                        organism = Saccharomyces cerevisiae
SEQUENCE: 8
atgccacaat ttggtatatt atgtaaaaca ccacctaagg tgcttgttcg tcagtttgtg    60
gaaaggtttg aaagaccttc aggtgagaaa atagccattat gtgctgctga actaacctat    120
ttatgttgga tgattacaca taacggaaca gcaatcaaga gagccacatt catgagctat    180
aatactatca taagcaattc gctgagtttc gatattgtca taaatcact ccagtttaaa    240
tacaagacgc aaaaagcaac aattctggaa gcctcattaa agaaattgat tcctgcttga    300
gaatttacaa ttattcctta ctatggacaa aaacatcaat ctgatatcac tgatattgta    360
agtagtttgc aattacagtt cgaatcatcg gaagaagcag ataagggaaa tagccacagt    420
aaaaaaatgc ttaaagcact tctaagtgag ggtgaaagca tctgggagat cactgagaaa    480
atactaaatt cgtttgagta tacttcgaga tttacaaaaa caaaaacttt ataccaattc    540
ctcttcctag ctactttcat caattgtgga agattcagcg atattaagaa cgttgatccg    600
aaatcattta aattagtcca aaataagtat ctgggagtaa taatccagtg tttagtgaca    660
gagacaaaga caagcgttag taggcacata tacttcttta gcgcaagggg taggatcgat    720
ccacttgtat atttggatga atttttgagg aattctgaac cagtcctaaa acgagtaaat    780
aggaccggca attcttcaag caataaacag gaataccaat tattaaaaga taacttagtc    840
agatcgtaca ataaagcttt gaagaaaaat gcgccttatt caatctttgc tataaaaaat    900
ggcccaaaat ctcacattgg aagacatttg atgaccctct ttctttcaat gaagggccta    960
acggagttga ctaatgttgt gggaaattgg agcgataagc gtgcttctgc cgtgccagg    1020
acaacgtata ctcatcagat aacagcaata cctgatcact acttcgcact agtttctcgg    1080
tactatgcat atgatccaat atcaaaggaa atgatagcat tgaaggatga gactaatcca    1140
attgaggagt ggcagcatat agaacagcta aagggtagtg ctgaaggaag catacgatac    1200
cccgcatgga atgggataat atcacaggag gtactagact acctttcatc ctacataaat    1260

SEQ ID NO: 9            moltype = DNA   length = 1032
FEATURE                 Location/Qualifiers
misc_feature            1..1032
                        note = Nucleotide sequence encoding Cre protein from
                           Bacteriophage P1 having maize preferred codons (moCRE)
source                  1..1032
                        mol_type = other DNA
                        organism = synthetic construct
SEQUENCE: 9
atgtccaacc tgctcacggt tcaccagaac cttccggctc ttccagtgga cgcgacgtcc    60
gatgaagtca ggaagaacct catggacatg ttccgcgaca ggcaagcgtt cagcgagcac    120
acctggaaga tgctgctctc cgtctgccgc tcctgggctg catggtgcaa gctgaacaac    180
aggaagtggt tccccgctga gcccgaggac gtgagggatt accttctgta cctgcaagct    240
cgcgggctgg cagtgaagac catccagcaa caccttggac aactgaacat gcttcacagg    300
cgctccggcc tcccgcgccc cagcgactcg aacgccgtga gctcgtcat ggccgatc    360
aggaaggaaa acgtcgatgc cggcgaaagg gcaaagcagg ccctcgcgtt cgagaggacc    420
gatttcgacc aggtccgcag cctgatggag aacagcgaca ggtgccagga cattaggaac    480
ctggcgttcc tcggaattgc atacaacacg ctcctcagga tcgcggaaat tgcccgcatt    540
cgcgtgaagg acattagccg caccgacggc ggcaggatgc ttatccacat tggcaggaco    600
aagacgctcg tttccaccgc aggcgtcgaa aaggcctca gcctcggagt gaccaagtc    660
gtcgaacgct ggatctccgt gtccggcgtc gcggacgacc caaacaacta cctcttctgc    720
cgcgtccgca gaacggggt ggctgcccct agcgccacca gccaactcag cacgagggcc    780
ttggaaggta ttttcgaggc cacccaccgc ctgatctacg gcgcgaagga tgacagcggt    840
caacgctacc tcgcatggtc cgggcactcc gcccgcgttg gcgctcgtag ggacatggct    900
cgcgccggtg tttccatccc cgaaatcatg caggcgggtg gatggacgaa cgtgaacatt    960
gtcatgaact acattcgcaa ccttgacagc gagacgggcg caatggttcg cctcctggaa    1020
gatggtgact ga                                                        1032

SEQ ID NO: 10           moltype = DNA   length = 1260
FEATURE                 Location/Qualifiers
misc_feature            1..1260
                        note = Nucleotide sequence encoding FLP protein having
                           maize preferred codons (FLPm)
source                  1..1260
                        mol_type = other DNA
                        organism = synthetic construct
SEQUENCE: 10
atgccccagt tcgacatcct ctgcaagacc ccccccaagg tgctcgtgag gcagttcgtg    60
gagaggttcg agaggccctc cggcgagaag atcgccctct cgcgccgccga gctcacctac    120
```

```
ctctgctgga tgatcaccca caacggcacc gccattaaga gggccacctt catgtcatac    180
aacaccatca tctccaactc cctctccttc gacatcgtga acaagtccct ccagttcaaa    240
tacaagaccc agaaggccac catcctcgag gcctccctca agaagctcat cccgcctgg     300
gagttcacca tcatccccta ctacggccag aagcaccagt ccgacatcac cgacatcgtg    360
tcatccctcc agcttcagtt cgagtcctcc gaggaggctg acaagggcaa ctcccactcc    420
aagaagatgc tgaaggccct cctctccgag ggcgagtcca tctgggagat caccgagaag    480
atcctcaact ccttcgagta cacctccagg ttcactaaga ccaagaccct ctaccagttc    540
ctcttcctcg ccaccttcat caactgcggc aggttctcag acatcaagaa cgtggacccc    600
aagtccttca agctcgtgca gaacaagtac ctcggcgtga tcatccagtg cctcgtgacc    660
gagaccaaga cctccgtgtc caggcacatc tacttcttct ccgctcgcgg caggatcgac    720
cccctcgtgt acctcgacga gttcctcagg aactcagagc ccgtgctcaa gagggtgaac    780
aggaccggca actcctcctc caacaagcag gagtaccagc cctcaaggaa caacctcgtg    840
aggtcctaca acaaggccct caagaagaac gcccccatact ccatcttcgc catcaagaac    900
ggccccaagt cccacatcgg taggcacctc atgacctcct tcctctcaat gaagggcctc    960
accgagctca ccaacgtggt gggcaactgg tccgacaaga gggcctccgc cgtggccagg   1020
accacctaca cccaccagat caccgccatc ccgaccact acttcgccct cgtgtcaagg    1080
tactacgcct acgaccccat ctccaaggag atgatcgccc tcaaggacga gactaacccc   1140
atcgaggagt ggcagcacat cgagcagctc aagggctccg ccgagggctc catcaggtac   1200
cccgcctgga acggcatcat ctcccaggag gtgctcgact acctctcctc ctacatcaac   1260

SEQ ID NO: 11          moltype = DNA   length = 2963
FEATURE                Location/Qualifiers
misc_feature           1..2963
                       note = SSI target DNA fragment QC599A
source                 1..2963
                       mol_type = other DNA
                       organism = synthetic construct
SEQUENCE: 11
cgcgccggta cccgggtacc gagctcacta cgacgcgtga aattacctaa ttaacaccgg     60
tgtttaaaca ctagtaacgg ccgccagtgt gctggaattc gcccttccca agctttgctc    120
tagatcaaac tcacatccaa acataacatg gatatcttcc ttaccaatca tactaattat    180
tttgggttaa atattaatca ttatttttaa gatattaatt aagaaattaa aagatttttt    240
aaaaaaatgt ataaaattat attattcatg atttttcata catttgattt tgataataaa    300
tatattttt ttaatttctt aaaaaatgtt gcaagacact tattagacat agtcttgttc     360
tgtttacaaa agcattcatc atttaataca ttaaaaaata tttaatacta acagtagaat    420
cttcttgtga gtggtgtggg agtaggcaac ctggcattga aacgagagaa agagagtcag    480
aaccagaaga caaatgaaaaa gtatgcaaca aacaaatcaa aatcaaaggg caaaggctgg    540
ggttggctca attggttgct acattcaatt tcaactcag tcaacggttg agattcactc      600
tgacttcccc aatctaagcc gcggatgcaa acggttgaat ctaacccaca atccaatctc    660
gttacttagg gcttttccg tcattaactc accccctgcca cccggtttcc ctataaattg     720
gaactcaatg ctcccctcta aactcgtatc gcttcagagt tgagaccaag acacactcgt    780
tcatatatct ctctgctctt ctcttctctt tacctctcaa aggtactttt cttctccctc    840
taccaaatcc tagattccgt ggtcaattt cggatcttgc actctggtt tgctttgcct       900
tgcttttcc tcaactgggt ccatctagga tccatgtgaa actctactct ttctttaata    960
tctgcggaat acgcgtttga cttcagatc tagtcgaaat catttcataa ttgccttttct   1020
ttcttttagc ttatgagaaa taaatcact tttttttttat ttcaaaataa accttgggcc    1080
tgtgctgac tgagatgggg tttggtgatt acagaatttt agcgaatttt gtaattgtac    1140
ttgtttgtct gtagttttgt tttgtttct tgtttctcat acattcctta ggcttcaatt    1200
ttattcgagt ataggtcaca ataggaattc aaactttgag caggggaatt aatcccttcc    1260
ttcaaatcca gtttgtttgt atatatgttt aaaaaatgaa acttttgctt taaattctat   1320
tataactttt tttatggctg aaattttgc atgtgtcttt gctctctgtt gtaaatttat    1380
tgtttaggta ctaactctag gcttgttgtg cagtttttga agtataacaa cagaagttcc    1440
tattccgaag ttcctattct ctagaaagta taggaacttc cactagtcca tgaaaaagcc    1500
tgaactcacc gcgacgtctg tcgagaagtt tctgatcgaa aagttcgaca gcgtctccga   1560
cctgatgcag ctctccggagg gcgaagaatc tcgtgcttc agctcgatg tagggagggcg    1620
tggatatgtc ctgcgggtaa atagctcgcg cgatgctttc tacaaagatc gttatgttta    1680
tcggcacttt gcatccggcccg cgctcccgat tccgaagtg cttgacattg ggaattcag    1740
cgagagcctg acctattgca tctcccgccg tgcacagggt gtcacgttgc aagacctgcc    1800
tgaaaccgaa ctgcccgctg ttctgcagcc ggtcgcggag gccatggatg cgatcgctgc    1860
ggccgatctt agccagacga gcgggttcgg cccattcgga ccgcaaggaa tcggtcaata    1920
cactacatgg cgtgattttca tatgcgcgat tgctgatccc catgtgtatc actggcaaac   1980
tgtgatggac gacaccgtca gtgcgtccgt cgcgcaggct ctcgatgagc tgatgctttg    2040
ggccgaggac tgccccgaag tccggcacct cgtgcacgcg gatttcggct ccaacaatgt    2100
cctgacggac aatggccgca taacgactgg agcgaggcga tgttcgggga    2160
ttccaatac gaggtcgcca acatcttctt ctggaggccg tggttggctt gtatggagca     2220
gcagacgcgc tacttcgagc ggaggcatcc ggagcttgca ggatcgccgc ggctccgggc    2280
gtatatgctc cgcattggtc ttgaccaact ctatcagagc ttggttgacg caatttcga    2340
tgatgcagct tgggcgcagg tcgatgcga cgcaatcgtc cgatccggga ccggactgct    2400
cgggcgtaca caaatcgccc gcagaagcgc ggccgtctgg accgatggct gtgtagaagt    2460
actcgccgat agtggaaacc gacgcccag cactcgtccg agggcaaagg aatagtgagg    2520
tacctaaaga aggagtgcgt cgaagcagat cgttcaaaca tttggcaata agtttctta    2580
agattgaatc ctgttgccgg tcttgcgatg attatcatat aatttctgtt gaattacgtt   2640
aagcatgtaa taattaacat gtaatgcatg acgttattta tgagatgggt ttttatgatt   2700
agagtcccga aattatacat ttaatacgcg atagaaaaca aaatatagcg cgcaaactag    2760
gataaaattat cgcgcgcggt gtcatctatg ttactagatc gatgtcgacc cgggcctag    2820
gaggccggcc cagctgatga tcccggtgaa gttcctattc cgaagttcct attctccaga    2880
aagtatagga acttcactag agcttgcggc gcgcatgct gacttaatca gctaacgcca    2940
ctcgaggggg ggcccggtac cgg                                           2963
```

```
SEQ ID NO: 12            moltype = DNA  length = 17
FEATURE                  Location/Qualifiers
misc_feature             1..17
                         note = all open reading frame stop codon ORFSTOP-B
source                   1..17
                         mol_type = other DNA
                         organism = synthetic construct
SEQUENCE: 12
tgaaattacc taattaa                                                        17

SEQ ID NO: 13            moltype = DNA  length = 16
FEATURE                  Location/Qualifiers
misc_feature             1..16
                         note = all open reading frame stop codon ORFSTOP-A
source                   1..16
                         mol_type = other DNA
                         organism = synthetic construct
SEQUENCE: 13
tgacttaatc agctaa                                                         16
```

METHODS AND COMPOSITIONS FOR GENERATING COMPLEX TRAIT LOCI

CROSS-REFERENCE TO RELATED APPLICATIONS

This application is a Continuation of U.S. application Ser. No. 16/551,195 filed 26 Aug. 2019, now Allowed, which is a Continuation of U.S. application Ser. No. 13/748,704 filed 24 Jan. 2013, now Allowed as U.S. Pat. No. 10,435,699B2, which claims the benefit of U.S. Provisional Application No. 61/591,329, filed Jan. 27, 2012, each of which is hereby incorporated herein in its entirety by reference.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named BB1920USCNT_SequenceListing.TXT, created on 22 Aug. 2019, and having a size of 11,935 bytes and is filed concurrently with the specification. The sequence listing contained in this ASCII formatted document is part of the specification and is herein incorporated by reference in its entirety.

FIELD OF THE INVENTION

The invention relates to the field of plant molecular biology. In particular, methods and compositions are provided for altering the genome of a plant.

BACKGROUND OF THE INVENTION

Recombinant DNA technology has made it possible to insert foreign DNA sequences into the genome of an organism, thus, altering the organism's phenotype. The most commonly used plant transformation methods are *Agrobacterium* infection and biolistic particle bombardment in which transgenes integrate into a plant genome in a random fashion and in an unpredictable copy number.

Unfortunately, the problems associated with these methods can result in reduced agronomics, additional costs for further research, creation of additional transgenic events, and slower time to product. Thus, more efficient methods are needed for targeting the insertion of a sequence of interest into a desirable genomic position, for readily modifying the targeted polynucleotide and/or for stacking additional polynucleotides of interest near the desired integration site.

BRIEF SUMMARY OF THE INVENTION

Methods and compositions for producing in a plant a complex trait locus in a genomic window comprising at least one transgenic target site and at least one genomic locus of interest are provided. The compositions provide a plant or seed having in its genome a genomic window of about 10 cM in length wherein the genomic locus (loci) of interest, and the transgenic target site(s) have different genomic insertion sites and segregate independently from each other at a rate of about 10% to about 0.1%. The transgenic target sites can comprise at least a first recombination site and a second recombination site and the first and second recombination sites are dissimilar with respect to one another. The transgenic target sites can further comprise a polynucleotide of interest and can be altered by site-specific integration methods.

Further provided is a method of producing a complex trait locus in the genome of a plant comprising applying plant breeding techniques to a first plant having in its genome a genomic window of about 10 cM with at least a first transgenic target site. The method comprises breeding to said first plant a second plant comprising a first genomic locus of interest in the genomic window and selecting a progeny comprising said first transgenic target site and said first genomic locus of interest, wherein said first transgenic target site and said first genomic locus have different genomic insertion sites in said progeny plant. Using such methods, various transgenic target sites and/or polynucleotides of interest can be introduced into a genomic window. Also provided are methods of altering the complex trait locus by utilizing various breeding techniques or by employing site-specific recombination techniques to add, remove, or replace transgenic target sites, genomic loci of interest or polynucleotides of interest.

Additionally provided is a library of plants, seeds or plant cells comprising a transgenic target site and methods of making the library. The library comprises a population of plants, seeds or plant cells each comprising a transgenic target site having a different genomic insertion site and the transgenic target sites segregate independently from one another when combined into a single plant genome. Further provided are subpopulations of the library wherein each member comprises a transgenic target site with a different genomic insertion site within a given genomic window and said transgenic target sites segregate independently at a rate of about 10% to about 0.1% when present in the same genome. The transgenic target sites of the library can be located at defined intervals throughout a given genomic window such that all possible positions for transgenic target site insertion within the given genomic window are represented by the members of a population of the library. Thus, breeding techniques can be applied to given subpopulations of the libraries to produce a complex trait locus in a plant.

BRIEF DESCRIPTION OF THE DRAWINGS

FIG. 2A depicts the T-DNA region of SSI platform II variants for pPHP35557 and FIG. 2B depicts the same for pPHP44290. These plasmids are a derivative of an *Agrobacterium* binary vector intermediate related to pSB11 used for transformation of corn published in Komari, et al., 1996. A selectable marker gene(s) is located near the T-DNA left border sequence (LB). A multiple cloning site (not shown) (PHP35557) or a Gateway destination site (PHP44290) for addition of trait genes is added near the right T-DNA border (RB). The trait addition region is located between a pair of loxP sites for the capability to do CRE/lox excision. Site specific integration (SSI) capability is enabled by placing FRT sites, FRT1 and FRT87, around selectable marker gene(s).

FIG. 4 is a Schematic overview of ligation-mediated nested PCR (LMnPCR). Genomic DNA was extracted from leaf tissue of TO transgenic plants derived from the transformation process and then randomly sheared using mechanical force. DNA shearing generated large numbers of random fragments, a small subset of which contained a portion of the newly inserted transgene where it was contiguous with genomic DNA. The genomic DNA fragments with transgene sequence represent the genomic insertion site and the insertion site flanking sequence (FS) is defined by the region where genomic DNA is contiguous with transgene sequence. A defined DNA linker was ligated to the ends of random genomic fragments to facilitate the use of PCR methods to amplify the relatively rare transgene insertion fragments. PCR was designed using primers that hybridized to the ends of the transgene and primers that hybridized to the DNA linker. PCR bands that were amplified should contain FS and were submitted for sequence analysis and then confirmed. Confirmation of sequence results involved BLAST analysis of the amplified PCR sequence to the maize genome sequence database.

FIG. 5A depicts Transgenic target sites (TTS) and insertion site (IS) candidates for the complex trait locus CTL3A on maize chromosome 1. FIG. 5B depicts Transgenic target sites (TTS) candidates for the complex trait locus CTL6A on maize chromosome 6.

FIG. 6 is a Schematic of the transgenic target sites (TTS) and insertion sites (IS) of the CTL3A complex trait locus in relation to the genomic window of interest (TRAIT3A) and public BACS on the maize physical map.

FIG. 7 depicts Site specific integration in transgenic maize event comprising a transgenic target site for SSI.

FIG. 8 depicts Recombinase mediated cassette exchange (RMCE) at TTS-3A2 in complex trait locus CTL3A.

FIG. 9 is a Schematic of the transgenic target sites (TTS) of the CTL6A complex trait locus in relation to the genomic window of interest (TRAIT6A) and public BACS on the maize physical map.

FIG. 10 shows Expression analysis of several insertions at one genomic position.

FIG. 11 is a Schematic map of the QC599A DNA fragment used for biolistic soybean transformation to create transgenic SSI target events. FRT1 and FRT87 sites used for qPCR assays and three unique restriction sites AflII, NsiI, PciI used for inverse PCR are marked. The GM-SAMS PRO has an intron indicated by the solid line.

FIG. 12 is a Schematic description of FLP recombinase mediated cassette exchange in soybean. Target DNA previously integrated in soybean genome recombines with the donor DNA at both the FRT1 and FRT87 sites with the help of transiently expressed FLP recombinase. The target DNA cassette flanked by the FRT1 and FRT87 sites is replaced by the donor DNA cassette flanked by the FRT1 and FRT87 sites resulting site-specific integration of the donor cassette to the exact same genomic site of the target.

FIG. 13 depicts Identification of SSI target lines containing Transgenic Target Sites. The genomic DNA of single copy target events was separately digested with three restriction enzymes MlII, NsiI, and PciI that all cut the QC599A transgene only once and the nearby flanking genomic border DNA, for example the PciI digestion. The resulting mixed genomic border and QC599A transgene DNA fragment was circularized by self-ligation, PCR amplified, and sequenced. Two rounds of PCR amplifications using two sets of primers for each of the 5' border and 3' border were used to specifically amplify the border-QC599A DNA fragments.

FIG. 14 depicts the genetic location of transgenic SSI target sites TTS-LA1 and TTS-LA2 and one gene of interest (TRAITLA) in the genomic window comprising the complex trait locus CTL-LA on chromosome 19 in soybean. SSI target sites TTS-LA1 and TTS-LA2 were created independently and brought together by crossing.

DETAILED DESCRIPTION OF THE INVENTION

Figure 1B:
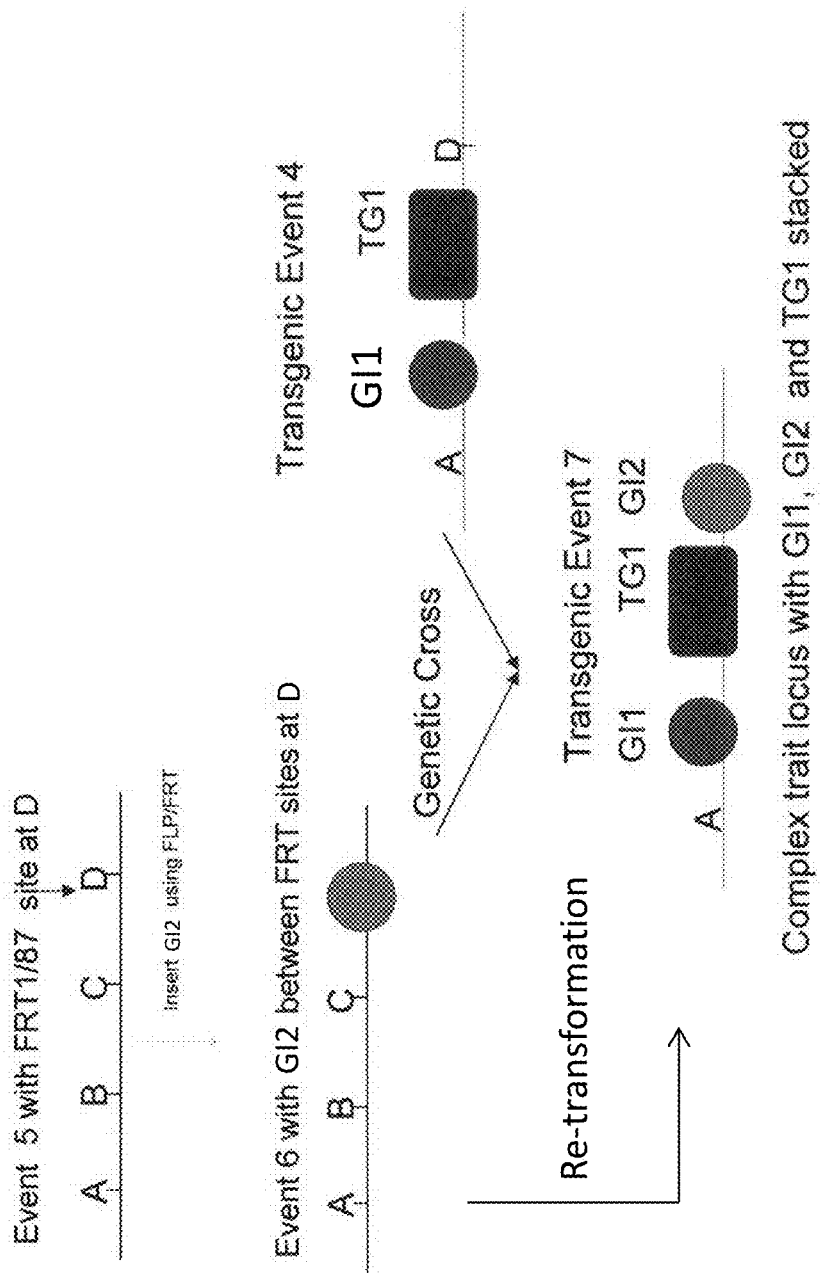
FIG. 1. A and FIG. 1B depict a non-limiting example design of a complex trait locus generated by crossing and/or retransformation is shown. GI indicates gene of interest and TG denotes a transgene. A to D is a 10 cM genomic region.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Compositions and methods are provided for stacking multiple independent transgenic loci into the genome of a plant. Compositions include plants, seeds or plant cells comprising at least one transgenic target site and at least one genomic locus of interest integrated at different genomic sites within a genomic window. Plant breeding techniques can be employed such that the transgenic target site and the at least one genomic locus of interest can be bred as a single complex trait locus. In this way, multiple independent transgene integrations can be generated within a genomic window to create a complex trait locus. As used herein, a "complex trait locus" (plural: "complex trait loci") is a chromosomal segment within a defined genomic window that comprises at least one transgenic target site and at least one genomic locus of interest, wherein the target site and the genomic locus of interest have different genomic insertion sites within the defined genomic window. The complex trait locus is designed such that the transgenic target sites and/or genomic loci of interest can segregate independently of each other during meiosis. This allows traits to be bred in and bred out of the complex trait locus. Thus, the methods described herein provide the benefit of being able to alter a complex trait locus by breeding in and breeding away specific elements of the complex trait locus. A variety of methods can also be employed to further modify the transgenic target sites and/or genomic loci of interest such that they contain a variety of polynucleotides of interest.

II. Compositions

A. Genomic Window

Provided herein is a plant or seed having in its genome a genomic window. As used herein, a "genomic window" is a segment of a chromosome in the genome of a plant that is desirable for producing a complex trait locus or the segment of a chromosome comprising a complex trait locus that was produced by the methods provided herein. The genomic window can include, for example, one or more traits prior to producing a complex transgenic trait locus therein. As used herein, a "trait" refers to the phenotype conferred from a particular gene or grouping of genes.

The genomic window can be about 1, 2, 3, 4, 5, 6, 7, 8, 9, 10, 11, 12, 13, 14, 15 or more centimorgans (cM) in length. Alternatively, the genomic window can be about 1-cM, about 2-8 cM, about 2-5 cM, about 3-10 cM, about 3-6 cM, about 4-10 cM, about 4-7 cM, about 5-10 cM, about 5-8 cM, about 6-10 cM, about 6-9 cM, about 7-10 cM, about 8-10 cM or about 9-10 cM in length. In one embodiment, the genomic window is about 10 centimorgans (cM) in length or about 5 cM in length. A "centimorgan" (cM) or "map unit" is the distance between two linked genes, markers, target sites, genomic loci of interest, loci, or any pair thereof, wherein 1% of the products of meiosis are recombinant. Thus, a centimorgan is equivalent to a distance equal to a 1% average recombination frequency between the two linked genes, markers, target sites, loci, genomic loci of interest or any pair thereof.

The genomic window can comprise various components. Such components can include, for example, transgenic target sites, native genes, genomic loci of interest, recombination sites and polynucleotides of interest. The genomic window can comprise at least 1, 2, 3, 4, 5, 6, 7, 8, 9, 10 or more transgenic target sites such that each transgenic target site has a different genomic insertion site within the genomic window. In addition, the genomic window can comprise at least 1, 2, 3, 4, 5, 6, 7, 8, 9, 10 or more genomic loci of interest each having a different genomic insertion site. By a "different genomic insertion site" is meant that each component of the genomic window (i.e. transgenic target sites and genomic loci of interest) is inserted into the genome at a different location and as such each component can segregate independently from one another. For example, the genomic window can comprise a combination of transgenic target sites and/or genomic loci of interest such that each target site or genomic loci of interest has a different genomic insertion site within the genomic window.

The components of the genomic windows provided herein have different genomic insertion sites and as such can segregate independently from one another. As used herein, "segregate independently", is used to refer to the genetic separation of any two or more genes, transgenes, native genes, mutated genes, target sites, genomic loci of interest, markers and the like from one another during meiosis. Assays to measure whether two genetic elements segregate independently are known in the art. As such, any two or more genes, transgenes, native genes, mutated genes, target sites, genomic loci of interest, markers and the like within a genomic window provided herein, have genomic insertion sites located at an appropriate distance from one another so that they generally segregate independently at a rate of about 10% or less. Thus, the components of the genomic windows provided herein can segregate independently from one another at a rate of about 10%, 9%, 8%, 7%, 6%, 5%, 4%, 3%, 2%, 1%, 0.9%, 0.8%, 0.7%, 0.6%, 0.5%, 0.4%, 0.3%, 0.2% or 0.1%. Alternatively, the components of the genomic windows provided herein can segregate independently from one another at a rate of about 10-0.1%, about 10-0.5%, about 10-1%, about 10-5%, about 9-0.1%, about 9-0.5%, about 9-1%, about 9-5%, about 8-0.1%, about 8-0.5%, about 8-1%, about 8-4%, about 7-0.1%, about 7-0.5%, about 7-1%, about 7-4%, about 6-0.1%, about 6-1%, about 6-0.5%, about 6-3%, about 5-0.1%, about 5-1%, about 5-0.5%, about 4-0.1%, about 4-1%, about 4-0.5%, about 3-0.1%, about 3-1%, about 3-0.5%, about 2-0.1%, about 2-0.5%, about 1-0.1% or about 1-0.5%. For example, if the genomic window comprises a transgenic target site and a genomic locus of interest that are about 5 cM from each other, the transgenic target site and the genomic locus of interest would segregate independently at a rate of about 5%.

In one embodiment, the genomic window comprises at least a first transgenic target site, a second transgenic target site, and at least one genomic locus of interest wherein each of the transgenic target sites and genomic loci of interest have a different genomic insertion site and segregate independently from one another at a rate of about 10% to about 0.1%.

Any given genomic window can also comprise at least one altered target sequence that originated from a corresponding target sequence that was recognized and cleaved by a double-strand break-inducing agent. As used herein, a "double-strand-break-inducing agent" refers to any nuclease which produces a double-strand break in the target sequence. A "target sequence" refers to a polynucleotide sequence in the genome of a plant cell that comprises a recognition sequence for a double-strand-break-inducing agent at which a double-strand-break is induced. An "altered target sequence" refers to a target sequence comprising at least one alteration when compared to a non-altered target sequence. "Alterations" can include, for example: (i) replacement of at least one nucleotide, (ii) a deletion of at least one nucleotide, (iii) an insertion of at least one nucleotide, or (iv) any combination of (i)-(iii). As such, insertion sites for the various components of the genomic window (i.e. transgenic target sites or genomic loci of interest) can be created in any given genomic window. Methods of creating altered target sequences are known and are disclosed in U.S. Provisional Application No. 61/466,602, filed on Mar. 23, 2011, which is herein incorporated by reference in its entirety.

In specific embodiments, the genomic window is flanked by at least a first marker and a second marker. Non-limiting examples of such markers on chromosome 1 of corn include, for example, UMC1160, UMC2224, NP1579B, PMCB1, IDP3917, GPM199C, IDP1425, MMP68, UMC2225, STD2C(DBA), TIDP3300, CSU1171, SUT1, UMC1166, AY107207, UMC1568, IDP3783, BNLG1429, IDP209, LTK1 and IDP7169. Table 2 depicts the public IBM2 genetic map positions for markers on chromosome 1 of corn. Non-limiting examples of markers on chromosome 6 of corn include, for example, UMC1625, UMC2196, UMC2312, BNLG1867, PZA03047, UMC1229, UCK1, RZ390D (CYB5), MMP20, MMP10, MMP160, PHP20528, UMC2314, UAZ232B(SCI), UMC2313, CDO545, PHP20854, UMC1133, UFG69, MMP76, Y1, BNLG1422, MMP108B, MMP4, UMC1006 and RZ444E. Table 6 A depicts the public IBM2 genetic map positions for markers on chromosome 6 of corn. Non-limiting examples of such markers on chromosome 19 of soybean include, for example, SATT613, SATT284, S60414-TB, SATT462, SATT481, SATT156 and SCT_010. Table 11 depicts the public genetic map positions for markers on chromosome 19 of soybean.

B. Components of the Genomic Window i. Transgenic Target Sites and Methods of Altering A transgenic target site can comprise various components. As used herein, by "target site" is intended a polynucleotide comprising a nucleotide sequence comprising at least one recombination site. By "transgenic target site" is meant a target site that is non-native either in sequence and/or in genomic location to the plant genome. In some embodiments, the transgenic target site can comprise at least 1, 2, 3, 4, 5, 6 or more recombination sites for site-specific recombination. In one embodiment, the transgenic target site comprises a first recombination site and a second recombination site. In such embodiments, the first and second recombination sites may be dissimilar with respect to one another or may be dissimilar and have a decreased compatibility with respect to one another. Such first and second recombination sites are able to recombine with their corresponding or identical recombination site when provided with the appropriate recombinase.

One or more intervening sequences may be present between the recombination sites of the target site. Intervening sequences of particular interest would include linkers, adapters, selectable markers, polynucleotides of interest, other recombination sites, promoters and/or other sites that aid in vector construction or analysis. Various polynucleotides of interest then could be employed between the recombination sites. Methods of altering the target sites are discussed in greater detail elsewhere herein. In addition, the recombination sites of the target site can be located in various positions, including, for example, within intronic sequences, coding sequences, or untranslated regions.

The recombination sites employed in the methods and compositions provided herein can be "corresponding" sites or "dissimilar" sites. By "corresponding recombination sites" or a "set of corresponding recombination sites" is intended that the recombination sites have the same or corresponding nucleotide sequence. A set of corresponding recombination sites, in the presence of the appropriate recombinase, will efficiently recombine with one another (i.e., the corresponding recombination sites are recombinogenic).

In other embodiments, the recombination sites are dissimilar. By "dissimilar recombination sites" or a "set of dissimilar recombination sites" is intended that the recombination sites are distinct (i.e., have at least one nucleotide difference).

The recombination sites within "a set of dissimilar recombination sites" can be either recombinogenic with respect to one another or have a decreased compatibility with respect to one other. By "recombinogenic" is intended that the set of recombination sites are capable of recombining with one another.

In other embodiments, a set of dissimilar recombination sites can comprise sets of recombination sites having a decreased compatibility with respect to one another. By "decreased compatibility" is intended the set of recombination sites, in the presence of the appropriate recombinase, will have a decreased efficiency of recombination compared to that seen with their cognate site. In some embodiments, having a decrease in compatibility will result in no recombination between the sites. In other embodiments, having a decrease in compatibility will result in a minimal level of recombination between the sites. Thus, suitable recombination sites having a decrease in compatibility with one another for use in the methods and compositions provided herein include those sites that recombine (or excise) with one another at a frequency lower than 90%, 80%, 70%, 60%, 50%, 40%, 30%, 20%, 15%, 10%, 5%, 4%, or 3%. In some embodiments the recombination sites having a decrease in compatibility with one another recombine (or excise) with one another at a frequency lower than the detectable limit under standard conditions in an excision assay, lower than 2%, 1.5%, 1%, 0.75%, 0.5%, 0.25%, 0.1%, 0.075, 0.005%, 0.001%. Each recombination site within the "set of dissimilar-recombination sites" is biologically active and therefore can recombine with an identical site.

In some embodiments, the genomic window comprises a first transgenic target site comprising a first and a second recombination site that are dissimilar with respect to one another and a second transgenic target site comprising a third and a fourth recombination site that are dissimilar with respect to one another. In other embodiments, the genomic window comprises a first transgenic target site comprising a first and a second recombination site that are dissimilar and have a decreased compatibility with respect to one another and a second transgenic target site comprising a third and a fourth recombination site that are dissimilar and have a decreased compatibility with respect to one another. In some cases, the first transgenic target site and the second transgenic target site segregate independently from one another at a rate of about 5% to about 0.1%. Thus, any of the various target sites provided herein can segregate independently from one another at a rate of about 10-0.1%, about 10-0.5%, about 10-1%, about 10-5%, about 9-0.1%, about 9-0.5%, about 9-1%, about 9-5%, about 8-0.1%, about 8-0.5%, about 8-1%, about 8-4%, about 7-0.1%, about 7-0.5%, about 7-1%, about 7-4%, about 6-0.1%, about 6-0.5%, about 6-1%, about 6-3%, about 5-0.1%, about 5-0.5%, about 5-1%, about 4-0.1%, about 4-0.5%, about 4-1%, about 3-0.1%, about 3-0.5%, about 3-1%, about 2-0.1%, about 2-0.5%, about 1-0.1% or about 1-0.5%. The various target sites provided herein can be about 0.1, 0.2, 0.3, 0.4, 0.5, 0.6, 0.7, 0.8, 0.9, 1, 2, 3, 4, 5, 6, 7, 8, 9, 10 cM or more from one another in the genomic window. Alternatively, the various target sites can be about 0.5-10 cM, about 1-10 cM, about 2-10 cM, about 2-5 cM, about 3-10 cM, about 3-6 cM, about 4-10 cM, about 4-7 cM, about 5-10 cM, about 5-8 cM, about 6-10 cM, about 6-9 cM, about 7-10 cM, about 8-10 cM, about 9-10 cM, about 0.1-0.5 cM, about 0.1-1 cM, about 0.1-2 cM, about 0.1-3 cM, about 0.1-4 cM, about 0.1-5 cM, about 0.1-6 cM, about 0.1-7 cM about 0.1-8 cM, about 0.1-9 cM or about 0.1-10 cM from one another in the genomic window.

In a specific embodiment, the recombination sites of the second transgenic target site are different from the dissimilar sites of the first transgenic target site. Alternatively, the second transgenic target site can comprise the same dissimilar sites as the first transgenic target site. In a further embodiment, the genomic window comprises a third transgenic target site comprising a fifth and a sixth recombination site that are dissimilar with respect to one another. In yet a further embodiment, the genomic window comprises a third transgenic target site comprising a fifth and sixth recombination sites that are dissimilar and have a decreased compatibility with respect to one another. In all such cases, the first, second and third transgenic target sites have different genomic insertion sites.

Various recombination sites can be employed in the methods and compositions provided herein (i.e. in the various transgenic target sites or genomic loci of interest disclosed herein). By "recombination site" is intended a recombination site and active variants thereof. Many recombination systems are known in the art and one of skill will recognize the appropriate recombination site to be used with the recombination system of interest. As discussed in greater detail elsewhere herein, various combinations of recombination sites can be employed including, sets of dissimilar sites and corresponding recombination sites and/or dissimilar recombination sites and/or sites that are dissimilar and have a decreased compatibility with respect to one another can be used in the various methods and compositions provided herein. Accordingly, any suitable recombination site or set of recombination sites may be utilized herein, including a FRT site, a biologically active variant of a FRT site (i.e. a mutant FRT site), a LOX site, a biologically active variant of a LOX site (i.e. a mutant LOX site), any combination thereof, or any other combination of recombination sites known in the art. Examples of FRT sites include, for example, the wild type FRT site (FRT1) (SEQ ID NO: 1), and various mutant FRT sites, including but not limited to, FRT5 (SEQ ID NO: 2), FRT6 (SEQ ID NO: 3), FRT7 (SEQ ID NO: 4), FRT12 (SEQ ID NO: 5) and FRT87 (SEQ ID NO: 6). See, for example, U.S. Pat. No. 6,187,994. See also, US Publication No. 2011-0047655, herein incorporated by reference.

Recombination sites from the Cre/Lox site-specific recombination system can also be used. Such recombination sites include, for example, wild type LOX sites and mutant LOX sites. An analysis of the recombination activity of mutant LOX sites is presented in Lee et al. (1998) *Gene* 216:55-65, herein incorporated by reference. Also, see for example, Schlake and Bode (1994) *Biochemistry* 33:12746-12751; Huang et al. (1991) *Nucleic Acids Research* 19:443-448; Sadowski (1995) In *Progress in Nucleic Acid Research and Molecular Biology* Vol. 51, pp. 53-91; Cox (1989) In *Mobile DNA*, Berg and Howe (eds) American Society of Microbiology, Washington D.C., pp. 116-670; Dixon et al. (1995) *Mol. Microbiol.* 18:449-458; Umlauf and Cox (1988) *EMBO* 7:1845-1852; Buchholz et al. (1996) *Nucleic Acids Research* 24:3118-3119; Kilby et al. (1993) *Trends Genet.* 9:413-421; Rossant and Geagy (1995) *Nat. Med.* 1: 592-594; Albert et al. (1995) *The Plant* 7:649-659; Bayley et al. (1992) *Plant Mol. Biol.* 18:353-361; Odell et al. (1990) *Mol. Gen. Genet.* 223:369-378; Dale and Ow (1991) *Proc. Natl. Acad. Sci. USA* 88:10558-10562; Qui et al. (1994) *Proc. Natl. Acad. Sci. USA* 91:1706-1710; Stuurman et al. (1996) *Plant Mol. Biol.* 32:901-913; Dale et al. (1990) *Gene* 91:79-85; Albert et al. (1995) *The Plant J* 7:649-659 and WO 01/00158; all of which are herein incorporated by reference.

In a specific embodiment, at least one of the first and the second recombination sites comprises FRT1 (SEQ ID NO: 1), FRT5 (SEQ ID NO: 2), FRT6 (SEQ ID NO: 3), FRT7 (SEQ ID NO: 4), FRT12 (SEQ ID NO: 5) or FRT87 (SEQ ID NO: 6). In a specific embodiment, the first and the second recombination sites of the target site comprise a FRT1 site and a FRT87 site.

Active variants and fragments of recombination sites (i.e. SEQ ID NOS: 1-6) are also encompassed by the compositions and methods provided herein. Fragments of a recombination site retain the biological activity of the recombination site and hence facilitate a recombination event in the presence of the appropriate recombinase. Thus, fragments of a recombination site may range from at least about 5, 10, 15, 20, 25, 30, 35, nucleotides, and up to the full-length of a recombination site. Active variants can comprise at least 65%, 70%, 75%, 80%, 85%, 90%, 91%, 92%, 93%, 94%, 95%, 96%, 97%, 98%, 99% or more sequence identity to the native recombination site, wherein the active variants retain biological activity and hence facilitate a recombination event in the presence of the appropriate recombinase. Assays to measure the biological activity of recombination sites are known in the art. See, for example, Senecoll et al. (1988) *J. Mol. Biol.* 201:406-421; Voziyanov et al. (2002) *Nucleic Acid Research* 30:7, U.S. Pat. No. 6,187,994, WO/01/00158, and Albert et al. (1995) *The Plant Journal* 7:649-659.

Recombinases are also employed in the methods and compositions provided herein. By "recombinase" is intended a native polypeptide that catalyzes site-specific recombination between compatible recombination sites. For reviews of site-specific recombinases, see Sauer (1994) *Current Opinion in Biotechnology* 5:521-527; and Sadowski (1993) *FASEB* 7:760-767; the contents of which are incorporated herein by reference. The recombinase used in the methods can be a naturally occurring recombinase or a biologically active fragment or variant of the recombinase. Recombinases useful in the methods and compositions include recombinases from the Integrase and Resolvase families, biologically active variants and fragments thereof, and any other naturally occurring or recombinantly produced enzyme or variant thereof that catalyzes conservative site-specific recombination between specified DNA recombination sites.

The Integrase family of recombinases has over one hundred members and includes, for example, FLP, Cre, Int, and R. For other members of the Integrase family, see for example, Esposito et al. (1997) *Nucleic Acid Research* 25:3605-3614 and Abremski et al. (1992) *Protein Engineering* 5:87-91, both of which are herein incorporated by reference. Other recombination systems include, for example, the streptomycete bacteriophage phi C31 (Kuhstoss et al. (1991) *J. Mol. Biol.* 20:897-908); the SSV1 site-specific recombination system from *Sulfolobus shibatae* (Maskhelishvili et al. (1993) *Mol. Gen. Genet.* 237:334-342); and a retroviral integrase-based integration system (Tanaka et al. (1998) *Gene* 17:67-76). In other embodiments, the recombinase is one that does not require cofactors or a supercoiled substrate. Such recombinases include Cre (SEQ ID NO: 7), FLP (SEQ ID NO: 8), or active variants or fragments thereof (SEQ ID NOS: 9 and 10).

The FLP recombinase is a protein that catalyzes a site-specific reaction that is involved in amplifying the copy number of the two-micron plasmid of *S. cerevisiae* during DNA replication. As used herein, FLP recombinase refers to a recombinase that catalyzes site-specific recombination between two FRT sites. The FLP protein has been cloned and expressed. See, for example, Cox (1993) *Proc. Natl. Acad. Sci. U.S.A.* 80:4223-4227. The FLP recombinase for use in the methods and with the compositions may be derived from the genus *Saccharomyces*. One can also synthesize a polynucleotide comprising the recombinase using plant-preferred codons for optimal expression in a plant of interest. A recombinant FLP enzyme encoded by a nucleotide sequence comprising maize preferred codons (FLPm) (SEQ ID NO: 10) that catalyzes site-specific recombination events is known. See, for example, U.S. Pat. No. 5,929,301, herein incorporated by reference. Additional functional variants and fragments of FLP are known. See, for example, Buchholz et al. (1998) *Nat. Biotechnol.* 16:617-618, Hartung et al. (1998) *J. Biol. Chem.* 273:22884-22891, Saxena et al. (1997) *Biochim Biophys Acta* 1340(2):187-204, and Hartley et al. (1980) *Nature* 286:860-864, all of which are herein incorporated by reference.

The bacteriophage recombinase Cre catalyzes site-specific recombination between two lox sites. The Cre recombinase is known in the art. See, for example, Guo et al. (1997) *Nature* 389:40-46; Abremski et al. (1984) *J. Biol. Chem.* 259:1509-1514; Chen et al. (1996) *Somat. Cell Mol. Genet.* 22:477-488; Shaikh et al. (1977) *J. Biol. Chem.* 272:5695-5702; and, Buchholz et al. (1998) *Nat. Biotechnol.* 16:617-618, all of which are herein incorporated by reference. The Cre polynucleotide sequences may also be synthesized using plant-preferred codons. Such sequences (moCre) are described in WO 99/25840, herein incorporated by reference and set forth in SEQ ID NO: 9.

It is further recognized that a chimeric recombinase can be used in the methods. By "chimeric recombinase" is intended a recombinant fusion protein which is capable of catalyzing site-specific recombination between recombination sites that originate from different recombination systems. That is, if a set of functional recombination sites, characterized as being dissimilar with respect to one another, is utilized in the methods and compositions and comprises a FRT site and a LoxP site, a chimeric FLP/Cre recombinase or active variant or fragment thereof will be needed or, alternatively, both recombinases may be separately provided. Methods for the production and use of such chimeric recombinases or active variants or fragments thereof are described in WO 99/25840, herein incorporated by reference.

By utilizing various combinations of recombination sites in the transgenic target sites provided herein, the methods provide a mechanism for the site-specific integration of polynucleotides of interest into a specific site in the plant genome. The methods also allow for the subsequent insertion of additional polynucleotides of interest into the specific genomic site.

As used herein, by "providing" is intended any method that allows for an amino acid sequence and/or a polynucleotide to be brought together with the recited components. A variety of methods are known in the art for the introduction of nucleotide sequence into a plant. Any means can be used to bring together the various components of the recombination system (i.e., the transgenic target site and the appropriate recombinase), including, for example, transformation and sexual crossing. See, also, WO99/25884 herein incorporated by reference. In addition, the recombinase may be provided by the introduction of the polypeptide or mRNA into the cell.

Active variants and fragments of recombinases (i.e. FLP or Cre) are also encompassed by the compositions and methods provided herein. Such active variants can comprise at least 65%, 70%, 75%, 80%, 85%, 90%, 91%, 92%, 93%, 94%, 95%, 96%, 97%, 98%, 99% or more sequence identity to the native recombinase, wherein the active variants retain biological activity and hence implement a recombination event. Assays for recombinase activity are known and generally measure the overall activity of the enzyme on DNA substrates containing recombination sites. For example, to assay for FLP activity, inversion of a DNA sequence in a circular plasmid containing two inverted FRT sites can be detected as a change in position of restriction enzyme sites. This assay is described in Vetter et al. (1983) *PNAS* 80:7284. Alternatively, excision of DNA from a linear molecule or intermolecular recombination frequency induced by the enzyme may be assayed, as described, for example, in Babineau et al. (1985) *Journal of Biological Chemistry* 260:12313; Meyer-Leon et al. (1987) *Nucleic Acid Res* 15:6469; and Gronostaj ski et al. (1985) *Journal of Biological Chemistry* 260:12328. Alternatively, recombinase activity may also be assayed by excision of a sequence flanked by recombinogenic FRT sites that upon removal will activate an assayable marker gene.

ii. Genomic Locus of Interest

As used herein, a "genomic locus of interest" comprises a collection of specific polymorphisms that are inherited together. A given genomic locus can comprise, but is not limited to, a transgene, a native gene or an additional transgenic target site that can comprise dissimilar pairs of recombination sites or pairs of recombination sites that are dissimilar and have a decreased compatibility with respect to one another.

The genomic locus of interest can be, for example, any modification that confers a trait, such as a transgene or a native trait. In one embodiment, the genomic locus of interest comprises a native trait. As used herein, a "native trait" refers to a trait found in nature. In another embodiment, the genomic locus of interest comprises a transgene.

The number of genomic loci of interest that could be crossed into a genomic window of a plant is at least 1, 2, 3, 4, 5, 6, 7, 8, 9, 10 or more. Any desired trait can be introduced into the genome at a given genomic locus of interest. Such traits include, but are not limited to, traits conferring insect resistance, disease resistance, herbicide tolerance, male sterility, abiotic stress tolerance, altered phosphorus, altered antioxidants, altered fatty acids, altered essential amino acids, altered carbohydrates, or sequences involved in site-specific recombination.

In specific embodiments, a given genomic locus of interest is associated with a desirable and/or favorable phenotype in a plant. For example, traits that confer insect resistance, disease resistance or herbicide tolerance would be desirable in a plant. In other embodiments, the genomic locus is not associated with traits that affect the agronomic characteristics of the plant.

A given genomic locus of interest has its own genomic insertion site within the genomic window. For example, a genomic locus of interest and a transgenic target site within the genomic window will have different genomic insertion sites within the genome. A given transgenic target site can be found within about 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, or 0.1 cM from the genomic locus of interest such that the target site and genomic locus of interest have different genomic insertion sites. Alternatively, a given transgenic target site can be found within about 0.5-10 cM, about 1-10 cM, about 2-10 cM, about 2-5 cM, about 3-10 cM, about 3-6 cM, about 4-10 cM, about 4-7 cM, about 5-10 cM, about 5-8 cM, about 6-10 cM, about 6-9 cM, about 7-10 cM, about 8-10 cM, about 9-10 cM, about 0.1-0.5 cM, about 0.1-1 cM, about 0.1-2 cM, about 0.1-3 cM, about 0.1-4 cM, about 0.1-5 cM, about 0.1-6 cM, about 0.1-7 cM about 0.1-8 cM, about 0.1-9 cM or about 0.1-10 cM from the genomic locus of interest such that the target site and genomic locus of interest have different genomic insertion sites. In a specific embodiment, a first transgenic target site or a second transgenic target site is found within about 5 cM from the genomic locus of interest. In yet another embodiment, the first or second transgenic target site is found within 2 cM or 1 cM from the genomic locus of interest. In such cases where the genomic window comprises a third transgenic target site, the third transgenic target site can be found within about 5 cM from the genomic locus of interest.

In some embodiments, the first transgenic target site and the second transgenic target site segregate independently from the genomic locus of interest at a rate of about 5%, 4%, 3%, 2%, 1%, 0.9%, 0.8%, 0.7%, 0.6%, 0.5%, 0.4%, 0.3%, 0.2% or 0.1%. Alternatively, the first transgenic target site and the second transgenic target site segregate independently from the genomic locus of interest at a rate of about 5-0.1%, about 5-1%, about 5-0.5%, about 4-0.1%, about 4-0.5%, about 4-1%, about 3-0.1%, about 3-0.5%, about 3-1%, about 2-0.1%, about 2-0.5%, about 1-0.1% or about 1-0.5%.

C. Polynucleotides of Interest

Any polynucleotide of interest (i.e., the "polypeptide of interest" or "gene of interest") may be provided to the plant cells in the transgenic target sites or genomic loci of interest of the methods and compositions disclosed herein either by transformation methods or breeding methods discussed elsewhere herein. It is recognized that any polynucleotide of interest can be provided, integrated into the plant genome within a genomic window and expressed in a plant. The polynucleotide of interest or gene of interest can comprise, for example, a transgene or a native gene. The methods disclosed herein, provide for at least 1, 2, 3, 4, 5, 6, 7, 8, 9, 10 or more polynucleotides of interest to be integrated into a genomic window.

Various changes in phenotype are of interest, including modifying the fatty acid composition in a plant, altering the amino acid content of a plant, altering a plant's pathogen defense mechanism, and the like. These results can be achieved by providing expression of heterologous products (i.e. polynucleotides of interest) or increased expression of endogenous products in plants. Alternatively, the results can be achieved by providing for a reduction of expression of one or more endogenous products, particularly enzymes or cofactors in the plant. These changes result in a change in phenotype of the transformed plant.

Polynucleotides of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Polynucleotides/polypeptides of interest include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. More specific polynucleotides of interest include, but are not limited to, genes that improve crop yield, polypeptides that improve desirability of crops, genes that alter phosphorus content, such as a phytase-encoding gene, genes that alter antioxidant content or composition, such as those that alter tocopherol and tocotrienol content, genes that alter carbohydrates, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms.

Polynucleotides of interest can also be genes that create a site for site-specific DNA integration. This includes the introduction of FRT sites that may be used in the FLP/FRT system and/or LOX sites that may be used in the Cre/LoxP system. These systems and others are described in detail elsewhere herein.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g., the HPPD gene) or other such genes known in the art. See, for example, U.S. Pat. Nos. 7,626,077, 5,310,667, 5,866,775, 6,225,114, 6,248,876, 7,169,970, 6,867,293, and U.S. Provisional Application No. 61/401,456, each of which is herein incorporated by reference.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) Eur. J. Biochem. 165:99-106, the disclosures of which are herein incorporated by reference.

Commercial traits can also be encoded on a polynucleotide of interest that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) J. Bacteriol. 170:5837-5847) facilitate expression of polyhydroxyalkanoates (PHAs).

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Illinois), pp. 497-502; herein incorporated by reference); corn (Pedersen et al. (1986) J. Biol. Chem. 261:6279; Kirihara et al. (1988) Gene 71:359; both of which are herein incorporated by reference); and rice (Musumura et al. (1989) Plant Mol. Biol. 12:123, herein incorporated by reference). Other agronomically important genes encode latex, Floury 2, growth factors, seed storage factors, and transcription factors.

Polynucleotides that improve crop yield include dwarfing genes, such as Rht1 and Rht2 (Peng et al. (1999) Nature 400:256-261), and those that increase plant growth, such as ammonium-inducible glutamate dehydrogenase. Polynucleotides that improve desirability of crops include, for example, those that allow plants to have reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from *E. coli* and bears the GenBank accession number M96268. See, U.S. Pat. No. 7,361,811, herein incorporated by reference.

The polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

Active variants or fragments of polynucleotides/polypeptides of interest are also provided. Such active variants can comprise at least 65%, 70%, 75%, 80%, 85%, 90%, 91%, 92%, 93%, 94%, 95%, 96%, 97%, 98%, 99% or more sequence identity to the native polynucleotide/polypeptide of interest, wherein the active variants retain the biological activity of the native polynucleotide/polypeptide.

D. Plants

Plants, plant cells, or seeds having in their genome a genomic window provided herein are also encompassed. Plants, plant cells or seeds comprising at least one complex trait locus are also provided. The genomic window and complex trait loci of the plants, plant cells or seeds can comprise any combination of any of the various transgenic target sites, genomic loci of interest or polynucleotides of interest described herein.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included herein, provided that these parts comprise the recited DNA construct.

A transformed plant or transformed plant cell provided herein is one in which genetic alteration, such as transformation, has been affected as to a gene of interest, or is a plant or plant cell which is descended from a plant or cell so altered and which comprises the alteration. A "transgene" is a gene that has been introduced into the genome by a transformation procedure. Accordingly, a "transgenic plant" is a plant that contains a transgene, whether the transgene was introduced into that particular plant by transformation or by breeding; thus, descendants of an originally-transformed plant are encompassed by the definition. A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which does not express the transgene, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the transgene; or (e) the subject plant or plant cell itself, under conditions in which the construct is not expressed.

Plant cells that have been transformed to have any of the various components provided herein (i.e. transgenic target sites, genomic loci of interest, site-specific recombinases, recombination sites, polynucleotides of interest or any active variants or fragments thereof) can be grown into whole plants. The regeneration, development, and cultivation of plants from single plant protoplast transformants or from various transformed explants is well known in the art. See, for example, McCormick et al. (1986) *Plant Cell Reports* 5:81-84; Weissbach and Weissbach, In: Methods for Plant Molecular Biology, (Eds.), Academic Press, Inc. San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. Two or more generations may be grown to ensure that expression of the desired phenotypic characteristic is stably maintained and inherited and then seeds harvested to ensure expression of the desired phenotypic characteristic has been achieved. In this manner, the compositions presented herein provide transformed seed (also referred to as "transgenic seed") having a polynucleotide provided herein, for example, a transgenic target site, stably incorporated into their genome.

The various components provided herein (i.e. transgenic target sites, genomic loci of interest, site-specific recombinases, recombination sites, polynucleotides of interest or any active variants or fragments thereof) may be used for transformation of any plant species, including, but not limited to, monocots and dicots. Examples of plant species of interest include, but are not limited to, corn (maize) (*Zea mays*), *Brassica* sp. (e.g., *B. napus, B. raga, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (Macadamia *integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus* rosasanensis), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*.

Conifers that may be employed include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

It is recognized that the plant having stably incorporated the DNA construct can be further characterized for site-specific integration potential, agronomic potential, and copy number. See, U.S. Pat. No. 6,187,994.

Depending on the polynucleotide(s) of interest incorporated into the genomic window, the transgenic plants, plant cells, or seeds comprising a polynucleotide(s) of interest provided herein may have a change in phenotype, including, but not limited to, an altered pathogen or insect defense mechanism, an increased resistance to one or more herbicides, an increased ability to withstand stressful environmental conditions, a modified ability to produce starch, a modified level of starch production, a altered oil content and/or composition, a altered carbohydrate content and/or composition, a altered fatty acid content and/or composition, a altered phosphorus content and/or composition, a altered antioxidant content and/or composition, a modified ability to utilize, partition and/or store nitrogen, and the like.

III. Methods of Creating and Altering a Complex Trait Locus
A. Forming a Complex Trait Locus The components of a genomic window, (i.e. transgenic target sites and/or genomic loci of interest) can be brought together by various methods. One such method is by crossing plants comprising various target sites and/or genomic loci of interest having in a given genomic window different genomic insertion sites and selecting for plants having undergone a recombination event such that the desired combination of transgenic target sites and/or genomic loci of interest are present in the same plant. Such breeding techniques can thereby be employed to create a complex trait locus in a plant.

As used herein, "breeding" is the genetic manipulation of living organisms. Plants are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. In a breeding application, a breeder initially selects and crosses two or more parental plants. As used herein, "crossing" can refer to a simple X by Y cross, or the process of backcrossing, depending on the context.

Methods are provided herein to either establish a complex trait locus or to break the complex trait locus apart using breeding techniques. For example, a first plant comprising a first transgenic target site within a genomic window, and the first plant does not comprise a first genomic locus of interest, could be crossed with a second plant comprising the first genomic locus of interest within the same genomic window and the second plant does not comprise said first transgenic target site within the genomic window. A progeny plant is then selected comprising both the first transgenic target site and the first genomic locus of interest within the genomic window. Selecting a progeny plant comprising both the target site and the genomic locus of interest can be done through various methods. For example, a phenotypic analysis can be performed whereby the activity of a marker or an introduced sequence is detected in the progeny plant. Alternative methods that assay for markers which are specific to the genomic locus of interest and the target site include techniques such as PCR, hybridization, Isozyme electrophoresis, Restriction Fragment Length Polymorphisms (RFLPs), Randomly Amplified Polymorphic DNAs (RAPDs), Arbitrarily Primed PCR (AP-PCR), DNA Amplification Fingerprinting (DAF), Sequence Characterized Amplified Regions (SCARs), Amplified Fragment length Polymorphisms (AFLPs), Simple Sequence Repeats (SSRs), and Single Nucleotide Polymorphisms (SNPs).

In non-limiting embodiments, the complex trait locus can comprise (1) a transgenic target site and a genomic locus of interest having different genomic insertion sites in said genomic window; (2) 2 transgenic target sites and a genomic locus of interest having different genomic insertion sites in said genomic window; (3) 2 transgenic target sites and 2 genomic loci of interest having different genomic insertion sites in said genomic window; (4) a genomic locus of interest and a target site comprising one or more polynucleotides of interest wherein said genomic locus of interest and transgenic target site have different genomic insertion sites; (5) a transgenic target site and a genomic locus of interest comprising a transgene, each having a different genomic insertion site; (6) a transgenic target site and a genomic locus of interest comprising a native trait, each having a different genomic insertion site; (7) a transgenic target site comprising a first and a second dissimilar recombination sites and a genomic locus of interest, each having a different genomic insertion site; (8) a genomic locus of interest, a first transgenic target site comprising a first and a second dissimilar recombination sites and a second transgenic target site comprising a third and a fourth dissimilar recombination sites, wherein each of said genomic locus of interest, first transgenic target site and second transgenic target site has a different genomic insertion site; (9) a genomic locus of interest, a first transgenic target site comprising a first and a second dissimilar recombination sites, a second transgenic target site comprising a third and a fourth dissimilar recombination sites and a third transgenic target site comprising a fifth and a sixth dissimilar recombination sites, wherein each of said genomic locus of interest, first transgenic target site, second transgenic target site and third transgenic target site has a different genomic insertion site; (10) a first transgenic target site and a second transgenic target site wherein the second transgenic target site comprises different dissimilar recombination sites as the first transgenic target site and a genomic locus of interest, each having a different genomic insertion site; (11) a first transgenic target site, a second transgenic target site wherein the second transgenic target site comprises the same dissimilar recombination sites as the first transgenic target site, and a genomic locus of interest, each having a different genomic insertion site; (12) a first transgenic target site, a second transgenic target site wherein the dissimilar recombination sites comprise a FRT site or a mutant FRT site, and a genomic locus of interest, each having a different genomic insertion site; (13) a first transgenic target site and a second transgenic target site wherein the dissimilar recombination sites comprise a FRT5, a FRT6, a FRT7, a FRT12, or a FRT87 site, and a genomic locus of interest, each having a different genomic insertion site; or (14) a first transgenic target site and a second transgenic target site wherein the dissimilar recombination sites comprise a FRT1 and a FRT87 site, and a genomic locus of interest, each having a different genomic integration site.

A complex trait locus comprising multiple target sites, genomic loci of interest and/or polynucleotides of interest can be produced within a genomic window in the genome of a plant. FIG. 1 provides a non-limiting example of how two traits can be stacked into the genome at a genetic distance of, for example, 5 cM from each other. A first plant comprising a first transgenic target site within the genomic window and not having the first genomic locus of interest is crossed to a second transgenic plant, comprising a genomic locus of interest at a different genomic insertion site within the genomic window and the second plant does not comprise the first transgenic target site. About 5% of the plant progeny from this cross will have both the first transgenic target site and the first genomic locus of interest integrated at different genomic insertion sites within the genomic window. Progeny plants having both sites in the defined genomic window can be further crossed with a third transgenic plant comprising a second transgenic target site and/or a second genomic locus of interest within the defined genomic window and lacking the first transgenic target site and the first genomic locus of interest. Progeny are then selected having the first transgenic target site, the first genomic locus of interest and the second genomic locus of interest integrated at different genomic insertion sites within the genomic window. Such methods can be used to produce a transgenic plant comprising a complex trait locus having at least 1, 2, 3, 4, 5, 6, 7, 8, 9, 10 or more transgenic target sites and/or genomic loci of interest integrated at different sites within the genomic window. In such a manner, various complex trait loci can be generated.

In one non-limiting embodiment, a method of producing a complex trait locus in the genome of a plant comprises providing a first plant having within a genomic window of about 10 cM in length at least a first transgenic target site and does not comprise a first genomic region of interest. The genomic window can be any desired length as described elsewhere herein. The method involves breeding the first plant to a second plant which comprises in a different genomic insertion site within the same genomic window a first genomic locus of interest and does not comprise the first transgenic target site, and selecting a progeny plant comprising the first transgenic target site and the genomic locus of interest. In another embodiment, the method further involves providing a first plant having within a genomic window a first transgenic target site and a second transgenic target site having different genomic insertion sites wherein the first plant does not comprise a genomic locus of interest. Breeding the first plant with a second plant where the second plant comprises a genomic locus of interest within the genomic window and does not comprise the first and second transgenic target sites, and selecting for a progeny plant comprising the first transgenic target site, the second transgenic target site and the genomic locus of interest all having different genomic insertion sites within the genomic window. The first transgenic target site, the second transgenic target site and the genomic locus of interest of the progeny plants can segregate independently from one another at a rate of about 10-0.1%, about 10-0.5%, about 10-1%, about 10-5%, about 9-0.1%, about 9-0.5%, about 9-1%, about 9-5%, about 8-0.1%, about 8-0.5%, about 8-1%, about 8-4%, about 7-0.1%, about 7-0.5%, about 7-1%, about 7-4%, about 6-0.1%, about 6-0.5%, about 6-1%, about 6-3%, about 5-0.1%, about 5-0.5%, about 5-1%, about 4-0.1%, about 4-0.5%, about 4-1%, about 3-0.1%, about 3-0.5%, about 3-1%, about 2-0.1%, about 2-0.5%, about 1-0.1% or about 1-0.5%.

In this way, it is recognized that the plants provided herein can be crossed to produce a complex trait locus comprising any combination of the various genomic windows, transgenic target sites, genomic loci of interest, and/or polynucleotides of interest described herein.

B. Altering a Complex Trait Locus

The previous section describes various methods for creating a complex trait locus by adding target sites and/or genomic loci of interest to a genomic window thereby making a complex trait locus. It is recognized that a complex trait locus can also be altered by removing or breeding-away certain transgenic target sites and/or genomic loci of interest. The complex trait loci provided herein are designed such that each transgenic target site and/or genomic locus of interest has a different genomic insertion site and can segregate independently. Such a design allows traits to be bred into the genomic window and also to breed traits out of the genomic window.

The breeding methods described above for combining traits into a genomic window can also be employed to remove traits from a genomic window by breeding away the trait.

The method of altering a complex trait locus by breeding away comprises providing a first plant comprising a transgenic target site and/or genomic locus of interest to be removed and crossing the first plant with a second plant that does not have the particular transgenic target site and/or genomic locus of interest in the genomic window. The resulting progeny lacking the transgenic target site and/or genomic locus of interest would then be selected. For example, a first plant comprising a first transgenic target site, a second transgenic target site and a genomic locus of interest each having a different genomic insertion site within a genomic window could be crossed to a second plant. Progeny plants are selected wherein the genomic window does not comprise any one or any two of said first transgenic target sites or said first genomic locus of interest. In this way, at least 1, 2, 3, 4, 5, 6, 7, 8, 9, 10 or more target sites and/or genomic loci of interest can be removed from the complex trait locus.

In one embodiment of the method, the first plant has within a genomic window at least a first transgenic target site, a second transgenic target site, and a first genomic locus of interest. The genomic window of the first plant is about 10 cM in length and each of the first transgenic target site, second transgenic target site and first genomic locus of interest have different genomic insertion sites and segregate independently from one another at a rate of about 10% to about 0.1%. The method further comprises breeding the first plant to a second plant and selecting progeny wherein the genomic window of the progeny does not comprise any one or any two of said first transgenic target site, said second transgenic target site, or said first genomic locus of interest. In another embodiment, the genomic window of said first plant is about 5 cM in length and the first transgenic target site, the second transgenic target site and the first genomic locus of interest of the first plant segregate independently from one another at a rate of about 5% to about 0.1%. In a further embodiment, the first transgenic target site or the second transgenic target site segregate independently of the first genomic locus of interest of the first plant at a rate of about 5% to about 0.1%.

C. Methods of Altering the Transgenic Target Sites

The transgenic target sites provided herein comprise at least one recombination site, as described elsewhere herein, which can be utilized for direct insertion of one or more polynucleotides of interest into the target site. Thus, a complex trait locus comprising various target sites can be manipulated by site-specific integration methods. Such methods are described in detail in WO 99/25821, herein incorporated by reference. This method allows removing, adding and/or replacing various polynucleotides of interest within transgenic target sites of an established complex trait locus by employing site-specific recombination. Alternatively, the transgenic target site can be altered in a plant before the plant is utilized in breeding methods to produce a complex trait locus.

Transgenic target sites can be introduced into the plant genome by any of the transformation methods known in the art. For example, the transgenic target site is provided as a polynucleotide construct and introduced into a plant or plant cell. Then, site-specific integration can be employed to insert the transgenic target site into the genome of a plant. See, for example, U.S. Pat. Nos. 6,187,994, 6,262,341, 6,330,545, and 6,331,661 and US Publication Number 2011-0047655, herein incorporated by reference in their entirety. Once generated, such plants comprising a transgenic target site can be employed in the breeding methods discussed above or in a variety of methods to manipulate the sequence within the target site. Such methods employ various components of site-specific recombination systems as described in detail elsewhere herein.

The methods also comprise introducing into the plant cell comprising the integrated transgenic target site a transfer cassette. The transfer cassette comprises various components for the incorporation of polynucleotides of interest into the transgenic target site within the plant genome. As defined herein, the "transfer cassette" comprises at least a first recombination site, a polynucleotide of interest, and a second recombination site, wherein the first and second recombination sites are dissimilar and correspond to the recombination sites in the transgenic target site. In some embodiments, the first and second recombination sites of the transfer cassette are dissimilar and have a decreased compatibility with respect to one another and correspond to the recombination sites in the transgenic target site. It is recognized that any combination of recombination sites can be employed in the transfer cassettes to provide a polynucleotide of interest.

In one embodiment, the transfer cassette comprises a first recombination site, a first polynucleotide of interest, and a second recombination site. In such methods, the first and second recombination sites of the transfer cassette are recombinogenic (i.e. identical or corresponding) with the first and second recombination sites of the transgenic target site, respectively.

In a specific embodiment, the transfer cassette further comprises at least one coding region operably linked to a promoter that drives expression in a plant cell. As discussed elsewhere herein, a recombinase is provided that recognizes and implements recombination at the recombination sites of the transgenic target site and the transfer cassette. The recombinase can be provided by any means known in the art and is described in detail elsewhere herein. In a specific embodiment, the coding region of the transfer cassette encodes a recombinase that facilitates recombination between the first and the second recombination sites of the transfer cassette and the transgenic target site.

Further, the methods provide selecting at least one plant cell comprising integration of the transfer cassette at the transgenic target site. Methods for selecting plant cells with integration at the transgenic target site, such as selecting for cells expressing a selectable marker, are known in the art and are described elsewhere herein.

As such, at least 1, 2, 3, 4, 5, 6, 7, 8, 9, 10 or more transgenic target sites within the complex trait locus can be altered to comprise various polynucleotides of interest. Thus, the methods provided herein have the benefit of altering a complex trait locus by both breeding methods and by site-specific integration methods. By such methods, any polynucleotide of interest can be removed from and/or introduced into a complex trait locus in a plant.

IV. Methods of Introducing

The methods provided herein comprise introducing into a plant cell, plant or seed various polynucleotide constructs or polypeptides including, but not limited to, the various transgenic target sites, genomic loci of interest, transgenes, a target site comprising a first and a second dissimilar recombination sites or a first and a second dissimilar recombination sites having a decreased compatibility with respect to one another, site-specific recombinases, transfer cassettes, polynucleotides of interest or any active variants or fragments thereof provided herein.

By "introducing" is intended presenting to the plant the sequence (polypeptide or polynucleotide) in such a manner that the sequence gains access to the interior of a cell of the plant. The methods provided herein do not depend on a particular method for introducing a sequence into a plant, only that the polynucleotide or polypeptide gains access to the interior of at least one cell of the plant. Methods for introducing sequences into plants are known in the art and include, but are not limited to, stable transformation methods, transient transformation methods, virus-mediated methods, and sexual breeding. Thus, "introduced" in the context of inserting a polynucleotide construct into a cell, means "transfection" or "transformation" or "transduction" and includes reference to the incorporation of a polynucleotide construct into a plant cell where the polynucleotide construct may be incorporated into the genome of the cell.

In some embodiments, the plant cells, plants and seeds employed in the methods and compositions have a DNA construct stably incorporated into their genome. By "stably incorporated" or "stably introduced" is intended the introduction of a polynucleotide into the plant such that the nucleotide sequence integrates into the genome of the plant and is capable of being inherited by progeny thereof. Any protocol may be used for the stable incorporation of the DNA constructs or the various components employed herein.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, any of the polynucleotides employed herein may be introduced into plants by contacting plants with a virus or viral nucleic acids. Generally, such methods involve incorporating a desired polynucleotide within a viral DNA or RNA molecule. It is recognized that a sequence employed in the methods or compositions provided herein may be initially synthesized as part of a viral polyprotein, which later may be processed by proteolysis in vivo or in vitro to produce the desired recombinant protein. Further, it is recognized that promoters employed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

"Transient transformation" is intended to mean that a polynucleotide is introduced into the host (i.e., a plant) and expressed temporally. Such transient transformation methods include, but are not limited to, the introduction of any of the components (i.e. target sites, genomic loci of interest, recombination sites, site-specific recombinases, polynucleotides of interest or active variants and fragments thereof) directly into the plant or the introduction of the transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylamine (PEI; Sigma #P3143).

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, transformed seed (also referred to as "transgenic seed") having the recited DNA construct stably incorporated into their genome is provided.

V. Polynucleotides

Provided herein are polynucleotides comprising the various components of the complex trait loci or various components for altering the complex trait loci provided herein (i.e. the various transgenic target sites, genomic loci of interest, transgenes, recombination sites, site-specific recombinases, transfer cassettes, polynucleotides of interest or any active variants or fragments thereof).

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides provided herein also encompass all forms of sequences including, but not limited to, single-stranded forms, double-stranded forms, hairpins, stem-and-loop structures, and the like.

The compositions provided herein can comprise an isolated or substantially purified polynucleotide. An "isolated" or "purified" polynucleotide is substantially or essentially free from components that normally accompany or interact with the polynucleotide as found in its naturally occurring environment. Thus, an isolated or purified polynucleotide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

Further provided are recombinant polynucleotides comprising the various target sites, transgenes, genomic loci of interest, transfer cassettes, recombination sites, site-specific recombinases, polynucleotides of interest or any active variants or fragments thereof. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. For example, a transfer cassette can comprise restriction sites and a heterologous polynucleotide of interest. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments provided herein. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

In specific embodiments, one or more of the polynucleotides described herein can be provided in an expression cassette for expression in a plant or other organism or cell type of interest. The cassette can include 5' and 3' regulatory sequences operably linked to a polynucleotide provided herein. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in plants. The regulatory regions (i.e., promoters, transcriptional regulatory regions, and translational termination regions) and/or a polynucleotide provided herein may be native/analogous to the host cell or to each other. Alternatively, the regulatory regions and/or a polynucleotide provided herein may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the plant host, or may be derived from another source (i.e., foreign or heterologous) to the promoter, the recombinant polynucleotide, the plant host, or any combination thereof. Convenient termination regions are available from the Ti-plasmid of *A. tumefaciens*, such as the octopine synthase and nopaline synthase termination regions. See also Guerineau et al. (1991)*Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

In some embodiments, an expression cassette provided herein can be combined with constitutive, tissue-preferred, or other promoters for expression in plants. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures for each of these are incorporated herein by reference in their entirety.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of a polynucleotide of interest within a particular plant tissue. Tissue-preferred promoters are known in the art. See, for example, Yamamoto et al. (1997) *Plant J.* 12(2):255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing non-legume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roIB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324.

The expression cassette containing the polynucleotides provided herein can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D) and sulfonylureas. Additional selectable markers include phenotypic markers such as beta-galactosidase and fluorescent proteins such as green fluorescent protein (GFP) (Su et al. (2004) *Biotechnol. Bioeng.* 85:610-9 and Fetter et al. (2004) *Plant Cell* 16:215-28), cyan fluorescent protein (CYP) (Bolte et al. (2004) *J. Cell Science* 117:943-54 and Kato et al. (2002) *Plant Physiol.* 129:913-42), and yellow fluorescent protein (PhiYFP™. from Evrogen; see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in The Operon, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Nail. Acad. Sci.* USA 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the compositions presented herein.

Where appropriate, the sequences employed in the methods and compositions (i.e., the polynucleotide of interest, the recombinase, etc.) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

VI. Libraries Comprising Transgenic Target Sites and Methods of Making

Provided herein is a method of generating a library of plants, seeds or plant cells comprising any of the various transgenic target sites described herein. The method comprises introducing a recombinant construct comprising a transgenic target site into a population of plants, seeds or plant cells. By "population" is intended a group or collection of plants, seeds or plant cells. The population can comprise 2 or more (i.e. 5, 10, 100, 300, 500, 700, 900, 1100, 1300, 1500, 1700, 1900, 2100, 2300, 2500, 2900, 3100, 3300, 3500, 3700, 3900, 4000, 4096, $10^4$, $10^5$, $10^6$ or greater) plants, seeds or plant cells. As used herein, a "library" is a population of plants, seeds or plant cells comprising at least one transgenic target site stably incorporated into their genomes.

To generate the plant library, a recombinant construct comprising a transgenic target site is introduced into a population of plant cells. The recombinant construct can be introduced by any means known in the art. The method comprises identifying a plant or plant cell having the recombinant construct and characterizing the genomic insertion site of the recombinant construct. A variety of methods are available for identifying at least one plant cell comprising in its genome a transgenic target site and characterizing the genomic insertion site. Such methods include, but are not limited to, selection based on a selectable marker, PCR methods, sequencing methods, nuclease digestion, Southern blots, and any combination thereof. See, for example, U.S. patent application Ser. No. 12/147,834, herein incorporated by reference in its entirety.

The recombinant construct can integrate at any location in the plant genome. In one embodiment, the library of plants, seeds or plant cells is assembled such that each member of the library comprises a target site having a different genomic insertion site and when combined into a single plant genome, can segregate independently from each other. In such cases, the integration sites of the transgenic target sites are found about 0.1, 0.2, 0.3, 0.4, 0.5, 0.6, 0.7, 0.8, 0.9, 1, 2, 3, 4, 5, 6, 7, 8, 9, 10 cM or more from each other in the plant genome. Alternatively, the integration sites of the transgenic target sites are found about 1-10 cM, about 2-10 cM, about 2-5 cM, about 3-10 cM, about 3-6 cM, about 4-10 cM, about 4-7 cM, about 5-10 cM, about 5-8 cM, about 6-10 cM, about 6-9 cM, about 7-10 cM, about 8-10 cM, about 9-10 cM, about 0.5-1%, about 0.5-5%, about 0.5-10%, about 0.1-1 cM, about 0.1-2 cM, about 0.1-3 cM, about 0.1-4 cM, about 0.1-5 cM, about 0.1-6 cM, about 0.1-7 cM about 0.1-8 cM, about 0.1-9 cM or about 0.1-10 cM from each other in the plant genome.

In some embodiments, the library of plants, seeds or plant cells comprises a population wherein the members of said population have the transgenic target site at about 10 cM to about 1 cM intervals within a defined genomic window. By "interval" is intended that there is a transgenic target site located at a defined distance from another transgenic target site. For example, transgenic target sites located at 1 cM intervals within a 10 cM genomic window means that there is a target site at every 1 cM distance within the genomic window such that the genomic window is saturated with target sites. By "saturated" is intended that the library comprises a population of members having the transgenic target site at about 10 cM intervals to about 0.1 cM intervals, about 10 cM intervals to about 0.5 cM intervals, about 5 cM intervals to about 0.1 cM intervals, about 4 cM intervals to about 0.1 cM intervals, about 3 cM intervals to about 0.1 cM intervals, or about 2 cM intervals to about 0.1 cM intervals across the entire genomic window.

In some embodiments, the library of plants, seeds or plant cells comprises a population wherein the members of said population have the transgenic target site at about 10 cM to about 1 cM intervals within a defined genomic window. The defined genomic window can be any length including about 1, 2, 3, 4, 5, 6, 7, 8, 9, 10, 15, 20, 30, 40, 50, 60, 70, 80, 90, 100, 250, 500, 750, 1000, 2000, 3000, 4000, 5000 cM in length or up to the complete genome. The genomic window can be about 1-5 cM, about 1-10 cM, about 10-30 cM, about 30-60 cM, about 60-100 cM, about 100-500 cM, about 500-1000 cM, about 1000-2500 cM, about 2500-5000 cM, or up to the whole length of the genome. In the case that the genomic window is the entire genome, the plant, seed or plant cell library comprises a transgenic target site at every defined interval so that the entire genome is saturated with transgenic target sites.

Also encompassed herein, is a method for identifying plants or plant cells having a transgenic target site within a given genomic window. A sub-population of plants, seeds or plant cells can be selected from the library such that the transgenic target sites within each member of the library has a different genomic insertion site and segregates independently from one another at a rate of about 10% to about 0.1% when present in the same genome.

In another embodiment, the library comprises a population of plants, seeds or plant cells wherein the genomic insertion site of the transgenic target site in each member of the library segregates independently from one another when present in the same genome and the members of the population have transgenic target sites located at 10 cM intervals to about 1 cM intervals within a genomic window.

These libraries find use in producing a complex trait locus in any given genomic window by crossing plants within the library or with plants from libraries comprising different transgenic target sites. In this way, multiple transgenic target sites can be brought together into a single plant genome within a given genomic window.

VII. Fragments, Variants and Sequence Comparisons

Active variants and fragments of the various recombination sites, site-specific recombinases and polynucleotides of interest are also provided herein. Biological activity for each of these components is described elsewhere herein.

By "fragment" is intended a portion of the polynucleotide or a portion of the amino acid sequence and hence protein encoded thereby. Fragments of a polynucleotide may encode protein fragments that retain the biological activity of the native protein (i.e., a fragment of a recombinase implements a recombination event). As used herein, a "native" polynucleotide or polypeptide comprises a naturally occurring nucleotide sequence or amino acid sequence, respectively. Thus, fragments of a polynucleotide may range from at least about 20 nucleotides, about 50 nucleotides, about 100 nucleotides, and up to the full-length polynucleotide. A fragment of a polynucleotide that encodes a biologically active portion of a protein employed in the methods or compositions will encode at least 15, 25, 30, 50, 100, 150, 200, or 250 contiguous amino acids, or up to the total number of amino acids present in a full-length protein. Alternatively, fragments of a polynucleotide that are useful as a hybridization probe generally do not encode fragment proteins retaining biological activity. Thus, fragments of a nucleotide sequence may range from at least about 10, 20, 30, 40, 50, 60, 70, 80 nucleotides or up to the full length sequence.

"Variant" sequences have a high degree of sequence similarity. For polynucleotides, conservative variants include those sequences that, because of the degeneracy of the genetic code, encode the amino acid sequence of one of the native polypeptides. Variants such as these can be identified with the use of well-known molecular biology techniques, as, for example, with polymerase chain reaction (PCR) and hybridization techniques. Variant polynucleotides also include synthetically derived nucleotide sequences, such as those generated, for example, by using site-directed mutagenesis but which still encode a protein. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by known sequence alignment programs and parameters.

Variants of a particular polynucleotide (i.e., the reference nucleotide sequence) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to a recombinase are known in the art. Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins are biologically active, that is they continue to possess the desired biological activity of the native protein. Such variants may result from, for example, genetic polymorphism or from human manipulation. Biologically active variants of a native protein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by known sequence alignment programs and parameters. A biologically active variant of a protein may differ from that protein by as few as 1-15 amino acid residues, as few as 1-10, such as 6-10, as few as 5, as few as 4, 3, 2, or even 1 amino acid residue.

The following terms are used to describe the sequence relationships between two or more polypeptides or polynucleotides. As used herein, "reference sequence" is a defined sequence used as a basis for sequence comparison. A reference sequence may be a portion or the entirety of a specified sequence. Sequence relationships can be analyzed and described using computer-implemented algorithms. The sequence relationship between two or more polynucleotides or two or more polypeptides can be determined by generating the best alignment of the sequences, and scoring the matches and the gaps in the alignment, which yields the percent sequence identity, and the percent sequence similarity. Polynucleotide relationships can also be described based on a comparison of the polypeptides each encodes. Many programs and algorithms for the comparison and analysis of sequences are well-known in the art.

Unless otherwise stated, sequence identity/similarity values provided herein refer to the value obtained using GAP Version 10 (GCG, Accelrys, San Diego, CA) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff (1989) *Proc. Natl. Acad. Sci USA* 89:10915); or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find an alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold.

As used herein, "sequence identity" or "identity" in the context of two polynucleotides or polypeptide sequences makes reference to the residues in the two sequences that are the same when aligned for maximum correspondence. Sequence, particularly polypeptides, that differ by conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated using the selected scoring matrix (BLOSUM62 by default for GAP).

Proteins may be altered in various ways including amino acid substitutions, deletions, truncations, and insertions. Methods for such manipulations are generally known in the art. For example, amino acid sequence variants of the recombinase proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Variant polynucleotides and proteins also encompass sequences and proteins derived from a mutagenic and/or recombinogenic procedure such as DNA shuffling. With such a procedure, one or more different coding sequences can be manipulated to create a new protein possessing the desired properties. In this manner, libraries of recombinant polynucleotides are generated from a population of related polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nat Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Non-limiting examples of methods and compositions disclosed herein are as follows:

1. A plant or seed having in its genome a genomic window comprising at least a first transgenic target site, a second transgenic target site, and a genomic locus of interest, wherein the genomic window is about 10 cM in length;
   wherein each of said genomic locus of interest, said first transgenic target site and said second transgenic target site have different genomic insertion sites; and,
   wherein each of said first transgenic target site, said second transgenic target site, and said genomic locus of interest segregate independently from one another at a rate of about 10% to about 0.1%.

2. The plant or seed of embodiment 1, wherein the genomic window is about 5 cM in length; wherein each of said first transgenic target site, said second transgenic target site, and said genomic locus of interest segregate independently from one another at a rate of about 5% to about 0.1%.

3. The plant or seed of embodiment 1 or 2, wherein (a) said first transgenic target site or said second transgenic target site segregate independently from said genomic locus of interest at a rate of about 5% to about 0.1%; or, (b) said first transgenic target site and said second transgenic target site segregate independently from one another at a rate of about 5% to about 0.1%.

4. The plant or seed of embodiment 1, 2, or 3, wherein said first transgenic target site comprises a first recombination site and a second recombination site, wherein (i) said first and said second recombination sites are dissimilar with respect to one another; or (ii) said first and said second recombination sites are dissimilar and have a decreased compatibility with respect to one another;

and said second transgenic target site comprises a third recombination site and a fourth recombination site, wherein (i) said third and said fourth recombination sites are dissimilar with respect to one another; or (ii) said third and said fourth recombination sites are dissimilar and have a decreased compatibility with respect to one another.

5. The plant or seed of any one of embodiments 1-4, wherein said first transgenic target site or said second transgenic target site is found within about 5 cM from the genomic locus of interest.

6. The plant or seed of any one of embodiments 1-4, wherein said first transgenic target site or said second transgenic target site is found within about 2 cM from the genomic locus of interest.

7. The plant or seed of any one of embodiments 1-4, wherein said first transgenic target site or said second transgenic target site is found within about 0.5 cM from the genomic locus of interest.

8. The plant or seed of any one of embodiments 1-7, wherein said genomic window further comprises a third transgenic target site comprising a fifth recombination site and a sixth recombination site, wherein (i) said fifth and said sixth recombination sites are dissimilar with respect to one another; or (ii) said fifth and said sixth recombination sites are dissimilar and have a decreased compatibility with respect to one another;

and said third transgenic target site has a different genomic insertion site than said first transgenic target site, said second transgenic target site and said genomic locus of interest.
9. The plant or seed of embodiment 8, wherein said third transgenic target site is found within about 5 cM from the genomic locus of interest.
10. The plant or seed of any one of embodiments 1-9, wherein said genomic locus of interest confers a trait comprising male sterility, site-specific recombination, abiotic stress tolerance, altered phosphorus, altered antioxidants, altered fatty acids, altered essential amino acids, altered carbohydrates, herbicide tolerance, insect resistance or disease resistance.
11. The plant or seed of any one of embodiments 1-10, wherein said genomic locus of interest comprises a transgene.
12. The plant or seed of any one of embodiments 1-10, wherein said genomic locus of interest comprises a native trait.
13. The plant or seed of any one of embodiments 1-12, wherein said first transgenic target site comprises at least one polynucleotide of interest.
14. The plant or seed of any one of embodiments 1-12, wherein said second transgenic target site comprises at least a second polynucleotide of interest.
15. The plant or seed of embodiment 4, wherein said second transgenic target site comprises the same dissimilar recombination sites as said first transgenic target site.
16. The plant or seed of embodiment 4, wherein said second transgenic target site comprises different dissimilar recombination sites as said first transgenic target site.
17. The plant or seed of embodiment 4, wherein the dissimilar recombination sites of said first transgenic target site and said second transgenic target site comprises a LOX site, a mutant LOX site, a FRT site or a mutant FRT site.
18. The plant or seed of embodiment 17, wherein the dissimilar recombination sites of said first and said second transgenic target sites comprise a FRT site or a mutant FRT site.
19. The plant or seed of embodiment 17 or 18, wherein said mutant FRT site comprises a FRT5 site, a FRT6 site, a FRT7 site, a FRT12 site, or a FRT87 site.
20. The plant or seed of embodiment 15, wherein the dissimilar recombination sites of said first and said second transgenic target sites comprise a FRT1 site and a FRT87 site.
21. The plant or seed of any one of embodiments 1-20, wherein said plant or seed is a monocot.
22. The plant or seed of embodiment 21, wherein said monocot is maize, wheat, rice, barley, sorghum, or rye.
23. The plant or seed of any one of embodiments 1-20, wherein said plant or seed is a dicot.
24. The plant or seed of embodiment 23, wherein the dicot is soybean, *Brassica*, sunflower, cotton, or alfalfa.
25. A method for producing a second plant comprising applying plant breeding techniques to a first plant, or parts thereof, wherein said first plant is the plant of any one of embodiments 1-24, and wherein application of said techniques results in the production of said second plant.
26. The method of embodiment 25, wherein said second plant comprises at least one additional transgenic target site or at least one additional genomic locus of interest within said genomic window when compared to said first plant; wherein each of said additional transgenic target site and said additional genomic locus of interest have a different genomic insertion site with respect to each other and with respect to said first transgenic target site, said second transgenic target site and said genomic locus of interest.
27. The method of embodiment 26, wherein the at least one additional transgenic target site comprises a polynucleotide of interest.
28. The method of embodiment 25, wherein said second plant comprises at least one less transgenic target site or at least one less genomic locus of interest within said genomic window when compared to said first plant.
29. A method of producing a complex trait locus in the genome of a plant comprising (a) providing a first plant having within a genomic window at least a first transgenic target site, and wherein said genomic window is about 10 cM in length and said first plant does not comprise a first genomic locus of interest; (b) breeding to said first plant a second plant, wherein said second plant comprises in said genomic window the first genomic locus of interest and said second plant does not comprise said first transgenic target site; and, (c) selecting a progeny plant from step (b) comprising said first transgenic target site and said genomic locus of interest; wherein said first transgenic target site and said first genomic locus of interest have different genomic insertion site in said progeny plant.
30. A method of producing a complex trait locus in the genome of a plant comprising
(a) providing a first plant having within a genomic window at least a first transgenic target site and a second transgenic target site, wherein said genomic window is about cM in length, and wherein said first transgenic target site and said second transgenic target site have a different genomic insertion site, wherein said first plant does not comprise a first genomic locus of interest;
(b) breeding to said first plant a second plant, wherein said second plant comprises in said genomic window the first genomic locus of interest, wherein said second plant does not comprise said first transgenic target site or said second transgenic target site in the genomic window; and,
(c) selecting a progeny plant from step (b) comprising said first transgenic target site, said second transgenic target site and said first genomic locus of interest; wherein each of said first transgenic target site, said second transgenic target site and said first genomic locus of interest have a different genomic insertion site in said progeny plant; and,
  wherein each of said first transgenic target site, said second transgenic target site, and said genomic locus of interest in said progeny plant segregate independently from one another at a rate of about 10% to 0.1%.
31. The method of embodiment 30, wherein said genomic window is about 5 cM in length and wherein each of said first transgenic target site, said second transgenic target site, and said genomic locus of interest in said progeny plant segregate independently from one another at a rate of about 5% to 0.1%.
32. The method of embodiments 30 or 31, wherein (a) said first transgenic target site or said second transgenic target site segregate independently from said first genomic locus of interest at a rate of about 5% to about 0.1%; or, (b) said first transgenic target site and said second transgenic target site of said progeny plant segregate independently from one another at a rate of about 5% to about 0.1%.
33. The method of any one of embodiments 30-32, wherein said method further comprises (a) breeding to said progeny plant a third plant comprising a second genomic locus of interest, wherein said third plant comprises in said genomic window said second genomic locus of interest, wherein said third plant does not comprise said first transgenic target site, said second transgenic target site or said first genomic locus of interest in said genomic window; and (b) selecting a second progeny plant from step (a) comprising said first transgenic target site, said second transgenic target site, said first genomic locus of interest, and said second genomic locus of interest; and wherein each of said first transgenic target site, said second transgenic target site, said first genomic locus of interest and said second genomic locus of interest have a different genomic insertion site in said second progeny plant; and, wherein each of said first transgenic target site, said second transgenic target site, said first genomic locus of interest, or said second genomic locus of interest in said second progeny plant segregate independently from one another at a rate of about 10% to about 0.1%.
34. The method of any one of embodiments 30-33, wherein
(a) said first transgenic target site comprises a first recombination site and a second recombination site, wherein (i) said first and said second recombination sites are dissimilar with respect to one another and, said first transgenic target site comprises a polynucleotide of interest; or (ii) said first and said second recombination sites are dissimilar and have a decreased compatibility with respect to one another and, said first transgenic target site comprises a polynucleotide of interest; and,
(b) said second transgenic target site comprises a third recombination site and a fourth recombination site, wherein (i) said third and said fourth recombination sites are dissimilar with respect to one another; and said second transgenic target site further comprises a second polynucleotide of interest; or
(ii) said third and said fourth recombination sites are dissimilar and have a decreased compatibility with respect to one another; and said second transgenic target site further comprises a second polynucleotide of interest.
35. The method of any one of embodiments 30-34, wherein the genomic position of said first transgenic target site and the first genomic locus of interest are within 5 cM of each other.
36. The method of any one of embodiments 30-34, wherein the genomic position of said first transgenic target site and the first genomic locus of interest are within 2 cM of each other.
37. The method of any one of embodiments 30-34, wherein the genomic position of said first transgenic target site and the genomic locus of interest are within 0.5 cM of each other.
38. The method of any one of embodiments 30-31, wherein the first genomic locus of interest confers a trait comprising male sterility, site-specific recombination, abiotic stress tolerance, altered phosphorus, altered antioxidants, altered fatty acids, altered essential amino acids, altered carbohydrates, herbicide tolerance, insect resistance or disease resistance.
39. The method of any one of embodiments 29-38, wherein the first genomic locus of interest comprises a native trait, a transgene of interest, or an additional transgenic target site.
40. The method of embodiment 34, wherein said first transgenic target site and said second transgenic target site comprise the same dissimilar recombination sites.
41. The method of embodiment 34, wherein said first transgenic target site and said second transgenic target site comprise different dissimilar recombination sites.
42. The method of embodiment 34, 40, or 41, wherein the dissimilar recombination sites comprise a LOX site, a mutant LOX site, a FRT site or a mutant FRT site.
43. The method of embodiment 34, 40, or 41, wherein the dissimilar recombination sites comprise a FRT site or a mutant FRT site.
44. The method of embodiment 42 or 43, wherein said mutant FRT site comprises a FRT5 site, a FRT6 site, a FRT7 site, a FRT12 site, or a FRT87 site.
45. The method of embodiment 34, wherein said first and said second transgenic target sites comprise a FRT1 site and a FRT87 site.
46. A method of altering a complex trait locus in the genome of a plant comprising (a) providing a first plant having within a genomic window at least a first transgenic target site, a second transgenic target site, and a first genomic locus of interest, wherein said genomic window is about 10 cM in length, and wherein said first transgenic target site, said second transgenic target site, said first genomic locus of interest have a different genomic insertion site;
wherein each of said first transgenic target site, said second transgenic target site, or said first genomic locus of interest in said first plant segregate independently from one another at a rate of about 10% to about 0.1%;
(b) breeding to said first plant a second plant;
(c) selecting a progeny plant from step (b), wherein said genomic window from said progeny plant does not comprise any one of or any two of said first transgenic target site, said second transgenic target site, or said first genomic locus of interest.
47. The method of embodiment 46, wherein said genomic window is about 5 cM in length and wherein each of said first transgenic target site, said second transgenic target site, or said first genomic locus of interest in said first plant segregate independently from one another at a rate of about 5% to about 0.1%;
48. The method of embodiment 46 or 47, wherein (a) said first transgenic target site and said second transgenic target site of said first plant segregate independently from one another at a rate of about 5% to about 0.1%; or, (b) said first transgenic target site or said second transgenic target site segregate independently of said first genomic locus of interest of said first plant at a rate of about 5% to about 0.1%.
49. The method of embodiment 46, 47, or 48, wherein
(a) said first transgenic target site comprises a first recombination site and a second recombination site, wherein (i) said first and said second recombination sites are dissimilar with respect to one another and, said first transgenic target site comprises a polynucleotide of interest; or (ii) said first and said second recombination sites are dissimilar and have a decreased compatibility with respect to one another and, said first transgenic target site comprises a polynucleotide of interest; and, (b) said second transgenic target site comprises a third recombination site and a fourth recombination site, wherein (i) said third and said fourth recombination sites are dissimilar with respect to one another; and said second transgenic target site further comprises a second polynucleotide of interest; or (ii) said third and said fourth recombination sites are dissimilar and have a decreased compatibility with respect to one another; and said second transgenic target site further comprises a second polynucleotide of interest.

51. The method of any one of embodiments 46-49, wherein the genomic position of said first transgenic target site and the first genomic locus of interest are within 2 cM of each other.

52. The method of any one of embodiments 46-49, wherein the genomic position of said first transgenic target site and the genomic locus of interest are within 0.5 cM of each other.

53. The method of any one of embodiments 46-49, wherein the genomic locus of interest confers a trait comprising male sterility, site-specific recombination, abiotic stress tolerance, altered phosphorus, altered antioxidants, altered fatty acids, altered essential amino acids, altered carbohydrates, herbicide tolerance, insect resistance or disease resistance.

54. The method of any one of embodiments 46-49, wherein the first genomic locus of interest comprises a native trait, a transgene of interest, or an additional transgenic target site.

55. The method of any one of embodiments 25-54, wherein said plant is a monocot.

56. The method of embodiment 55, wherein said monocot is maize, wheat, rice, barley, sorghum, or rye.

57. The method of any one of embodiments 25-54, wherein said plant is a dicot.

58. The method of embodiment 57, wherein the dicot is soybean, *Brassica*, sunflower, cotton, or alfalfa.

59. A method of generating a library of plants, seeds or plant cells, wherein each of said plant, said seed, or said plant cell in said library comprise a transgenic target site, said method comprising: (a) introducing into a population of plant cells a recombinant construct comprising a transgenic target site; (b) identifying a plant cell or a plant having the recombinant construct; (c) characterizing the genomic insertion site of said recombinant construct within the plant cell or plant of step (b); and, (d) assembling the library of plants, seeds or plant cells wherein each member of said library comprises a transgenic target site having a different genomic insertion site, and, when the transgenic target sites are combined into a single plant genome, said transgenic target sites segregate independently from one another.

60. The method of embodiment 59, wherein said library of plants, seeds or plant cells of step (d) comprises a population of plants, seeds, or plants cells wherein the members of said population have the transgenic target site at about 10 cM intervals to about 1 cM intervals within a genomic window.

61. The method of embodiment 62, wherein the members of said population have the transgenic target site at about 2 cM intervals within a genomic window.

62. The method of embodiment 60 or 61, wherein the genomic window is the complete genome.

63. A method for identifying plants or plant cells having a transgenic target site in a genomic window comprising (a) providing a library of plants, seeds or plant cells, wherein each of said plant, said seed, or said plant cell in said library comprises a transgenic target site in a different genomic insertion site, wherein the genomic insertion site of said transgenic target site in each member of said library segregate independently from one another when present in the same genome; and (b) identifying a sub-population of plants, seeds or plant cells in said library, wherein the genomic insertion site of said transgenic target site in each member of said sub-population segregate independently from one another at a rate of about 10% to about 0.1% when present in the same genome.

64. A library of plants, seeds or plant cells comprising a population of plants, seeds, or plant cells having a transgenic target site stably incorporated into their genomes, wherein the genomic insertion site of said transgenic target site in each member of said library segregate independently from one another when present in the same genome and the members of said population have the transgenic target sites at about 10 cM intervals to about 1 cM intervals within a genomic window.

65. The library of plants, seeds or plant cells of embodiment 64, wherein the genomic window comprises the complete genome.

66. The library of plants, seeds or plant cells of embodiment 64, wherein the genomic window is about 10 cM in length. 67. The library of plants, seeds or plant cells of embodiments 64, 65, or 66, wherein the members of said population have the transgenic target site at about 2 cM intervals within a genomic window.

68. A plant or seed having in its genome a genomic window comprising at least a first transgenic target site, a second transgenic target site, and a genomic locus of interest, wherein said genomic window: (a) is flanked by at least a first marker comprising UMC1160, UMC2224, NPI579B, PMCB1, IDP3917, GPM199C, IDP1425, MMP68, UMC2225, STD2C(DBA), TIDP3300, CSU1171, SUT1 or UMC1166, and at least a second marker comprising AY107207, UMC1568, IDP3783, BNLG1429, IDP209, LTK1 or IDP7169; or (b) is flanked by at least a first marker comprising UMC1625, UMC2196, UMC2312, BNLG1867, PZA03047, UMC1229, UCK1, RZ390D(CYB5), MMP20, MMP10, MMP160, PHP20528, UMC2314, UAZ232B(SCI) or UMC2313, and at least a second marker comprising CDO545, PHP20854, UMC1133, UFG69, MMP76, Y1, BNLG1422, MMP108B, MMP4, UMC1006, or RZ444E;

wherein each of said genomic locus of interest, said first transgenic target site and said second transgenic target site have different genomic insertion sites; and, wherein each of said first transgenic target site, said second transgenic target site, and said genomic locus of interest segregate independently from one another at a rate of about 10% to about 0.1%.

69. Progeny plants obtained from the plant of embodiment 68.

70. The plant of embodiment 68 further comprising at least one altered target sequence, wherein the at least one altered target sequence originated from a corresponding target sequence that was recognized and cleaved by a double-strand break-inducing agent, and wherein the at least one altered target sequence is located in said genomic window.

71. A method of producing a complex trait locus in the genome of a plant comprising
(a) providing a first plant having within a genomic window at least a first transgenic target site, wherein said first plant does not comprise a first genomic locus of interest, and wherein said genomic window: (i) is flanked by at least a first marker comprising UMC1160, UMC2224, NPI579B, PMCB1, IDP3917, GPM199C, IDP1425, MMP68, UMC2225, STD2C(DBA), TIDP3300, CSU1171, SUT1 or UMC1166, and at least a second marker comprising AY107207, UMC1568, IDP3783, BNLG1429, IDP209, LTK1 or IDP7169; or
(ii) is flanked by at least a first marker comprising UMC1625, UMC2196, UMC2312, BNLG1867, PZA03047, UMC1229, UCK1, RZ390D(CYB5), MMP20, MMP10, MMP160, PHP20528, UMC2314, UAZ232B(SCI) or UMC2313, and at least a second marker comprising CDO545, PHP20854, UMC1133, UFG69, MMP76, Yl, BNLG1422, MMP108B, MMP4, UMC1006, or RZ444E;
(b) breeding to said first plant a second plant, wherein said second plant comprises in said genomic window the first genomic locus of interest and said second plant does not comprise said first transgenic target site; and,
(c) selecting a progeny plant from step (b) comprising said first transgenic target site and said genomic locus of interest; wherein said first transgenic target site and said first genomic locus of interest have different genomic insertion site in said progeny plant.

72. A plant or seed having in its genome a genomic window comprising at least a first transgenic target site, a second transgenic target site, and a genomic locus of interest, wherein said genomic window: is flanked by at least a first marker comprising SATT613, SATT284, S60414-TB or SATT462, and at least a second marker comprising SATT481, SATT156 or SCT_010;
wherein each of said genomic locus of interest, said first transgenic target site and said second transgenic target site have different genomic insertion sites; and, wherein each of said first transgenic target site, said second transgenic target site, and said genomic locus of interest segregate independently from one another at a rate of about 10% to about 0.1%.

73. Progeny plants obtained from the plant of embodiment 72.

74. The plant of embodiment 72 further comprising at least one altered target sequence, wherein the at least one altered target sequence originated from a corresponding target sequence that was recognized and cleaved by a double-strand break-inducing agent, and wherein the at least one altered target sequence is located in said genomic window.

75. A method of producing a complex trait locus in the genome of a plant comprising (a) providing a first plant having within a genomic window at least a first transgenic target site, wherein said first plant does not comprise a first genomic locus of interest, and wherein said genomic window: is flanked by at least a first marker comprising SATT613, SATT284, S60414-TB or SATT462, and at least a second marker comprising SATT481, SATT156 or SCT_010; (b) breeding to said first plant a second plant, wherein said second plant comprises in said genomic window the first genomic locus of interest and said second plant does not comprise said first transgenic target site; and, (c) selecting a progeny plant from step (b) comprising said first transgenic target site and said genomic locus of interest; wherein said first transgenic target site and said first genomic locus of interest have different genomic insertion site in said progeny plant.

The following examples are offered by way of illustration and not by way of limitation.

EXPERIMENTAL

Example 1

Production of a Corn Library Comprising Transgenic Target Sites for Site Specific Integration (SSI)

A method of generating a large collection of transgenic plants or 'library' of plants, seeds or plant cells comprising any of the various transgenic target sites (TTS) for site specific integration (SSI) was developed for corn as described below.

Development of SSI Platform II Vectors

Vectors for *Agrobacterium* transformation of corn were developed using derivative constructs of the original co-integrate *Agrobacterium* binary system described in Komari, et al., 1996. These vectors carried the necessary molecular elements to enable site specific integration (SSI) based on the FLP/FRT system from yeast. The *Agrobacterium* constructs with FRT sites to facilitate Recombinase Mediated Cassette Exchange (RMCE) (Seibler and Bode, 1997) were named SSI platform II vectors. In addition to the FRT sites, intermediates for SSI platform II vectors included either a multiple cloning site or an Invitrogen™ Gateway® destination site for Gateway® cloning to provide efficient introduction of trait genes for transformation (FIG. 2). Another feature of the SSI platform II vectors was the inclusion of loxP sites flanking the region where trait genes are introduced to allow cre/lox excision to be used for removal of the trait genes if that should be desired. The elements included in SSI platform II vectors allowed for a new gene or multiple genes to be added to existing genes at a transgenic target site (TTS), including, for example, employing FRT1 and FRT87. If cre/lox excision was used in combination with SSI introduction of new genes there was an effective replacement of existing genes at a transgenic target site. SSI platform II vectors provided for the placement of value on a transgenic target site and provided the flexibility to modify the gene content of a transgenic target site considered to be of high value.

A common feature of SSI platform II vectors is the placement of the FRT sites which set up a gene-trapping configuration. The FRT1 site was placed between a promoter (for example a maize ubiquitin promoter, UBIZMPRO) as shown in FIG. 2A) and coding region of the maize codon optimized phosphinothricin acetyltransferase (MO-PAT, PHP35557, FIG. 2A) or phosphomannose isomerase (PMI, PHP44290, FIG. 2B) selectable marker genes. The FRT87 site was placed downstream (three prime) of the terminator sequence of the final selectable marker gene in the SSI region of SSI platform II vectors (for example a PIN II terminator (PINII TERM) or a Calcium Mosaic Virus 35S terminator, CAMV35S TERM as shown in FIG. 2A). Some vectors comprised a second selectable marker, such as MO-PAT between FRT1 and FRT87 which was driven by a *Oryza sativa* actin promoter (OS-ACTIN PRO, FIG. 2B). Recombinant insertions were recovered following introduction of a DNA sequence with a promoterless selectable marker gene that was not included in the target site and which contained the FRT1 site upstream of the coding sequence in the same way as demonstrated for SSI platform II vectors. The promoterless marker constructs, referred to as SSI donor constructs, were introduced by biolistics methods into cells with transgenic target sites. Following successful RMCE, the initial target site marker (MO-PAT, PMI) was no longer expressed and the newly introduced marker from the donor construct was expressed as a result of the recombination at FRT1 and capture of the promoter upstream of the gene trap (see U.S. Pat. No. 7,102,055). Both selectable and visual markers can be used in the trap to indicate successful site specific integration.

Figure 3:
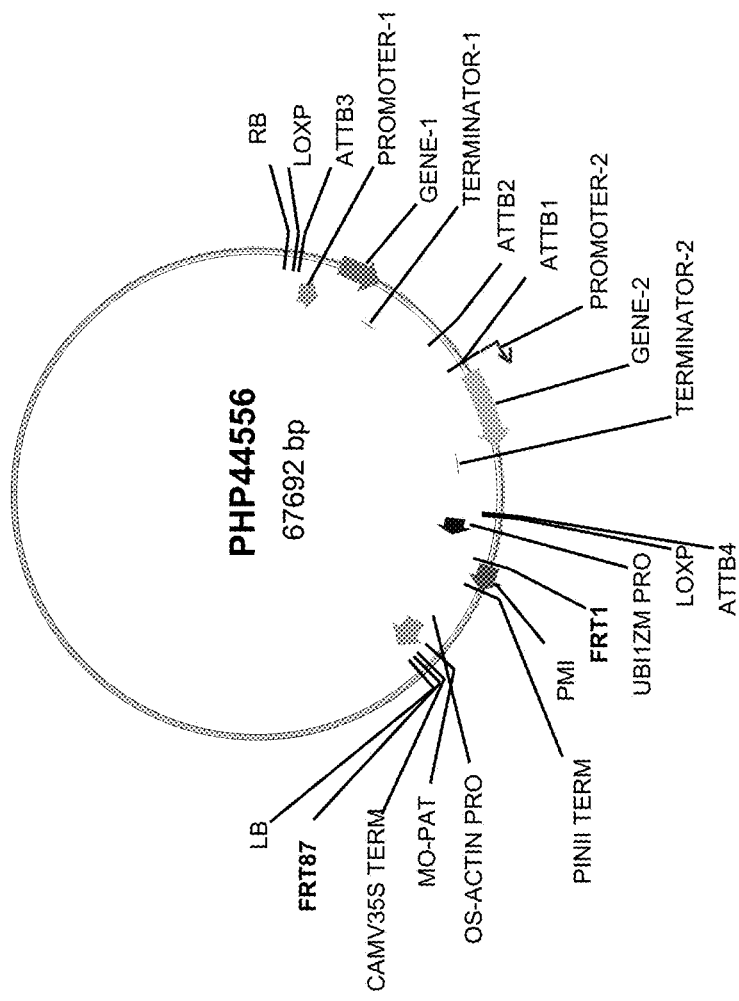
FIG. 3 is a Schematic overview of plasmid PHP44556.

Construct intermediates that include FRT1 and FRT87 sites around the selectable marker gene or genes at the left T-DNA border (LB) region are shown in FIG. 2. Only the T-DNA regions of the constructs are shown for simplicity. PHP35557 was a derivative of the pSB11 like vector (Komari, et al., 1996) where trait genes are added prior to the formation of the final co-integrate construct. PHP44290 is the product of co-integration between pSB1 and pSB11 like intermediates (Komari, et al., 1996) and an Invitrogen™ Gateway® destination site was used in the site for gene introduction via Gateway® cloning (FIG. 2). An example of one SSI platform II vector, PHP44556 is shown in FIG. 3. A large number of related constructs were produced with differences in gene numbers, gene activities, gene sequences, promoters, transcription termination elements, orientations of genes relative to one another, and positions of genes between the loxP sites. Each new construct was used to make multiple corn transformants (n=20 to 100), each transformant with a unique transgenic target site(s). The result of this transformation work based on SSI platform II was a large number of transgenic target sites in corn carrying the elements to facilitate site specific integration and/or trait gene excision and therefore with the capabilities for gene addition or gene replacement.

Development of a Corn SSI Library

A first population of transgenic plants was generated using a Maize Inbred line 1 (MI1) and involved 16 constructs built from SSI platform II. These constructs were all identical in the T-DNA region to one or the other of the two constructs shown in FIG. 2 except for the planned variation in genes between the loxP sites.

Corn immature embryos were transformed with these constructs by a modified *Agrobacterium*-mediated transformation procedure, as described in (Djukanovic et al., 2006). Eight to 10 day embryos were dissected from sterile kernels and placed into liquid medium (4.0 g/l N6 Basal Salts (Sigma C-1416), 1.0 ml/l Eriksson's Vitamin Mix (Sigma E-1511), 1.0 mg/l thiamine HCl, 1.5 mg/l 2, 4 D, 0.690 g/l L-proline, 68.5 g/l sucrose, 36 g/l glucose, pH 5.2). After embryo collection, the medium was replaced with 1 ml of *Agrobacterium* suspension at concentration of 0.175-0.45 OD at 550 nm. After incubating for five minutes at room temperature, the embryo suspension was poured onto a plate containing 4.0 g/l N6 Basal Salts (Sigma C-1416), 1.0 ml/l Eriksson's Vitamin Mix (Sigma E-1511), 1.0 mg/l thiamine HCl, 1.5 mg/l 2, 4 D, 0.690 g/l L-proline, 30.0 g/l sucrose, 0.85 mg/l silver nitrate, 0.1 nM acetosyringone, 3.0 g/l Gelrite, pH5.8). Embryos were incubated in the dark for 3-5 days at 21° C. followed by 3-7 days incubation in the dark at 28° C. on new plates containing 4.0 g/l N6 Basal Salts (Sigma C-1416), 1.0 ml/l Eriksson's Vitamin Mix (Sigma E-1511), 1.0 mg/l thiamine HCl, 1.5 mg/l 2, 4 D, 0.690 g/l L-proline, 30.0 g/l sucrose, 0.5 g/l MES, 0.85 mg/l silver nitrate, 100 mg/l carbenicillin, 9.0 g/l agar, pH 5.8). Embryos are then transferred onto new plates containing 4.0 g/l N6 Basal Salts (Sigma C-1416), 1.0 ml/l Eriksson's Vitamin Mix (Sigma E-1511), 1.0 mg/l thiamine HCl, 1.5 mg/l 2, 4 D, 0.690 g/l L-proline, 30.0 g/l sucrose, 0.5 g/l MES, 0.85 mg/l silver nitrate, 1.5 mg/l bialaphos, 100 mg/l carbenicillin, 6.0 g/l agar, pH 5.8, for 3-4 weeks. After 3-4 weeks on the first selection medium, embryos were sub-cultured every 2-4 weeks on 4.0 g/l N6 Basal Salts (Sigma C-1416), 1.0 ml/l Eriksson's Vitamin Mix (Sigma E-1511), 1.0 mg/l thiamine HCl, 1.5 mg/l 2, 4 D, 0.690 g/l L-proline, 30.0 g/l sucrose, 0.5 g/l MES, 0.85 mg/l silver nitrate, 3 mg/l bialaphos for moPAT selection, 100 mg/l carbenicillin, 6.0 g/l agar, pH 5.8 until transgenic events were identified. Regeneration was induced by transferring small sectors of tissue onto maturation media containing 4.3 g/l MS salts (Gibco 11117: Gibco, Grand Island, NY), 5.0 ml/l MS Vitamins Stock Solution, 100 mg/l myo-inositol, 0.1 µM ABA, 0.5 mg/l zeatin, 1 mg/l IAA, 60.0 g/l sucrose, 3.0 mg/l bialaphos, 100 mg/l carbenicillin, 6.0 g/l Agar, pH 5.6). The plates were incubated in the dark for two weeks at 28° C. Somatic embryos were transferred onto media containing 4.3 g/l MS salts (Gibco 11117: Gibco, Grand Island, NY), 5.0 ml/l MS Vitamins Stock Solution, 100 mg/L myo-inositol, 40.0 g/l sucrose, 3.0 mg/l bialaphos, 6.0 g/l Agar, pH 5.6, and incubated under artificial light at 28° C. One week later, plantlets were moved into glass tubes containing the same medium and grown until they were sampled and/or transplanted to soil.

Following exploratory work using maize inbred line 1 and relatively limited numbers of insertions with available flanking sequence data, another maize inbred line (Maize Inbred line 2) was chosen to continue and extend this work. MI2 was chosen for a combination of superior genetics compared to maize inbred line 1 and comparable transformation efficiency. Collection of a larger number of maize inbred line 2 transgenic target sites with flanking sequence data was a primary goal. Constructs and molecular methods used to develop this new collection of transgenic target sites were similar to MI1, but the transformation methods varied especially in the formulation of the tissue culture medium. The tissue culture methods for MI2 can be found in Cho, M J et al., 2011 (US20110165561) and in more detail in Wu, X. E. et al, (US20100192253). Similar methods were used for both maize inbred lines to recover transgenic plants to the greenhouse, sampling, and downstream handling.

Transgenic plants (target lines) were analyzed for T-DNA copy number and for transgenic target site genomic flanking sequence. Real time quantitative PCR (qPCR) was used to assess the copy number of the T-DNA. A high quality transgenic target site was defined as one that is present as a single copy in the transgenic plant and one which included no extra sequence from the *Agrobacterium* vector beyond the T-DNA left or right borders (RB, LB). One specific, independent qPCR assay was developed for each gene within the T-DNA borders of each construct. In addition, multiple qPCR assays were used to detect unique sequences of the *Agrobacterium* constructs outside of the T-DNA borders, often referred to as vector backbone sequence. If all of the genes inside the T-DNA were scored as single copy from the qPCR analysis and there were no vector backbone sequences detected, then the transgenic target site was described as a single copy transgenic target site (single copy insertion). Those transgenic plants with single copy transgenic target sites were advanced to the greenhouse and used in further analyses. Each independent single copy transgenic target site from the corn SSI library was viewed as a unique entity and a potential candidate for site specific integration.

Transgenic plants containing single copy T-DNA insertions were sampled as a first or second generation transgenic plant for flanking sequence analysis in order to begin further characterization of the transgenic target site. Multiple leaf samples were taken from each plant and pooled for DNA extraction. DNA was extracted by using Omega Bioteck E-Z 96 Plant DNA Kit following manufacturer's recommendations. Flanking sequence analysis was done either by inverse PCR (IPCR) or ligation-mediated nested PCR (LMnPCR) (FIG. 4) followed by sequencing of the PCR products. Site specific primers were designed to amplify just inside the T-DNA RB and LB for both of these methods. If IPCR was used, genomic DNA samples were digested with 4-8 different restriction enzymes which cut once in the T-DNA sequence near the outside primer binding site. The enzymes can cut once at unknown sites in the genomic sequence outside of but proximal to the transgenic target site and many other sites in the genome. The DNA fragments with like restriction cuts on each end were then placed in a ligation reaction to obtain self-ligation to generate small DNA circles consisting of a portion of the T-DNA and a section of genomic DNA. Nested PCR was performed with outward facing primers designed at each end of the T-DNA sequence of the mini-circles. PCR can amplify a product that contains the ends of the T-DNA sequence and the adjoining genomic sequence of the transgenic target site (flanking sequence). The small volume of PCR product was treated with ExoSAP to clean-up the remaining primers and dNTPS and then the cleaned amplicon was sequenced using the Sanger method. If LMnPCR methods were used genomic DNA was mechanically sheared into smaller fragments and the ends of fragments were converted into blunt ends using Klenow fragment with 3' to 5' exonuclease activity. Next the fragments were processed by dA-tailing at 3' ends to prevent blunt-end fragment ligation and provided a complementary overhang for ligation of the adaptor to the fragments. If the amplicon was sequenced using the Sanger method, then the adapter was ligated onto the fragments and nested PCR was performed with adapter specific primers and primers designed to the T-DNA border sequences. If the amplicon was sequenced using the Solexa method, then indexed adapters were ligated to the ends of the DNA fragments for pooled amplicon sequencing and run on a 2100 Bioanalyzer using a DNA specific chip to check the size and concentration of the product. Sequence results from Solexa were deconvoluted, compared, and evaluated by using only the best quality reads where confidence was high in the individual base calls. Finished sequence data was used in BLAST analysis against the whole maize genome sequence. This approach resulted in predictions for which of the 10 corn chromosomes the transgenic target site was located on and associated data from that region of the chromosome such as genetic position of the transgenic target sequence for SSI and markers at that location. Not all of the samples were able to be resolved in this manner but approximately 70% of total samples were able to be assigned to a specific chromosome based on the sequence data from at least one of the T-DNA borders following first pass analysis (Table 1A and 1B). A subset of the transgenic target sites with detailed BLAST analysis was predicted to be interrupting endogenous genes. Transgenic target sites that interrupted endogenous genes were viewed as undesirable and discarded. Seeds from events comprising the remaining transgenic target sites were kept as seed in a collection that could be readily accessed when desired. An early name given to this collection was 'insertion site library' which referred to the relatively large number of samples characterized, the transgenic target site distribution which encompassed all 10 maize chromosomes, and the subsequent seed collection which allowed us to access specific sites in the maize genome on demand.

TABLE 1A

Sample numbers and flanking sequence results for maize inbred line 1.

| Sample Description (based on flanking sequence results) | Sample No. |
|---|---|
| Single copy insertions submitted for flanking sequence | 494 |
| Flanking sequence results obtained | 477 |
| Flanking sequence assigned to a chromosome | 329 |
| Transgenic target sites predicted to be interrupting an endogenous gene | 172 |
| Samples with both T-DNA borders resolved | 405 |
| Samples with both T-DNA borders in repetitive sequence | 46 |

TABLE 1B

Sample numbers and flanking sequence results for maize inbred line 2.

| Sample Description | Sample No. |
|---|---|
| Quality insertions submitted for flanking sequence | 1286 |
| Flanking sequence results obtained | 1157 |
| Flanking sequence assigned to a chromosome | 810 |
| Transgenic target sites predicted to be interrupting an endogenous gene | 420 |
| Samples with both T-DNA borders resolved | 347 |
| Samples with both T-DNA borders in repetitive sequence | 81 |

Obtaining flanking sequence data for single copy transgenic target sites and being able to get back to the transgenic material through the seed collection are the first steps in the process toward advancing them into site specific integration work and building complex trait loci. The initial flanking sequence data was generated for a large number of transgenic plants by relatively rapid screening. When one of the T-DNA border regions did not resolve or there was a conflict between results for the RB and LB, the plant was still maintained for the collection. If no flanking sequence (FS) results were obtained for a plant, then that plant was discarded from the collection. When an transgenic target site from the library was identified that was in a region of interest (also referred to as a genomic locus of interest) in the maize genome then the seed of that plant was grown out and samples were re-submitted for flanking sequence analysis. Once a confirmation of the original flanking sequence was obtained, additional work including Southern analysis to verify qPCR results and SSI transformation work to characterize frequency for the site was initiated. If a transgenic target site for SSI passed Southern analysis to confirm that there was a single intact copy of the T-DNA and no vector backbone, and it was demonstrated to undergo SSI, then it became a recombinant target locus (RTL) and was assigned a unique identifier. RTLs were advanced further for characterization of gene expression and agronomics. Currently more than 1000 transgenic target sites have been identified spanning all of the maize chromosomes.

Example 2

Production of a Complex Trait Locus (CTL3A) at Chromosome 1

One valuable region of the corn genome, referred to as Complex Trait Locus 3A (CTL3A; FIG. 5a), was identified containing a trait of interest (Trait 3A) on chromosome 1 as follows.

Identification of Trait of Interest

The location of Trait3A on chromosome 1 was determined based on sequence homology following determination of the transgenic target site flanking sequence and then verified by mapping data. Transgenic target site flanking sequence (FS) was obtained by using inverse PCR (IPCR) and amplified DNA products were sequenced using the Sanger sequencing method. Once sequence was obtained, the results were compared to the maize whole genome sequence using the BLAST algorithm to match FS data to maize genome sequence. The maize genome sequence was assembled into subset sequences for each individual chromosome so that BLAST analysis could be used to predict the location of the FS to a chromosome. The maize genetic map was associated with the chromosome sequence based on DNA marker sets and this allowed a position on the chromosome to be identified for a particular FS. Finally, the chromosome and position of the Trait3A insertion that was initially determined using bio-informatics was verified by mapping the transgenic target site.

Identification of Transgenic Events Comprising Transgenic Target Sites (TTS) Located Near the Trait of Interest In order to develop a Complex Trait Locus at the Trait3A location, one or more independent transgenic loci in close genetic proximity of Trait 3A on the corn genome needed to be generated. These independent transgenic loci can then be combined by breeding or re-transformation and can segregate in subsequent breeding steps as a single genetic locus (as described in FIG. 1).

A set of 8 SSI platform II constructs was used to generate maize inbred line 1 (MI1) transgenic plants (containing independent transgenic loci) as described in Example 1 (Table 1A). There were 50 to 100 transgenic plants with single copy T-DNA insertions generated for each of the 8 constructs. Leaf samples from most of these transgenic plants were submitted for flanking sequence analysis and the final set of results included nearly 500 transgenic individuals. Approximately 67% (329/494) of the transgenic plants submitted gave sequence results that could be associated with one of the ten maize chromosomes following bio-informatics analysis involving the BLAST algorithm (data not shown). Those that could not be associated to a maize chromosome were either failed samples of the flanking sequence method or samples with sequence results included only in repetitive genome sequence. Each construct provided multiple transgenic target sites for SSI that were distributed across each of the 10 corn chromosomes.

FIG. 5A shows transgenic target sites identified on Chromosome 1 near two transgenic traits of interest, Trait3A and Trait3C. Each individual (single border) or pair (both borders) of triangles and bars across the chromosome indicates unique transgenic target sites. FIG. 5A shows 15 transgenic target sites mapped to chromosome 1. The transgenic target sites of Trait3A and Trait3C were mapped to chromosome 1 using primarily a bio-informatics approach. Using flanking sequence results from our library of approximately 500 SSI platform II insertions in maize inbred 1 (individual transgenic events), 4 independent transgenic target sites for site specific integration (TTS-3A1, TTS-3A2, TTS-3A3, TTS-3A4) were identified that could be located very near (plus or minus approximately 5 centi-Morgans) to the Trait3A locus (also referred to as the genomic locus of interest) and together could comprise the Complex Trait Locus 3A (CTL3A) if properties of each transgenic target site warranted further development. In addition, an insertion site (IS) (IS-3A5, also referred to as MHP14, see U.S. Provisional Patent Application No. 61/466,602, filed on Mar. 23, 2011) was developed in this region using homing endonuclease technology and recombination. Each of these TTSs or IS (TTS3A1-TTS3A4 and IS3A5) can be used independently or in combination with Trait3A and physically linked by crossing with Trait3A. The resulting complex trait locus can be introduced into a breeding program acting as a single genetic locus.

The 4 transgenic events representing the 4 transgenic target sites surrounding Trait3A were selected for follow up work including additional characterization undertaken prior to complex trait locus formation. Seed was not available for the transgenic lines representing TTS-3A1, while transgenic lines representing TTS-3A3 and TTS-3A4 were predicted to interrupt endogenous genes and were therefore undesirable for complex trait locus development and therefore abandoned. The transgenic line comprising TTS-3A2 (also referred to as insertion site 98281928) was generated using an *Agrobacterium* vector derived from SSI platform II intermediate that was closely related to PHP35557 (FIG. 2) except that it incorporated the Invitrogen™ Gateway® destination site for Gateway® cloning.

Table 2 shows the public IBM2 genetic map position (IBM genetic map data available through the MaizeGDB website) as well as the map position of an internally derived single meiosis map (PHB) for a multitude of markers, transgenic target sites and insertion sites (TTSs and IS highlighted in gray). PHB is a genetic map based on a population that has undergone one round of meioses (e.g. an $F_2$) whereas the IBM2 map consist of multiple meioses. TTS-3A6 is also referred to as insertion site 148053664, TTS-3A7 is also referred to as insertion site 152323453, TTS-3A8 is also referred to as insertion site 154587278, TTS-3A9 is also referred to as insertion site 153175440, and TTS-3A10 is also referred to as insertion site 148016489.

Table 2 shows that the Trait3A insertion resides at IBM position 134.66 in bin 1.02. Transgenic target site TTS-3A2 and insertion site IS-3A5 were identified from MI1 and an additional 5 TTS sites (TTS-3A6, TTS-3A7, TTS-3A8, TTS-3A9, TTS-3A10) near the Trait3A genomic locus of interest were identified from our MI2 collection. One of the events comprising TTS-3A7 (Table 2) was advanced for further characterization.

TABLE 2

Complex Trait Locus CTL-3A on Chromosome 1 of corn.

| Locus | IBM Position | PHB position |
|---|---|---|
| UMC1160 | 108.3 | 44.1 |
| UMC2224 | 110.9 | 45.2 |
| NPI579B | 112.2 | 45.9 |
| PMCB1 | 115.2 | 46.6 |
| TTS-3A2 | 116.2 | 49.6 |
| TTS-3A6 | 116.9 | 50.4 |
| IDP3917 | 117.0 | |
| GPM199C | 117.2 | |
| TTS-3A7 | 119.5 | 51.0 |

TABLE 2-continued

Complex Trait Locus CTL-3A on Chromosome 1 of corn.

| Locus | IBM Position | PHB position |
|---|---|---|
| TTS-3A8 | 119.5 | 51.0 |
| IDP1425 | 119.7 | |
| MMP68 | 123.6 | 51.5 |
| UMC2225 | 124.7 | 52.0 |
| STD2C(DBA) | 125.3 | |
| IS-3A5 | 125.3 | 52.1 |
| TIDP3300 | 125.4 | |
| CSU1171 | 127.3 | 53.2 |
| SUT1 | 133.6 | |
| UMC1166 | 133.6 | |
| TRAIT3A | 138.6 | 55.0 |
| AY107207 | 139.4 | |
| UMC1568 | 141.8 | 54.1 |
| IDP3783 | 141.8 | |
| TTS-3A9 | 142.1 | 58.0 |
| TTS-3A10 | 142.5 | 59.1 |
| BNLG1429 | 143.5 | 57.8 |
| IDP209 | 146.0 | 58.1 |
| LTK1 | 148.0 | 58.6 |
| IDP7169 | 153.2 | 63.3 |

FIG. 6 shows a schematic of the transgenic target sites of the CTL3A complex trait locus in relation to the genomic window of interest (TRAIT3A) and public BAC S on the maize physical map.

Site Specific Integration in Transgenic Maize Event Comprising TTS-3A2

The transgenic event representing TTS-3A2 (Table 2 and FIG. 6) was further evaluated by testing its capability for site specific integration of genes of interest. Each FRT site of the event (FRT1 and FRT87), and some DNA sequence downstream and upstream of the transgenic target site were amplified by PCR using oligonucleotide primers homologous to sequence of the T-DNA directly adjacent to the FRT sites on both sides. The PCR products were purified by agarose gel electrophoresis. A band with the expected size of the predicted PCR product was cut from the gel, extracted, submitted for DNA sequencing and the FRT target site sequence was confirmed to be intact. This data confirmed that SSI with TTS-3A2 would not be impeded by the FRT sites since they were intact and demonstrated the expected sequence result.

Particle bombardment was used as the method of DNA delivery for SSI transformation. A 'donor plasmid' containing a sequence of interest flanked by FRT sites was delivered into heterozygous immature embryos containing TTS-3A2 via biolistic-mediated transformation. Nine toll day-old immature embryos (1-1.5 mm in size) were dissected from sterilized kernels and plated with their axis down to media containing 4.0 g/l N6 Basal salts (Sigma C-1416) 1.0 ml/l Eriksson's Vitamin Mix (Sigma E-1511). 1.0 mg/l thiamine HCl, 1.5 mg/l 2,4-D, 0.690 g/l L-proline, 30 g/l Sucrose, 0.85 mg/l silver nitrate, 3.0 g/l Gelrite, pH 5.8 and incubated in the dark at 28° C. for 3 to 5 days before introduction of DNA. Two to four hours prior to bombardment the embryos were plasmolized by placing them on the above media containing 120 gm of sucrose.

Plasmid DNA was associated with the gold particles by mixing 50 ng of PHP27064, 10 ng of PHP5096 (UBI: FLPm), 25 ng of the helper plasmid PHP31729 (OLE PRO:ODP2), and 25 ng of the helper plasmid PHP21139 (IN2 PRO:WUS) (volume of the DNA solution was adjusted to 40 µl), 50 µl of 1-µm gold particles at 0.01 mg/µl and 5 µl TFX-50 (Promega E1811/2) (FIG. 7). SSI could be completed using only PHP27064 and PHP5096, but earlier experiments (data not shown) showed that inclusion of plasmids with the genes on PHP21139 and PHP31729 increased SSI frequency. These additional genes help to stimulate cell division in culture and may enhance recombination (see U.S. Patent Publication No. US20110165679A1). The particle/plasmid solution was allowed to gently mix for 10 minutes. The particles and attach DNA were then spun down for 1 minute at 10,000 rpm, the supernatant removed and replaced with 120 µl of 100% ethanol. The particles were then re-suspended by gentle sonication, 10 µl of the particle solution was spotted on each carrier disc and the EtOH was allowed to evaporate. The macro carrier was placed 2.5 cm from a 450 psi rupture disc with the immature embryos placed on a shelf 7.5 cm below the launch assembly.

After bombardment the embryos were removed from the high sucrose media and placed back on same medium containing 30 g/l sucrose. The embryos were incubated in the dark at 28° C. for 7 days at which time the embryos were moved to selection plates of the above media containing 0.1778 mg/l glyphosate. Embryos were subcultured to fresh medium after 3 weeks; transgenic events were identified 4 weeks later. Transgenic events growing under selection were then observed for their yellow fluorescent protein positive phenotype. Those that exhibited a fluorescent phenotype indicative of RMCE were regenerated using glyphosate as the selective agent at the same levels presented above. Plantlets were sampled and/or transplanted to soil.

The expected result is shown in FIG. 8 as Target with RMCE.

A series of qPCR assays were used to indicate that SSI had occurred including checking the copy number of each gene between the FRT sites that originally resided in the target and donor plasmids as well as detection assays for the other co-bombarded plasmids. In order to obtain these results DNA was extracted from leaf samples of regenerated plants via a modified alkaline lyses method using 1 punch (200 ng) of fresh leaf tissue (Truett et al., 2000). For real-time quantitative PCR (qPCR), each gene was quantitated using proprietary forward and reverse primers along with a corresponding FAM based probe. Each assay was primer titrated and normalized to an amplification signal from a single copy native sequence which was detected by a second distinct primer set and VIC-based probe. Each amplification reaction for determination of copy number of the HT (Herbicide tolerance), YFP, and MO-PAT genes were run simultaneously with the normalizing gene in a single tube reaction. Upon completion of the qPCR, all raw data were used to calculate the dCT values. Copy number determination was computed with the $\Delta\Delta CT$ method as described in the ABI (Applied Biosystems, Foster City, CA) user bulletin #2. Endpoint positive and negative qPCR calls were made for FLP, ODP2, WUS, and the two recombinant junction assays (UBI-FRT1-HT, donor-FRT87-target) according to the dCTs estimations. A qPCR reaction running 5 cycles later than the native normalizing sequence was called negative.

There were approximately 1400 immature embryos heterozygous for Insert 1 that were co-bombarded using the donor plasmid, PHP27064, and the SSI associated plasmids with FLP recombinase, ODP2, and WUS (FIG. 7). Bombarded embryos were transferred to selective culture medium as described above and then cultured for callus growth. Callus growing in the presence of glyphosate and showing a yellow fluorescent phenotype when viewed under a dissecting microscope with the appropriate light source and filters was advanced for plant regeneration. Two independent calli with these properties were advanced into regeneration, regenerated plants were recovered, and leaf samples from the plants submitted for qPCR. The set of qPCR assays run included assays that span the FRT1 and FRT87 recombinase sites and include primers designed to both target (Insertion 2) and donor sequence to yield the result (Table 3). A positive (POS) call for FRT1 and FRT87 indicate that SSI has occurred. Additional assays were run to assess the quality of the SSI. Copy number assays were run for the genes in the donor, HT and YFP, to determine whether additional copies of the donor plasmid were randomly inserted. Assays for ODP2, WUS, and FLP were run for the same reason and the best results were negative for ODP2 and FLP and 1 copy for WUS (assay detects endogenous WUS gene). The last assay was a detection method for the gene in the target sequence, PAT, which should have been removed as a result of site specific integration. The cumulative results of this analysis showed that SSI had occurred in both recovered calli and that undesirable integration of the co-bombarded plasmids was unlikely (Table 3). Southern analysis can be used for the further confirmation, but the qPCR analysis is a valuable initial screen. The SSI frequency obtained for TTS-3A2 was 0.14% based on the total embryo number.

multiple qPCR assays which showed replacement of the mopat gene by the cassette with the HT and YFP genes and no integration of the intact plasmids that had been co-bombarded with the donor plasmid.

Generating a Transgenic Plant Containing the Complex Trait Loci 3A

In order to build the complex trait locus 3A, additional trait genes can be inserted into TTS-3A2 of IE-2. The resulting transgenic plant containing the additional trait genes in TTS-3A2 can then be crossed (or re-transformed) with transgenic events containing the Trait3A (as illustrated in FIG. 1). The addition of trait genes at TTS-3A2 can be accomplished by developing a donor plasmid with MO-PAT in the gene trap position and trait genes downstream of the marker gene and then repeating the transformation protocol detailed above except that bialaphos or phosphinothricin would replace glyphosate as the selection agent in tissue culture and qPCR assays would match the mo-pat gene.

TTS-3A2 was predicted to be 3.6 cM away from Trait3A (Table 2) based on an internally derived single meiosis genetic map (PHB), indicating a 100% chance of finding at least 1 recombinant in 400 progeny. Crosses have been made to link TTS-3A2 with Trait3A.

Related work with another transgenic target site in the same region and located closer to Trait3A was completed. This insertion site IS-3A5 (also referred to as MHP14), was

TABLE 3 qPCR analysis of regenerated plants from two glyphosate resistant, yellow fluorescent calli from the event comprising TTS-3A2. This analysis was used to detect SSI and the presence of plasmids including PHP21139, PHP5096, PHP31729, and PHP27064.

| Callus No. | Plant No. | YFP Pheno. | FRT1 | FRT87 | HT COPY | YFP COPY | PAT | ODP2 | WUS | FLP |
|---|---|---|---|---|---|---|---|---|---|---|
| 1 | 1 | POS | POS | POS | 1 | 1 | NEG | NEG | 1 | NEG |
| 1 | 2 | POS | POS | POS | 1 | 1 | NEG | NEG | 1 | NEG |
| 1 | 3 | POS | POS | POS | 1 | 1 | NEG | NEG | 1 | NEG |
| 1 | 4 | POS | POS | POS | 1 | 1 | NEG | NEG | 1 | NEG |
| 1 | 5 | POS | POS | POS | 1 | 1 | NEG | NEG | 1 | NEG |
| 1 | 6 | POS | POS | POS | 1 | 1 | NEG | NEG | 1 | NEG |
| 2 | 1 | POS | POS | POS | 0.5 | 0.5 | NEG | NEG | 1 | NEG |
| 2 | 2 | POS | POS | POS | 0.5 | 0.5 | NEG | NEG | 1 | NEG |
| 2 | 3 | POS | POS | POS | 0.7 | 0.6 | NEG | NEG | 1 | NEG |

POS = Positive.
NEG = Negative.
YFP = yellow fluorescent protein (ZS-Yellow1 N1, Clontech).
HT = Herbicide tolerance gene.
ODP = ovule development protein.
WUS = wuschel.
FLP = flp recombinase.

In summary of the work above, a transgenic event containing TTS-3A2 was generated using a construct derived from the SSI platform II vector intermediate and referred to as IE-2. The transgenic target site was characterized as a quality insertion using qPCR analysis during the transformation process. Leaf samples from IE-2 were submitted for flanking sequence analysis. The resulting flanking sequence data was used to estimate its genomic position very near to Trait3A on chromosome 1. Later mapping data confirmed the chromosome 1 location initially estimated using flanking sequence data. IE-2 was further characterized for use in SSI transformation experiments by confirmation of intact FRT site sequence. Next, the process of SSI transformation was initiated to determine a frequency of obtaining recombinase mediated cassette exchange (RMCE) from IE-2. Transgenic plants showing the correct phenotype for SSI were recovered from these experiments. SSI was verified by using generated by meganuclease assisted homologous recombination (described in U.S. Provisional Patent Application No. 61/466,602, filed on Mar. 23, 2011) (FIG. 5A, Table 2). The site was predicted to be less than 2 cM away from Trait3A based on an internally derived single meiosis genetic map (PHB) (Table 2). The breeding scheme for physical linkage should work for any 2 insertion sites or genomic points of interest (transgenic insertions, native traits, QTL's, haplotypes, chromosomal regions of interest, etc.), or combinations of the two (Table 4). Briefly, an F1 plant is created by cross pollination of two plants homozygous for the entities that need to be linked. F1 kernels are germinated and screened by qPCR or another molecular method to verify that both are present in the F1. When the F1 plant is flowering, then pollen is carried from the F1 to a non-transgenic recipient plant or a line that does not carry the entities to be linked. Progeny from that cross are screened for individuals that carry both entities and they should be linked at that point from recombination that took place during pollen formation of the F1 plant. The individuals identified to have both entities are then self-pollinated and the progeny will segregate 1:2:1 (1 homozygous: 2 heterozygous: 1 null) for the two entities together. The 1:2:1 segregation ratio at this final breeding step confirms that the two entities are physically linked at a single genetic locus.

TABLE 4

Breeding scheme for selection of linked transgenic target sites or other entities and confirmation of linkage.

| GEN. | Materials | Genetic Status | Breeding Step | Result |
|---|---|---|---|---|
| 1 | Entity 1, Entity 2 | Homozygous for one locus each | Entity 1 × Entity 2 | F1 (1, 2) not linked |
| 2 | F1, Entity free line | F1 heterozygous for both loci | Entity Free × F1 (female × male) | F2 (1, 2, 1:2, null) (1:2 linked) |
| 3 | F2 | Heterozygous linked screen. | F2 (1:2) Self pollinated | F3 (1:2, null) |
| 4 | F3 | Single locus entity 1: entity 2 | None | 1:2:1 (1:2, null) (homo:hemi:null) |

GEN. = Plant generation.

Seed comprising the IS-3A5 and Trait3A were planted in subsequent weekly plantings and the plants matured to flowering stage. At flowering, plants with IS-3A5 were used as a pollen source and crossed with the transgenic plants containing the Trait3A, thereby creating a CTL3A complex trait locus.

Ears were harvested from these crosses, dried down, and F1 kernels removed. The F1 kernels were planted and the resulting plants were screened as seedlings by qPCR to confirm that both transgenic loci were present. At the same time the IS-3A5/Trait3A kernels were planted, kernels of another suitable non-transgenic line were planted to act as a female in crosses with the F1 transgenic line. As these plants flowered, pollen from the IS-3A5/Trait3A transgenic F1 was carried to ears of the non-transgenic line. Filled ears from these crosses were processed and resulting F2 kernels planted in flats to screen for recombinants between IS-3A5 and Trait3A. This screening was based on qPCR analysis with two assays specific to Trait3A and one assay specific to IS-3A5. In total, 813 F2 plants were screened resulting in 419 positive for CTL3A only, 387 positive for IS-3A5 only, and 7 plants that were positive for both transgenic loci. Assuming the 7 double positive were all recombinants as expected, the frequency is 0.9% indicating that IS-3A5 is approximately 1 cM away from CTL3A. These 7 plants were grown up and self-pollinated and the rest of the F2 progeny discarded. Confirmation of the linkage of IS-3A5 and Trait3A in these 7 plants included analysis of the progeny from the self-pollination. Both transgenic loci would segregate 1 homozygous:2 heterozygous:1 null if they were linked at one locus. Leaf samples from progeny of one of the seven self-pollinated F2 plants were taken for qPCR analysis. Two of the qPCR assays, MHP14 HR1 and CTL3A, were designed for detection only and not to indicate copy numbers of the amplicon sequences. Two additional qPCR assays, MHP14 IS and CTL3A gene 3, were developed to indicate the copy numbers of the amplicon (Table 5). The transgenic insertion at the IS-3A5 target site excludes detection by the qPCR assay. If the insertion was not present, the qPCR was positive and the locus is designated as wild type (wt). The MHP14 IS assay is quantitative and a result with 2 wt alleles indicated that the IS-3A5 transgenic insertion was not present. The Trait3A GENE3 assay was designed in the open reading frame sequence of one of the genes in the CTL3A stack. It is a quantitative assay such that a 2 copy call indicated that the donor plant was homozygous for Trait3A and a 1 copy call is heterozygous. The other two assays, MHP14 HR1 and Trait3A, did not indicate the number of insertion copies but supported the copy number calls with positive/negative indications for related elements. For example, a homozygous plant for both transgenic alleles would have 0 wt copies of the MHP14 IS, be positive for the presence of MHP14 HR1, contain two copies of Trait3A GENE3, and would be positive for the distinct additional assay for the CTL3A insertion (Table 5). In conclusion, the analysis demonstrated that there were 8 homozygous:16 heterozygous:7 null and this matched the expected result for two transgenes linked at a single genetic locus. This confirmed our ability to link the two loci into a single trait locus on chromosome 1 and create a Complex trait Loci 3A.

TABLE 5 qPCR analysis of progeny from a self-pollination of a single F2 plant with two transgenic loci, IS-3A5 (MHP14) and CTL3A.

| Number Plants | MHP14 IS | MHP14 IS CALL | MHP14 HR1 | CTL3A GENE 3 | CTL3A |
|---|---|---|---|---|---|
| 8 | 0 | No wt alleles | positive | 2 copy | positive |
| 16 | 1 | 1 wt allele | positive | 1 copy | positive |
| 7 | 2 | 2 wt alleles | negative | negative | negative |

Example 3

Production of a Complex Trait Locus (CTL6A) on Chromosome VI

Another valuable region of the corn genome, referred to as Complex Trait Locus 6A (CTL6A; FIG. 5b), was identified containing a trait of interest (Trait 6A) on chromosome VI as follows.

Identification of Trait of Interest

The genetic map position of Trait6A on chromosome VI was determined based exclusively by trait mapping data obtained during the process of inbred conversions and trait integration.

Identification of Transgenic Events Comprising SSI Target Sites Located Near the Trait of Interest In order to develop a Complex Trait Locus at the Trait6A location, one or more independent transgenic loci in close genetic proximity of Trait6A on the corn genome needed to be generated. These independent transgenic loci can then be combined by breeding or re-transformation and can segregate in subsequent breeding steps as a single genetic locus (as described in FIG. 1).

Initial screening of the flanking sequence data for transgenic insertions from maize inbred line 1 (MI1) resulted in the identification of four transgenic target sites (TTS-6A1, TTS-6A2, TTS-6A3, TTS-6A4) near Trait 6A (FIG. 5B). Bars across the chromosome indicate unique insertion sites and represent potential members of the Complex Trait Locus 6A (CTL6A). Each of these 4 TTSs can be used independently or in combination with Trait6A and physically linked by crossing with Trait6A. Seed was obtained from a transgenic event containing the TTS-6A3 site (FIG. 5B, arrows), referred to as IE-7, and a transgenic event containing TTS-6A4 (FIG. 5B, arrows), referred to as IE-8. IE-8 was dropped due to the presence of extra bands in Southern analysis. TTS-6A3 is also referred to as 97757511 and TTS-6A4 is also referred to as 97757502.

The genetic map position was used in combination with the physical map to identify MI2 insertion sites that were predicted to be within 5 cM on either side of Trait6A (FIG. 9). The maize genetic map facilitated the association with the chromosome sequence and DNA marker sets Table 6A shows the public IBM2 genetic map position (IBM genetic map data available through the MaizeGDB website) as well as the map position of an internally derived single meiosis map (PHB) for a multitude of markers and transgenic target sites (insertion sites; TTSs highlighted in gray). PHB is a genetic map based on a population that has undergone one round of meioses (e.g. an $F_2$) whereas the IBM2 map consist of multiple meioses. TTS-6A5 is also referred to as insertion site 145401580, TTS-6A6 is also referred to as insertion site 124537396, TTS-6A7 is also referred to as insertion site 148174073, TTS-6A8 is also referred to as insertion site 145401461, TTS-6A9 is also referred to as insertion site 148304686, TTS-6A10 is also referred to as insertion site 147136301, TTS-6A11 is also referred to as insertion site 145403827, TTS-6A12 is also referred to as insertion site 145403004, TTS-6A13 is also referred to as insertion site 149743000, and TTS-6A14 is also referred to as insertion site 148293657.

Table 6A shows that the Trait6A insertion resides at IBM position 113.62, PHB position 23.70. Transgenic target sites TTS-6A3 was identified from MI1 and an additional 10 TTS sites (TTS-6A5, TTS-6A6, TTS-6A7, TTS-6A8, TTS-6A9, TTS-6A10, TTS-6A11, TTS-6A12, TTS-6A13, and TTS-6A14) near the Trait6A genomic locus of interest were identified from our MI2 collection.

TABLE 6A

Complex Trait Locus CTL-6A on Chromosome 6 of corn.

| LOCUS | IBM location | PHB location |
| --- | --- | --- |
| UMC1625 | 86.20 | 16.72 |
| TTS-6A5 | 76.75 | 18.40 |
| TTS-6A6 | 77.15 | 18.50 |
| UMC2196 | 86.40 | 18.73 |
| TTS-6A7 | 91.03 | 19.90 |
| UMC2312 | 75.80 | 21.38 |
| BNLG1867 | 78.30 | 21.49 |
| PZA03047 | 84.50 | 21.68 |
| UMC1229 | 80.70 | 22.30 |
| UCK1 | 96.00 | 22.76 |
| RZ390D(CYB5) | 85.50 | 22.79 |
| MMP20 | 105.90 | 22.80 |
| MMP10 | 110.40 | 22.83 |
| MMP160 | 101.90 | 22.86 |
| PHP20528 | 85.50 | 23.04 |
| UMC2314 | 99.30 | 23.10 |
| UAZ232B(SCI) | 100.30 | 23.38 |
| UMC2313 | 91.90 | 23.56 |
| TTS-6A8 | 112.25 | 23.60 |
| TTS-6A9 | 113.62 | 23.70 |
| TRAIT 6A | | 23.70 |
| CDO545 | 86.90 | 24.72 |
| PHP20854 | 87.70 | 24.72 |
| UMC1133 | 98.60 | 24.72 |
| UFG69 | 104.80 | 24.72 |
| TTS-6A10 | 114.92 | 23.80 |
| TTS-6A11 | 114.92 | 23.80 |
| TTS-6A12 | 119.31 | 24.90 |
| TTS-6A13 | 119.53 | 25.00 |
| MMP76 | 103.80 | 25.03 |

TABLE 6A-continued

Complex Trait Locus CTL-6A on Chromosome 6 of corn.

| LOCUS | IBM location | PHB location |
| --- | --- | --- |
| TTS-6A14 | 120.43 | 25.50 |
| TTS-6A3 | 122.77 | 26.30 |
| Y1 | 120.50 | 26.81 |
| BNLG1422 | 121.10 | 26.87 |
| MMP108B | 118.30 | 26.93 |
| MMP4 | 116.20 | 27.18 |
| UMC1006 | 125.00 | 27.94 |
| RZ444E | 123.70 | 31.76 |

FIG. 9 shows the location of the insertion sites TTSs of the CTL6A complex trait locus in relation to public BACS on the maize physical map of maize.

TABLE 6B

Confirmation of successful site specific integration at different loci comprising the CTL6A. Yes indicates that the target site locus was shown to be capable of site specific integration.

| Locus | IBM Location | PHB Location | SSI Confirmed |
| --- | --- | --- | --- |
| TTS-6A5 | 76.75 | 18.4 | Yes |
| TTS-6A6 | 77.15 | 18.5 | Yes |
| TTS-6A7 | 91.03 | 19.9 | Yes |
| TTS-6A8 | 112.25 | 23.6 | Yes |
| TTS-6A9 | 113.62 | 23.7 | Yes |
| TTS-6A10 | 114.92 | 23.8 | Yes |
| TTS-6A11 | 114.92 | 23.8 | Yes |
| TTS-6A12 | 119.31 | 24.9 | Yes |
| TTS-6A13 | 119.53 | 25 | Yes |
| TTS-6A14 | 120.43 | 25.5 | Yes |

Site Specific Integration in the Transgenic Target Event TTS-6A3

The transgenic event representing TTS-6A3 (FIG. 5B, table 6 A) was further evaluated by testing its capability for site specific integration. The FRT sites were first sequence verified as previously described and confirmed to be intact. Particle bombardment was used as the method of DNA delivery and the same donor plasmid, PHP27064, containing FRT1 and FRT87 was delivered into heterozygous immature embryos containing TTS-6A3 for SSI. The methods used to perform SSI were the same as described in Example 2. In addition, a similar series of qPCR assays to those listed for Example 2 was used to indicate that SSI had occurred. These included checking the copy number of each gene between the FRT sites that originally resided in the target (MO-PAT) and donor (HT, YFP) plasmids as well as detection assays for the other co-bombarded plasmids (flp, zm-odp2, zm-wus). Assays specific to the newly formed, recombinant target locus which span the FRT sites are key to the determination that SSI had occurred. Methods used for the real time quantitative PCR analysis are the same as those listed for Example 2.

There were approximately 4500 immature embryos heterozygous for TTS-6A3, that were co-bombarded using the donor plasmid, PHP27064, and the SSI associated plasmids with FLP recombinase, ODP2, and WUS (FIG. 7). Bombarded embryos were transferred to selective culture medium with glyphosate as described above and then cultured for callus growth. Callus growing in the presence of glyphosate and showing a yellow fluorescent phenotype when viewed under a dissecting microscope with the appropriate light source and filters was advanced for plant regeneration. We were co-processing material from both TTS-6A3 and TTS-6A4 (Table 7) at the time and observed some differences in YFP phenotype where YFP was uniform and relatively strong from all of the callus events from TTS-6A3, but weaker and mottled in the TTS-6A4 transgenic callus (Table 7). A significant number of independent transgenic calli with the desired phenotype were advanced into regeneration and regenerated plants were recovered. Leaf tissue from plants was analyzed by qPCR analysis to show that SSI was achieved and often in the absence of integration of the assisting plasmids with flp, zm-wus, and zm-odp2 (Table 8). In the final analysis, there were a few additional SSI transgenics that dropped out even though the callus showed the desired phenotype. Some like event number 6 showed SSI but additional integration of PHP27064 and PHP31729. Looking at just the clean SSI events, including event numbers 1-2, 4, 7, and 9, we were able to achieve a 0.11% SSI transformation frequency based on starting embryo numbers in the TTS-6A3 locus. These 5 independent RMCE events were recovered to the greenhouse and set seed and additional molecular analysis was planned.

TABLE 7

SSI transformation by particle bombardment.

| Target | Donor | Explant (no.) | RMCE (no.) | Frequency | YFP |
|---|---|---|---|---|---|
| TTS-6A3 | PHP27064 | 4498 | 9 | 0.21% | High, uniform |
| TTS-6A4 | PHP27064 | 3118 | 19 | 0.60% | Low, spotted |

TABLE 8 qPCR analysis of regenerated plants from glyphosate resistant, yellow fluorescent calli from immature embryo containing TTS-6A3 target site. Transformation methods for site specific integration were used to introduce PHP27064. qPCR analysis was used to detect SSI and the presence of plasmids including PHP21139, PHP5096, PHP31729, and PHP27064.

| Callus Event | Plant (No.) | FRT1, FRT87 | Donor (HT, yfp) | Target (mopat) | Extras (odp2, wus, flp) |
|---|---|---|---|---|---|
| 1 | 10 | 10/10 | 10/10 | 10/10 | 10/10 |
|  |  |  | single copy | NEG | NEG |
| 2 | 5 | 5/5 | 5/5 | 5/5 | 5/5 |
|  |  |  | single copy | NEG | NEG |
| 3 | 9 | 9/9 | 9/9 | 9/9 | 9/9 |
|  |  |  | single copy | POS | POS |
| 4 | 1 | 1/1 | 1/1 | 1/1 | 1/1 |
|  |  |  | single copy | NEG | NEG |
| 5 | 2 | 2/2 | 2/2 | 2/2 | 2/2 |
|  |  |  | multi-copy | POS | POS (wus) |
| 6 | 8 | 8/8 | 8/8 | 8/8 | 8/8 |
|  |  |  | multi-copy | NEG | POS (odp2) |
| 7 | 3 | 3/3 | 3/3 | 3/3 | 3/3 |
|  |  |  | single copy | NEG | NEG |
| 8 | 2 | 0/2 | 2/2 | 2/2 | 2/2 |
|  |  |  | multi-copy | NEG | NEG |
| 9 | 8 | 8/8 | 8/8 | 8/8 | 8/8 |
|  |  |  | single copy | NEG | NEG |

POS = qPCR detection positive.
NEG = qPCR detection negative.
YFP = yellow fluorescent protein (ZS-Yellow1 N1, Clontech) DNA sequence.
HT = herbicide tolerance gene.
odp2 = maize ovule development protein 2 sequence.
wus = maize wuschel sequence.
FLP = yeast flp recombinase sequence.

In summary, TTS-6A3 was generated using an SSI platform II construct (PHP36678) different from that (PHP36680) used in Example 2 only by inclusion of different trait genes. This transgenic target site was selected because it was characterized as a single copy T-DNA insertion using qPCR analysis during the transformation process. Leaf samples from the first generation IE-7 transgenic plant were submitted for flanking sequence analysis and the resulting flanking sequence data was used to provide an assessment of the genomic position of TTS-6A3 very near to Trait6A on chromosome VI. Later mapping data confirmed the chromosome 6 location initially estimated using flanking sequence data. IE7 was next characterized for SSI transformation frequency using PHP27064 and demonstrated a 0.11% RMCE frequency based on initial qPCR analysis.

Generating a Transgenic Plant Containing the Complex Trait Loci 6A (CTL6A)

Building complex trait locus 6A involves crossing or re-transforming transgenic plants comprising transgenic target sites with events comprising various trait genes in the appropriate region on chromosome VI (as illustrated in FIG. 1). We identified a number of transgenic target site candidates from maize inbred 1 and maize inbred 2 which were predicted to be located in the same region as Trait6A (FIG. 5B). If these insertions were not made with desired trait genes for a particular region, then the desired genes can be inserted via SSI as was demonstrated on chromosome 1 for TTS-6A2 and on chromosome 6 for TTS-6A3. Once the desired genes were inserted, then recombination must take place to physically link the transgenic insertion sites. We began by working to obtain linkage between TTS-6A3 and Trait6A using meiotic recombination during flowering.

TTS-6A3 was predicted to be 2.6 cM away from Trait6A based on an internally derived single meiosis map (PHB) and therefore a prediction can be made that there would be a nearly 100% chance of finding 5 recombinants in 500 progeny. The breeding scheme for physical linkage should work for any 2 insertion sites or genomic points of interest (transgenic insertions, native traits, QTL's, haplotypes, chromosomal regions of interest, etc.), or combinations of the two (Table 3). The work involving Trait6A and TTS-6A3 was essentially the same as that described in Example 2 above.

Seed comprising the Trait6A locus and TTS-6A3 were planted in subsequent weekly plantings and the plants matured to flowering stage. In this work we used qPCR copy number analysis to identify the homozygous individuals from segregating populations. At flowering, homozygous plants for TTS-6A3 were used as a pollen source for plants with the Trait6A locus. Ears were harvested from these crosses, dried down, and F1 kernels collected. The F1 kernels were planted and the resulting plants were screened as seedlings by qPCR to confirm that both transgenic loci were present. Crossing two homozygous transgenic lines insured that each of the F1 progeny had both transgenic insertions. F1 TTS-6A3/Trait6A kernels were planted along with kernels of another suitable non-transgenic line to act as a female in cross pollination. When the plants had developed to flowering stage, transgenic pollen was carried to the non-transgenic recipient line. F2 kernels from these crosses were planted in larger numbers in flats to screen for recombinants between TTS-6A3 and Trait6A. A double herbicide screen was used to select plants that were both glyphosate and bialaphos resistant. Bialaphos was applied first when the seedlings were only approximately 10 d after germination. At approximately 3 wk after germination, glyphosate was applied. Double resistant plants would be potted for recovery and self-pollination to demonstrate the linkage of the two transgenic traits. Two independent tests were completed involving the germination of 500 kernels for double herbicide treatment. In the first set of 500, we identified 5 double resistant individuals. The second set of 500 plants only yielded 2 double resistant individuals. All of the plants resistant to both bialaphos and glyphosate were grown to flowering and self-pollinated. The progeny of these crosses would segregate in a ratio of one homozygous to 2 heterozygous to 1 null for the two herbicide resistance transgenes. A small set was analyzed for this segregation and the results are included in Table 9. In conclusion, the analysis demonstrated that the two transgenes were segregating as a single genetic locus. This confirmed our ability to link the two loci, TTS-6A3 and Trait6A, into a single trait locus on chromosome 6 to create CTL6A.

TABLE 9

Zygosity qPCR analysis of progeny from self-pollinations of individual F2 plants resistant to both Round Up ® and Liberty ® herbicides.

| F2 Plant | Seed ID | Homozygous | Heterozygous | Null | Chi$^2$ |
|---|---|---|---|---|---|
| 1 | 40047413 | 6 | 17 | 9 | 0.68 |
| 2 | 40047414 | 4 | 20 | 8 | 3.00 |
| 3 | 40047431 | 5 | 18 | 7 | 1.46 |

Additional Development of Complex Trait Loci 6A (CTL6A)

All the transgenic target sites listed in Table 6A for CTL6A were advanced into SSI transformation work following initial determination of insertion site flanking sequence and FRT site sequence. Repeat submission of samples to verify flanking sequence usually resulted in verification of the initial results (data not shown). Sometimes the second pass flanking sequence analysis resulted in better quality sequence data than the original. Seed increases were completed for each of these lines to facilitate additional testing in the third generation. Third generation seedlings were grown out for additional sampling and analysis including qPCR, Southern analysis, and ELISA analysis for expression (FIG. 10). Samples were collected and analyzed using quantitative ELISA analysis in order to characterize expression properties at each insertion site. Larger numbers of samples could be tested since these were young plants (approx. V3/V4) growing in flats. Data in FIG. 10 shows that the ELISA levels for GENE 1, GENE2 and PAT were similar at multiple independent insertion sites except for the first event which was shown to have a rearranged T-DNA right border (RB) region. Follow up flanking sequence analysis indicated the problem with the insertion of the first transgenic population. Mature seedlings were sacrificed after sampling to large leaf samples for high quality genomic DNA extraction and Southern analysis. Site Specific integration occurred at all Target Sites listed in Table 6B (TTS6A5-TTS6A14) as described below.

Site Specific Integration of Target Sites TTS6A5-TTS6A14 (Table 6B).

Many loci that are part of CTL6A were further characterized by testing their capability for site specific integration (SSI) including TTS-6A5, TTS-6A6, TTS-6A7, TTS-6A8, TTS-6A9, TTS-6A10, TTS-6A11, TTS-6A12, TTS-6A13, and TTS-6A14. Using methods for site specific integration described in Example 1, a construct named PHP46438 was introduced independently into each of these loci. PHP46438 is similar to PHP27064 (FIG. 7) except that it contained a promoterless NPTII as the first gene in the construct and a constitutive AM-CYAN1 gene expressed by the maize ubiquitin promoter as the second. Multiple independent candidates were recovered for PHP46438 insertion at each of the 10 loci, T0 transgenic plants were regenerated from each candidate, and real time qPCR analysis was used to identify the events where RMCE had occurred. Plants with the best qPCR profiles were then recovered to the greenhouse, grown to maturity, and allowed to set seed. Seed of the next (T1) generation were grown in flats and analyzed by real time qPCR to characterize transgene segregation to confirm Mendelian inheritance and to identify homozygous for seed increase. Transgene positive individuals were sampled for further molecular analysis including Southern analysis, sequencing, and ELISA characterization. These analyses provided the further confirmation of successful RMCE and site specific integration at all the loci of CTL6A.

Example 4

Production of a Soybean Library Comprising Transgenic Target Sites for Site Specific Integration (SSI)

Methods of generating transgenic plants, seeds or plant cells comprising various transgenic target sites (TTS) with precise transgene integrations for site specific integration (SSI) were developed for soybean. Transgenic target events were produced by biolistic bombardment methods and the transgene integrations were evaluated by sequencing flanking genomic DNA borders.

Development of SSI Target Vectors

The target DNA construct QC599 was modified following standard molecular cloning procedures from a previous SSI target DNA QC288 (Li et al., Plant Physiol. 151:1087-1095, 2009). QC599 carried the same pair of dissimilar recombination sites FRT1 and FRT87 to enable subsequent site specific integration (SSI) transformation using the yeast FLP/FRT system. The soybean S-adenosyl methionine synthetase promoter GM-SAMS PRO (U.S. Pat. No. 7,217,858B2) was used to drive the expression of the hygromycin phosphotransferase (HPT) gene for soybean transformation selection. Open reading frame stop codon sequences ORFSTOP-B (SEQ ID NO:12) and ORFSTOP-A (SEQ IS NO:13) were added to the expression cassette ends of QC599 to prevent any potential open reading frames from being created when QC599A target gene integrated in soybean genome (FIG. 11). The target DNA fragment QC599A used for biolistic bombardment transformation was released from construct QC599 by AscI restriction enzyme digestion and purified from agarose gel with a DNA gel extraction kit (QIAGEN®, Valencia, CA).

The FRT1 site was placed between the SAMS promoter and HPT coding region to set up a gene-trapping configuration. The FRT87 site was placed downstream of the NOS terminator and in front of the ORFSTOP-A at the very 3' end of the target gene cassette. During SSI transformation described schematically in FIG. 12, a SSI donor DNA containing a promoterless marker gene plus any trait genes such as a cyan fluorescent protein gene CFP flanked together by the same dissimilar FRT1 and FRT87 sites was introduced by biolistic bombardment into cells containing the transgenic target gene. DNA recombination between the corresponding FRT1 and FRT87 recombination sites of the donor and target DNA will result in the cassette exchange between the donor and target DNA in the presence of FLP recombinase, i.e., every components flanked by the FRT1 and FRT87 sites are exchanged between the donor and target DNA in a successful RMCE (Recombinase Mediated Cassette Exchange). As a result, the initial target selectable marker gene HPT was replaced by the newly introduced selectable marker gene HRA (mutated acetolactate synthase) from the donor to enable the RMCE event to tolerate chlorsulfuron. The ORFSTOP-B, SAMS promoter on the 5' end and the ORFSTOP-A on the 3' end of the target gene are fixed at the target site and cannot be replaced by RMCE.

Development of SSI Transgenic Target Events by Biolistic Transformation

Purified QC599A DNA fragment was transformed to a Pioneer elite soybean cultivar by the method of biolistic bombardment (Klein et al., Nature 327:70-73 (1987); U.S. Pat. No. 4,945,050) as described in detail below to create transgenic target events from which desired SSI target sites would be identified by molecular assays and sequence analysis.

Soybean cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, CA). To 50 µl of a 60 mg/ml 1.0 mm gold particle suspension were added (in order): 30 µl of 30 ng/µ0.1 QC599A DNA fragment, 20 µl of 0.1 M spermidine, and 25 µl of 5 M $CaCl_2$). The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 µg/ml hygromycin B as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 µg/ml hygromycin B selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production.

Identification of SSI Transgenic Target Sites

Transgenic events sampled at early somatic stage were analyzed by real time quantitative PCR (qPCR) to assess the copy numbers of the QC599A transgenic target gene and then by inverse PCR to sequence the genomic DNA borders flanking the QC599A transgene of only the single copy events identified by the qPCR.

Genomic DNA were extracted from somatic embryo samples and analyzed by quantitative PCR using the 7500 real time PCR system (Applied Biosystems) with gene-specific primers and fluorescence probes to check copy numbers around both the FRT1 and FRT87 sites of transgenic QC599A. The qPCR analysis was done in duplex reactions with a heat shock protein (HSP) gene as the endogenous controls and a transgenic DNA sample with a known single copy of QC599A transgene as the calibrator using the relative quantification methodology (Applied Biosystems). The endogenous control HSP probe was labeled with VIC and the target gene probes were labeled with FAM for the simultaneous detection of both fluorescent probes. Only events identified to be single copy by both the FRT1 and FRT87 qPCR assays were further analyzed and advanced to regenerate plants.

The same genomic DNA used for qPCR of selected single copy events were fragmented with three different restriction enzymes AflII, NsiI, and PciI that all cut QC599A only once and all in the NOS region so common primers could be used for inverse PCR (FIG. 13). For example, PciI cut transgene QC599A once in the NOS region and once in the flanking genomic DNA border nearest to the 5' end of QC599A to create a DNA fragment containing a genomic DNA segment bordering the 5' part of QC599A and the 5' portion of transgenic QC599A with PciI half site on both the 5' and 3' ends. Similarly, a DNA fragment containing the 3' portion of transgenic QC599A and a genomic DNA segment bordering the 3' end of QC599A was simultaneously created also ending with PciI half site on both 5' and 3' ends. A self ligation step then circularized both the 5' border and 3' border fragments making their genomic DNA portions amplifiable by PCR using only QC599A-specific primers Two rounds of PCR amplification were applied to minimize the amplification of any non-specific genomic DNA fragments (FIG. 13). Invitrogen high fidelity Taq DNA polymerase was used to amplify the digested and then self-ligated genomic DNA templates 25 cycles by the first PCR. Then 1% of each first PCR product was amplified 35 cycles by the second PCR. The second PCR products were checked by agarose gel electrophoresis and most of the times distinct bands were amplified. The PCR product displayed a distinct band was then sequenced using the Sanger method with the same corresponding sense and antisense primers used in the second PCR. Sequences were assembled and analyzed using programs in the Vector NTI suites (Invitrogen). Sequences were used to BLAST search the Joint Genome Institute soybean genome sequences publically available to identify their locations in the genome by sequence homology.

Total of 830 QC599A transgenic events were produced and analyzed for copy numbers by qPCR and 360, up to 43% of the total, were selected as single copy events for border sequencing by inverse PCR (Table 10). Both 5' and 3' border sequences were obtained from 239 of the single copy events. But the majority of them have a 5' border and a 3' border that are often from different chromosomes or are not naturally continuous even when they are on the same chromosome. Only 19 of the sequenced 239 events have their 5' border and 3' border on the same chromosome and also are naturally continuous. Some of them may have small deletions or insertions at the transgenic QC599A insertion site. The 19 events are considered as quality events with matching genomic DNA borders and selected as SSI target lines to be used for future SSI transformation.

TABLE 10

Soybean SSI target events evaluation.

| Sample Description | Sample No. |
|---|---|
| Total events submitted for copy number check by qPCR | 830 |
| Single copy events selected for inverse PCR | 360 |
| Events with 5' border inverse PCR bands | 313 |
| Events with 3' border inverse PCR bands gene | 310 |
| Events with both 5' and 3' border inverse PCR bands | 274 |
| Events with 5' border sequences | 281 |
| Events with 3' border sequences | 247 |
| Events with both 5' and 3' border sequences | 239 |
| Events with matching 5' and 3' border sequences | 19 |

When an SSI transgenic target site was identified in a genomic locus of interest in the soybean genome then the regenerated T0 plant was analyzed by qPCR and Southern hybridization to confirm previous copy number check and border sequencing results. Multiple digestions such as NdeI, NsiI, and PciI and different probes specific to the SAMS promoter, HPT coding region, and flanking genomic borders were used in the Southern analysis and all the bands had to match the sizes predicted from the genomic DNA sequences surrounding the insertion site in order to confirm the target site.

Transgenic SSI target T0 plants were maintained in controlled growth chambers and monitored for agronomic abnormality until T1 seeds were harvested. Sixty four T1 seeds of each target event were planted and T1 plants were analyzed by the same FRT1 and FRT87 qPCR assays to check transgenic QC599A segregation. Selected homozygous T1 plants were then sampled and analyzed by similar Southern hybridization to confirm previous Southern results obtained on the T0 plant. Only after passing all the above evaluations, a SSI transgenic target event containing a transgenic target site was advanced as a recombination target locus (RTL) that could be used as a target line in SSI transformation.

Example 5

Production of a Complex Trait Locus on Chromosome 19

One valuable region of the soybean genome, referred to as Complex Trait Locus LA (CTL-LA), was identified containing a trait of interest (Trait-LA) on chromosome 19 (or linkage group L) and at least two SSI target sites in its proximity (FIG. 14).

Identification of Complex Trait Locus

The location of the trait of interest Trait-LA on chromosome 19 was determined based on sequence homology following the determination of transgenic target sites flanking sequences and then verified by physical and genetic mapping data. Transgenic target site flanking sequences (FS) were obtained by using inverse PCR. Each FS sequence was compared to the soybean whole genome sequence using the BLAST algorithm to predict its location to a chromosome since most soybean genome sequences have been assembled into 20 individual chromosomes (DNA markers close to the FS location identified by sequence continuity were then used to associate the FS location, which represents the transgenic SSI target site location, to the soybean genetic map. Finally, the genetic map position of the transgenic SSI target site was used to determine if it is close to a trait gene of interest. As an example in this application, two transgenic SSI target sites TTS-LA1 and TTS-LA2 were found to be in the proximity of the trait gene of interest Trait-LA. In conclusion, a complex trait locus named CTL-LA was created containing the native trait gene LA locus and two nearby transgenic SSI target loci TTS-LA1 ad TTS-LA2 (FIG. 14). The independent transgenic loci can then be brought together to the native trait locus from different parents by breeding and then the complex trait locus can segregate in subsequent breeding steps as a single genetic locus.

TABLE 11

Complex trait locus CTL-LA on chromosome 19 of soybean.

| LOCUS | Soybean Composite Public map | Pioneer Soy v1.2 |
|---|---|---|
| SATT613 | 36.04 | 45.1 |
| SATT284 | 38.16 | 47.7 |
| S60414-TB |  | 49.3 |
| SATT462 | 41.0 | 49.3 |
| TTS-LA1 |  | 57.2 |
| TRAIT-LA |  | 60.1 |
| TTS-LA2 |  | 62.9 |
| SATT481 | 54.57 | 65.8 |
| SATT156 | 56.13 | 65.8 |
| SCT_010 | 59.52 | 68.5 |

In the process of developing a soybean TTS library, two transgenic SSI target sites TTS-LA1 and TTS-LA2 were identified on Chromosome 19 near a trait of interest Trait-LA. The insertion site of TTS-LA1 was determined to be only approximately 2.9 cM (centi-Morgan) close to a trait of interest (Trait-LA) mapped at position 60.1 cM on chromosome 19 of proprietary Pioneer soybean map v1.2 (Table 11) while TTS-LA2 was approximately 2.8 cM close to the Trait-LA on the opposite side of TTS-LA1. More genetic markers and associated trait genes within approximately 10 cM of the Trait-LA locus are obvious from the map and some of them are listed in Table 11. The corresponding positions of some of the same markers on the soybean composite public map were determined by searching the markers on the public map (Table 11).

Site Specific Integration at Transgenic Target Sites TTS-LA1 and TTS-LA2

The transgenic events containing either the TTS-LA1 or the TTS-LA2 sites were further evaluated by testing its capability for site specific integration of genes of interest. T0 transgenic plants of the two events were brought to maturity and T1 seeds were planted in controlled growth chambers. Leaf samples of T1 transgenic plants were first analyzed by FRT1 and FRT87 qPCR to confirm that the single copy QC599A DNA fragment segregate Mendelian inheritance and to identify homozygous plants. Selected homozygous T1 plants were analyzed by Southern hybridization to confirm that the hybridized bands match the sizes predicted from the genomic DNA sequence of the chromosome 19 segment harboring the QC599A transgene. A part of the 5' border, the entire QC599A DNA fragment, and a part of the 3' border were also amplified by PCR using a 5' border sense primer and a 3' border antisense primer and sequenced to confirm both the transgene and the border junctions to be intact.

Developing T2 embryos were excised from the homozygous T1 plants and used as explants to initiate tissue cultures which were then transformed with a SSI donor DNA construct with the help of a FLP expression construct by biolistic bombardment as described in EXAMPLE 4. One target site TTS-LA1 was transformed with a SSI donor DNA construct QC728 containing one or more trait genes of interest. FLP recombinase activity was provided by the transient expression of the cobombarded DNA construct QC663. Only SSI transgenic events in which the GM-ALS marker gene of the donor QC728 was placed through FLP recombinase mediated DNA recombination downstream of the GM-SAMS promoter of the QC599A transgene at the TTS-LA1 target site were selected with 90 ng/ml chlorsulfuron. Transgenic events were sampled at callus stage and analyzed by a series of qPCR assays to determine if SSI had occurred and RMCE events were produced in a manner similar as depicted in FIG. 12. Different traits such as herbicide tolerance genes were integrated at the other SSI target site TTS-LA2 following similar transformation procedure using different donor DNA constructs and the transgenic events were analyzed by similar qPCR assays.

Since the SSI target events containing QC599A DNA fragment were transformed with a donor DNA in the presence of a FLP expression DNA construct to produce a RMCE through FLP mediated recombination, four DNA including the target QC599A, the donor QC728, the FLP expression construct QC663, and the RMCE product QC599A728A could coexist in any transgenic events that passed chlorsulfuron selection. Randomly integrated DNA can be segregated away from the RMCE locus to generate a clean RMCE event comprising a trait of interest at one locus (integrated at either TTS-LA1 or TTSLA2). Cumulative qPCR results showed that SSI had occurred and RMCE events were recovered from both TTS-LA1 and TTS-LA2 transformation.

Transgenic events comprising a RMCE at TTS-LA1 can be crossed with transgenic events comprising a RMCE at TTS-LA2 to generate a complex trait loci comprising stacked traits of interest.

Generating a Transgenic Plant Containing the Complex Trait Locus CTL-LA

In order to build the complex trait locus CTL-LA, transgenic plants carrying trait genes at TTS-LA1 site need to be crossed with transgenic plants carrying different trait genes at TTS-LA2 site (FIG. 14). Since TTS-LA1 site is 2.9 cM away from Trait-LA and TTS-LA2 site is 2.8 cM of Trait-LA, the total distance between TTS-LA1 and TTS-LA2 sites is 5.8 cM. When two RMCE events with trait genes at each the TTS-LA1 and TTS-LA2 sites are crossed, there is close to 6% chance of finding a progeny carrying the traits at both sites after only one generation since one cM is equal to a 1% chance that a marker at one genetic locus will be separated from a marker at another locus due to crossing over in a single generation.

Selected RMCE events containing the trait gene of interest at TTS-LA1 can be brought to maturity and their homozygous T1 plants can be identified by qPCR, evaluated by Southern hybridization and phenotypic analysis. One perfect RMCE event can be selected as a parent. Another parent can be selected from RMCE events with, for example, herbicide tolerance traits at TTS-LA2 site through similar qPCR, Southern hybridization, and phenotypic analysis. The two parents can be crossed and the resulting progenies can be analyzed by qPCR assays specific to each parent to identify recombinants that contain both TTS-LA1, TTS-LA2, traits as well as the native trait Trait-LA between them (FIG. 14). F1 seeds of the identified recombinants can be planted and T2 progenies homozygous for the TTS-LA1-Trait-LA-TTS-LA2 complex trait locus CTL-LA can be produced when the plants are naturally self-pollinated. The homozygous TTS-LA1-Trait-LA-TTS-LA2 complex trait locus can be identified by similar qPCR assays and can be propagated subsequently as a single locus.

TABLE 12

Summary of SEQ ID NOS.

| SEQ ID NO: | NT/AA | Description |
| --- | --- | --- |
| 1 | NT | Minimal FRT1 recombination site |
| 2 | NT | Minimal FRT5 recombination site |
| 3 | NT | Minimal FRT6 recombination site |
| 4 | NT | Minimal FRT7 recombination site |
| 5 | NT | Minimal FRT12 recombination site |
| 6 | NT | Minimal FRT87 recombination site |
| 7 | NT | Cre recombinase |
| 8 | NT | FLP recombinase |
| 9 | NT | Variant of Cre recombinase (moCre-maize preferred codons) |
| 10 | NT | Variant of FLP recombinase (FLPm-maize preferred codons) |
| 11 | NT | SSI target DNA fragment QC599A used for biolistic soybean transformation to create transgenic target events. |
| 12 | NT | An oligonucleotide containing stop codons in all six possible open reading frames- ORFSTOP-B. |
| 13 | NT | Another oligonucleotide containing stop codons in all six possible open reading frames- ORFSTOP-A. |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A maize plant or seed having in its genome a genomic window comprising at least a first transgenic target site comprising at least two non-identical FRT recombination sites, a second transgenic target site comprising at least two nonidentical FRT recombination sites, and a genomic locus of interest; wherein each of said genomic locus of interest, said first transgenic target site and said second transgenic target site have different genomic sites; and wherein the genomic window is flanked by a first marker and a second marker; wherein the first marker is MMP76, and the second marker is RZ444E.

2. The maize plant or seed of claim 1, wherein the non-identical FRT recombination sites of the first transgenic target site comprise a FRT1 site, a FRT5 site, a FRT6 site, a FRT7 site, a FRT12 site, or a FRT87 site.

3. The maize plant or seed of claim 1, wherein the non-identical FRT recombination sites of the second transgenic target site comprise a FRT1 site, a FRT5 site, a FRT6 site, a FRT7 site, a FRT12 site, or a FRT87 site.

4. The maize plant or seed of claim 1, wherein the non-identical FRT recombination sites of the first transgenic target site comprise a FRT1 site and a FRT87 site.

5. The maize plant or seed of claim 1, wherein the non-identical FRT recombination sites of second first transgenic target site comprise a FRT1 site and a FRT87 site.

6. The maize plant or seed of claim 1, wherein the non-identical FRT recombination sites of the first transgenic target site comprise a FRT1 site and a FRT6 site.

7. The maize plant or seed of claim 1, wherein the non-identical FRT recombination sites of second transgenic target site comprise a FRT1 site and a FRT6 site.

8. The maize plant or seed of claim 1, wherein said genomic window further comprises a third transgenic target site comprising a fourth FRT recombination site, a fifth FRT recombination site and a sixth FRT recombination site, wherein
  (i) said fourth, fifth and said sixth FRT recombination sites are dissimilar with respect to one another; or
  (ii) said fourth, fifth and said sixth FRT recombination sites are dissimilar and have a decreased compatibility with respect to one another;
  and said third transgenic target site has a different genomic insertion site than said first transgenic target site, said second transgenic target site and said genomic locus of interest.

9. The maize plant or seed of claim 1, wherein
  (a) said genomic locus of interest confers a trait comprising male sterility, site-specific recombination, abiotic stress tolerance, altered phosphorus, altered antioxidants, altered fatty acids, altered essential amino acids, altered carbohydrates, herbicide tolerance, insect resistance or disease resistance; or
  (b) said genomic locus of interest comprises a transgene or a native trait.

10. The maize plant or seed of claim 1, wherein said first transgenic target site or said second transgenic target site comprises at least one polynucleotide of interest.

11. The maize plant or seed of claim 1, wherein said second transgenic target site comprises
  (a) the same non-identical FRT recombination sites as said first transgenic target site; or
  (b) different non-identical FRT recombination sites as said first transgenic target site.

12. The maize plant or seed of claim 1, wherein the non-identical FRT recombination sites of the first transgenic target site and the second transgenic target site comprise a FRT site, or a mutant FRT site.

13. A method for producing a second maize plant, the method comprising applying plant breeding techniques to a first maize plant, or parts thereof, wherein said first maize plant is the maize plant of claim 1, and wherein application of said techniques results in the production of said second maize plant, wherein said second maize plant comprises at least one additional transgenic target site or at least one additional genomic locus of interest within said genomic window when compared to said first maize plant; wherein each of said additional transgenic target site and said additional genomic locus of interest have a different genomic insertion site with respect to each other and with respect to said first transgenic target site, said second transgenic target site and said genomic locus of interest.

14. The method of claim 13, wherein the at least one additional transgenic target site comprises a polynucleotide of interest.

15. The method of claim 13, wherein said second maize plant comprises at least one less transgenic target site or at least one less genomic locus of interest within said genomic window when compared to said first maize plant.

16. A method of producing a complex trait locus in the genome of a maize plant, the method comprising:
  (a) providing a first maize plant having in its genome a genomic window comprising at least a first transgenic target site comprising at least two non-identical FRT recombination sites, and wherein said first maize plant does not comprise a first genomic locus of interest; wherein the genomic window is flanked by a first marker and a second marker; wherein the first marker is MMP76, and the second marker is RZ444E;

(b) breeding to said first maize plant a second maize plant comprising at least two non-identical FRT recombination sites, wherein said second maize plant comprises in its genome the first genomic locus of interest and said second maize plant does not comprise said first transgenic target site; and, (c) selecting a progeny maize plant from step (b) comprising said first transgenic target site and said genomic locus of interest; wherein said first transgenic target site and said first genomic locus of interest have different genomic insertion sites in said progeny maize plant.

17. A method of producing a complex trait locus in the genome of a maize plant, the method comprising:

(a) providing a first maize plant having in its genome a genomic window at least a first transgenic target site and a second transgenic target site having different genomic insertion sites, wherein said first transgenic target site comprises at least two nonidentical FRT recombination sites and said second transgenic target site comprises at least two non-identical FRT recombination sites, wherein said first maize plant does not comprise a first genomic locus of interest; wherein the genomic window is flanked by a first marker and a second marker; wherein the first marker is MMP76, and the second marker is RZ444E;

(b) breeding to said first maize plant a second maize plant, wherein said second maize plant comprises in its genome the first genomic locus of interest, wherein said second maize plant does not comprise said first transgenic target site or said second transgenic target site; and, (c) selecting a progeny maize plant from step (b) comprising said first transgenic target site, said second transgenic target site and said first genomic locus of interest;

wherein each of said first transgenic target site, said second transgenic target site and said first genomic locus of interest have a different genomic insertion site in said progeny maize plant.

18. The method of claim 17, wherein said method further comprises (a) breeding to said progeny maize plant a third maize plant comprising a second genomic locus of interest, wherein said third maize plant comprises in said genomic window said second genomic locus of interest, wherein said third maize plant does not comprise said first transgenic target site, said second transgenic target site or said first genomic locus of interest in said genomic window; and, (b) selecting a second progeny maize plant from step (a) comprising said first transgenic target site, said second transgenic target site, said first genomic locus of interest, and said second genomic locus of interest; wherein each of said first transgenic target site, said second transgenic target site, said first genomic locus of interest and said second genomic locus of interest have a different genomic insertion site in said second progeny maize plant.

19. The method of claim 17, wherein (a) the first genomic locus of interest confers a trait comprising male sterility, site specific recombination, abiotic stress tolerance, altered phosphorus, altered antioxidants, altered fatty acids, altered essential amino acids, altered carbohydrates, herbicide tolerance, insect resistance or disease resistance; or (b) the first genomic locus of interest comprises a native trait locus, a transgene of interest, or an additional transgenic target site.

20. The method of claim 17, wherein (a) said first transgenic target site comprises a first FRT recombination site and a second FRT recombination site, wherein (i) said first and said second FRT recombination sites are dissimilar with respect to one another and, said first transgenic target site comprises a polynucleotide of interest; or (ii) said first and said second FRT recombination sites are non-identical and have a decreased compatibility with respect to one another and, said first transgenic target site comprises a polynucleotide of interest; and, (b) said second transgenic target site comprises a third FRT recombination site and a fourth FRT recombination site, wherein (i) said third and said fourth FRT recombination sites are non-identical with respect to one another; and said second transgenic target site further comprises a second polynucleotide of interest; or (ii) said third and said fourth FRT recombination sites are non-identical and have a decreased compatibility with respect to one another; and said second transgenic target site further comprises a second polynucleotide of interest.

21. The method of claim 20, wherein said first transgenic target site and said second transgenic target site comprise (a) the same non-identical FRT recombination sites; or (b) different non-identical FRT recombination sites.

22. The method of claim 20, wherein the non-identical FRT recombination sites comprise a FRT site, or a mutant FRT site.

* * * * *